US010081615B2

(12) United States Patent
Choi

(10) Patent No.: US 10,081,615 B2
(45) Date of Patent: Sep. 25, 2018

(54) SULFAMATE DERIVATIVE COMPOUNDS FOR USE IN TREATING OR ALLEVIATING PAIN

(71) Applicant: Bio-Pharm Solutions Co., Ltd., Suwon-si, Gyeonggi-do (KR)

(72) Inventor: Yong Moon Choi, Seoul (KR)

(73) Assignee: Bio-Pharm Solutions Co., Ltd., Gyeonggi-do (KR)

( * ) Notice: Subject to any disclaimer, the term of this patent is extended or adjusted under 35 U.S.C. 154(b) by 75 days.

(21) Appl. No.: 15/103,595

(22) PCT Filed: Dec. 12, 2014

(86) PCT No.: PCT/KR2014/012260
§ 371 (c)(1),
(2) Date: Jun. 10, 2016

(87) PCT Pub. No.: WO2015/088272
PCT Pub. Date: Jun. 18, 2015

(65) Prior Publication Data
US 2016/0311792 A1 Oct. 27, 2016

Related U.S. Application Data

(60) Provisional application No. 61/915,042, filed on Dec. 12, 2013.

(51) Int. Cl.
*C07D 319/08* (2006.01)
*C07D 321/10* (2006.01)
(52) U.S. Cl.
CPC ......... *C07D 319/08* (2013.01); *C07D 321/10* (2013.01)
(58) Field of Classification Search
None
See application file for complete search history.

(56) References Cited

U.S. PATENT DOCUMENTS 4,582,916 A 4/1986 Maryanoff et al.
4,591,601 A 5/1986 Maryanoff et al.
(Continued)

FOREIGN PATENT DOCUMENTS

WO 2008054291 A1 5/2008
WO 2013187727 A1 12/2013

OTHER PUBLICATIONS

Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London.Series B, Biological Sciences, vol. 236, No. 1283, p. 101-113.*

(Continued)

*Primary Examiner* — Kathrien A Cruz
*Assistant Examiner* — Andrew P Lee
(74) *Attorney, Agent, or Firm* — McDonnell Boehnen Hulbert & Berghoff LLP

(57) ABSTRACT

The present invention relates to sulfamate derivative compounds and a composition for treating and/or alleviating pain containing the sulfamate derivative compounds or a pharmaceutically acceptable salt thereof as an active ingredient. More specifically the present invention relates to a pharmaceutical composition for treating or alleviating pain containing a sulfamate derivative compound and/or a pharmaceutically acceptable salt thereof as an active ingredient. Furthermore, the present invention relates to a method for treatment or alleviation of pain comprising administering a sulfamate derivative compound in a pharmaceutically effective amount to a subject in need of treatment or alleviation of pain.

24 Claims, 1 Drawing Sheet

(56) References Cited

U.S. PATENT DOCUMENTS

| | | |
|---|---|---|
| 4,792,569 A | 12/1988 | Maryanoff et al. |
| 5,998,380 A | 12/1999 | Ehrenberg et al. |
| 8,084,490 B2 | 12/2011 | Mccomsey et al. |
| 2010/0063138 A1 | 3/2010 | Mccomsey et al. |
| 2013/0252924 A1 | 9/2013 | Penninger et al. |

OTHER PUBLICATIONS

Dworkin, Pharmacologic management of neuropathic pain: Evidence-based recommendations, Pain, 2007, 132, pp. 237-251.*

* cited by examiner

[Figure 1]
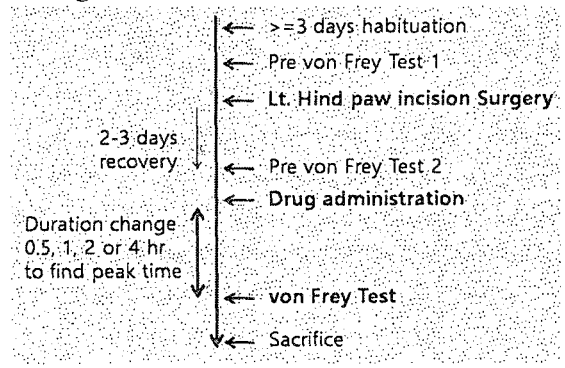
[Figure 2]
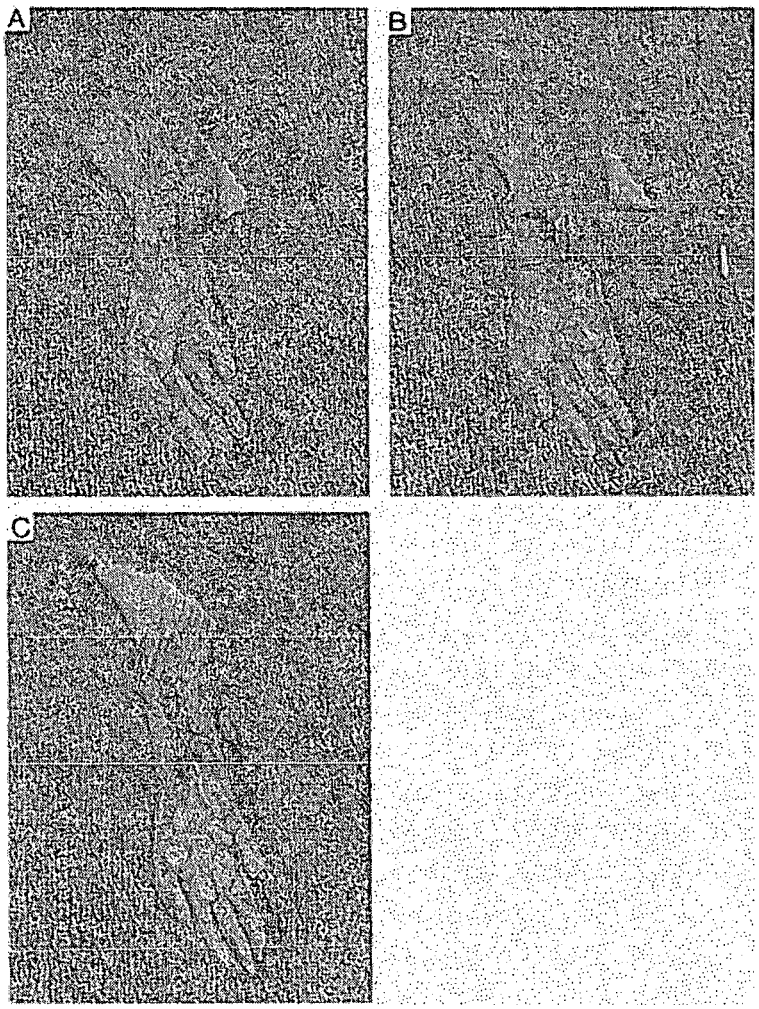

SULFAMATE DERIVATIVE COMPOUNDS FOR USE IN TREATING OR ALLEVIATING PAIN

This application is the US national phase under 35 U.S.C. § 371 of international application PCT/KR2014/012260, filed Dec. 12, 2014, which claims priority to U.S. Provisional Application No. 61/915,042 filed Dec. 12, 2013.

TECHNICAL FIELD

The present invention relates to sulfamate derivative compounds and a composition for treating and/or alleviating pain containing the sulfamate derivative compounds or a pharmaceutically acceptable salt thereof as an active ingredient. More specifically, the present invention relates to a pharmaceutical composition for treating or alleviating pain containing a sulfamate derivative compound and/or a pharmaceutically acceptable salt thereof as an active ingredient. Furthermore, the present invention relates to a method for treatment or alleviation of pain comprising administering a sulfamate derivative compound in a pharmaceutically effective amount to a subject in need of treatment or alleviation of pain.

BACKGROUND ART

Pain is one of the most common reasons for a patient to seek medical care and in consequence, pain results in a tremendous number of lost work days per year.

Pain is an unpleasant feeling often caused by intense or damaging stimuli, such as stubbing a toe, burning a finger, putting alcohol on a cut, and bumping the funny bone. The International Association for the Study of Pain's widely used definition states: "Pain is an unpleasant sensory and emotional experience associated with actual or potential tissue damage, or described in terms of such damage". Pain motivates the individual to withdraw from damaging situations, to protect a damaged body part while it heals, and to avoid similar experiences in the future. Most pain resolves promptly once the painful stimulus is removed and the body has healed, but sometimes pain persists despite removal of the stimulus and apparent healing of the body; and sometimes pain arises in the absence of any detectable stimulus, damage or disease.

Pain is the most common reason for physician consultation. It is a major symptom in many medical conditions, and can significantly interfere with a person's quality of life and general functioning. Psychological factors such as social support, hypnotic suggestion, excitement, or distraction can significantly modulate pain's intensity or unpleasantness.

In 1994, responding to the need for a more useful system for describing chronic pain, the International Association for the Study of Pain (IASP) classified pain according to specific characteristics: (1) region of the body involved (e.g., abdomen, lower limbs), (2) system whose dysfunction may be causing the pain (e.g., nervous, gastrointestinal), (3) duration and pattern of occurrence, (4) intensity and time since onset, and (5) etiology.

This system has been criticized by Clifford J. Woolf and others as inadequate for guiding research and treatment. According to Woolf, there are three classes of pain: nociceptive pain (see hereunder), inflammatory pain which is associated with tissue damage and the infiltration of immune cells, and pathological pain which is a disease state caused by damage to the nervous system or by its abnormal function (dysfunctional pain, irritable bowel syndrome, tension type headache, etc.).

In nociceptive pain, the stimulation of the sensory nerve endings called nociceptors causes the sensation of pain. Such pain often occurs after injury or surgery. The pain signals are transmitted by the nociceptors to the brain. Often the pain is localised, constant and has an aching or throbbing quality. Once the damage to the tissue heals the pain usually resolves. Treatment with opioids may resolve nociceptive pain. Psychogenic pain is a pain disorder that is associated with psychological factors. Some types of mental or emotional problems can cause pain. They can also increase or prolong pain. Stomach pains is one of the most common types of psychogenic pain. People with this pain disorder actually have real pain. The diagnosis is made when all physical causes of pain are ruled out.

Neuropathic pain is caused by abnormalities in the nerves, spinal cord or brain and is a chronic type of non-malignant pain with an estimated prevalence of over 1% of the population. Optimizing pain relief in these patients is crucial in helping a patient regain control of his or her life. The most common cause of neuropathic pain is injury or dysfunction of nerves. Injury or dysfunction of peripheral nerves or nerves descending from the spinal cord results in disinhibition of nerve impulses at the spinal cord which in consequence results in pain. Neuropathic pain can also be centrally mediated, rather than peripheral, in conditions such as spinal cord injury and multiple sclerosis.

Neuropathic pain can therefore be divided into two further classes; peripheral neuropathic pain and central neuropathic pain depending on whether the peripheral or central nervous system is affected.

Inadequate treatment of pain is widespread throughout surgical wards, intensive care units, accident and emergency departments, in general practice, in the management of all forms of chronic pain and in end of life care. This neglect is extended to all ages, from neonates to the frail elderly. African and Hispanic Americans are more likely than others to suffer needlessly in the hands of a physician; and women's pain is more likely to be undertreated than men's.

Therefore, it is needed to develop therapeutic measures for treating or alleviating pain.

DISCLOSURE

Technical Problem

Inadequate treatment of pain is widespread throughout surgical wards, intensive care units, accident and emergency departments, in general practice, in the management of all forms of chronic pain and in end of life care. This neglect is extended to all ages, from neonates to the frail elderly. African and Hispanic Americans are more likely than others to suffer needlessly in the hands of a physician; and women's pain is more likely to be undertreated than men's.

Technical Solution

The present invention relates to sulfamate derivative compounds and a composition for treating and/or alleviating pain containing the sulfamate derivative compounds or a pharmaceutically acceptable salt thereof as an active ingredient.

Advantageous Effects the present invention relates to a pharmaceutical composition for treating or alleviating pain containing a sulfamate derivative compound and/or a pharmaceutically acceptable salt thereof as an active ingredient. Furthermore, the present invention relates to a method for treatment or alleviation of pain comprising administering a sulfamate derivative compound in a pharmaceutically effective amount to a subject in need of treatment or alleviation of pain.

BEST MODE

The present inventor has done intensive studies to develop a novel anti-pain drug with excellent activity and low toxicity which may be an effective treatment or alleviation for pain. As a result, the present inventors have discovered that the sulfamate derivative compounds represented by the below formula 1 provide highly enhanced anti-pain activity with significantly decreased side effects.

Accordingly, it is an object of this invention to provide a novel sulfamate derivative compound or a pharmaceutically acceptable salt thereof.

Another object of this invention to provide a pharmaceutical composition for treating or alleviating pain containing the sulfamate derivative compound and/or the pharmaceutically acceptable salt thereof as an active ingredient.

A further object of this invention to provide a method for treatment or alleviation of pain comprising administering a sulfamate derivative compound in a pharmaceutically effective amount to a subject in need of treatment or alleviation of pain.

MODE FOR INVENTION

In one aspect of this invention, there is provided a compound represented by the following formula 1 or a pharmaceutically acceptable salt thereof:

[Chemical Formula 1]

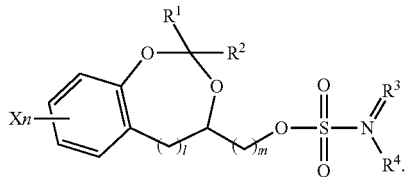

wherein X is selected from the group consisting of hydrogen, hydroxyl, $C_1$-$C_5$ alkoxy, $C_1$-$C_5$ alkyl, $C_2$-$C_5$ alkenyl, $C_6$-$C_{10}$ aryl, $C_1$-$C_5$ alkoxycarbonyl, carboxyl, $C_2$-$C_5$ acyl, $C_1$-$C_5$ alkylthio, cyano, nitro, amine, $C_1$-$C_5$ alkylamine and halogen; $R^1$ and $R^2$ are each independently selected from the group consisting of hydrogen, $C_1$-$C_5$ alkyl group, $C_2$-$C_5$ alkenyl and $C_6$-$C_{10}$ aryl group, or $R_1$ and $R_2$ together with the carbon atom to which they attach form a $C_3$-$C_{12}$ cycloalkyl group; $R^3$ and $R^4$ are each independently hydrogen or $C_2$-$C_3$ alkyl; and l, m and n are each independently an integer of 0 to 4.

According to a preferred embodiment of the present invention, when X is H, OMe, Cl, F, or I, n is an integer from 1-4.

According to a concrete embodiment, l or m are each independently an integer 0 or 1.

In a preferred embodiment according to the invention, $R^1$ and $R^2$ are each independently methyl, ethyl or isopropyl, or $R^1$ and $R^2$ together with the carbon atom to which they attach form a cyclopentyl or a cyclohexyl group.

According to a concrete embodiment, $R^3$ and $R^4$ are each independently hydrogen or methyl.

According to a concrete embodiment, X is chlorine, fluorine, iodine, bromine or H; n is an integer from 1-4; $R^1$ and $R^2$ are each dependently selected from the group consisting of methyl, ethyl and isopropyl, or $R_1$ and $R_2$ together with the carbon atom to which they attach form a cyclopentyl or a cyclohexyl ring; $R^3$ and $R^4$ are each dependently selected from the group consisting of H, methyl, ethyl, and isopropyl; l and m are each dependently an integer from 0, 1 or 2.

The term "alkyl" as used herein, refers to a linear or branched chain of a saturated hydrocarbon group, e.g., methyl, ethyl, propyl, butyl, isobutyl, tert-butyl and pentyl. "$C_1$-$C_5$ alkyl group" as used herein, refers to an alkyl group with a carbon number of 1-5.

The term "alkenyl", as used herein, unless otherwise indicated, includes alkyl moieties having at least one carbon-carbon double bond wherein alkyl is as defined above.

The term "alkoxy", as used herein, unless otherwise indicated, includes O-alkyl groups wherein alkyl is as defined above.

The term "alkylthio", as used herein, unless otherwise indicated, includes S-alkyl groups wherein alkyl is as defined above.

The term "alkoxycarbonyl", as used herein, unless otherwise indicated, includes —C(O)O-alkyl groups wherein alkyl is as defined above.

The term "acyl", as used herein, unless otherwise indicated, includes —C(O)-alkyl groups wherein alkyl is as defined above.

The term "aryl" or "aryl group" as used herein, refers to a totally or partially unsaturated monocyclic or polycyclic carbon rings having aromaticity. The aryl group of the present invention is preferably monoaryl or biaryl, such as phenyl or naphthyl. The aryl radical may be optionally substituted by one or more substituents such as hydroxy, mercapto, halo, alkyl, phenyl, alkoxy, haloalkyl, nitro, cyano, dialkylamino, aminoalkyl, acyl and alkoxycarbonyl, as defined herein.

The term "cycloalkyl" or "cycloalkyl group" as used herein, refers to a monocyclic or polycyclic saturated ring comprising carbon and hydrogen atoms.

According to a preferred embodiment of the present invention, the compound is selected from the group consisting of:

((R)-2,2-dimethyl-4H-benzo[d][1,3]dioxin-4-yl)methyl sulfamate;
((S)-2,2-dimethyl-4H-benzo[d][1,3]dioxin-4-yl)methyl sulfamate;
(2,2-dimethyl-4H-benzo[d][1,3]dioxin-4-yl))methyl sulfamate;
((R)-2,2-diethyl-4H-benzo[d][1,3]dioxin-4-yl)methyl sulfamate;
((S)-2,2-diethyl-4H-benzo[d][1,3]dioxin-4-yl)methyl sulfamate;
(2,2-diethyl-4H-benzo[d][1,3]dioxin-4-yl))methyl sulfamate;
((R)-4H-spiro[benzo[d][1,3]dioxine-2,1'-cyclopentan]-4-yl) methyl sulfamate;
((S)-4H-spiro[benzo[d][1,3]dioxine-2,1'-cyclopentan]-4-yl) methyl sulfamate;
(4H-spiro[benzo[d][1,3]dioxine-2,1'-cyclopentan]-4-yl) methyl sulfamate;
((R)-4H-spiro[benzo[d][1,3]dioxine-2,1'-cyclohexan]-4-yl) methyl sulfamate;

((S)-4H-spiro[benzo[d][1,3]dioxine-2,1'-cyclohexan]-4-yl) methyl sulfamate;
(4H-spiro[benzo[d][1,3]dioxine-2,1'-cyclohexan]-4-yl) methyl sulfamate;
2-(2,2-dimethyl-4H-benzo[d][1,3]dioxin-4-yl)ethyl sulfamate;
2-(2,2-diethyl-4H-benzo[d][1,3]dioxin-4-yl)ethyl sulfamate;
2-(4H-spiro[benzo[d][1,3]dioxine-2,1'-cyclopentan]-4-yl) ethyl sulfamate;
2-(4H-spiro[benzo[d][1,3]dioxine-2,1'-cyclohexan]-4-yl) ethyl sulfamate;
(2,2-dimethyl-4,5-dihydrobenzo[d][1,3]dioxepin-4-yl) methyl sulfamate;
(2,2-diethyl-4,5-dihydrobenzo[d][1,3]dioxepin-4-yl)methyl sulfamate;
(4,5-dihydrospiro[benzo[d][1,3]dioxepine-2,1'-cyclopentan]-4-yl)methyl sulfamate;
(4,5-dihydrospiro[benzo[d][1,3]dioxepine-2,1'-cyclohexan]-4-yl)methyl sulfamate;
2-(2,2-dimethyl-4,5-dihydrobenzo[d][1,3]dioxepin-4-yl) ethyl sulfamate;
2-(2,2-diethyl-4,5-dihydrobenzo[d][1,3]dioxepin-4-yl)ethyl sulfamate;
2-(4,5-dihydrospiro[benzo[d][1,3]dioxepine-2,1'-cyclopentan]-4-yl)ethyl sulfamate;
2-(4,5-dihydrospiro[benzo[d][1,3]dioxepine-2,1'-cyclohexan]-4-yl)ethyl sulfamate;
((R)-8-chloro-2,2-dimethyl-4K-benzo[d][1,3]dioxin-4-yl) methyl sulfamate;
((S)-8-chloro-2,2-dimethyl-4H-benzo[d][1,3]dioxin-4-yl) methyl sulfamate;
(8-chloro-2,2-dimethyl-4H-benzo[d][1,3]dioxin-4-yl) methyl sulfamate;
((R)-8-chloro-2,2-diethyl-4H-benzo[d][1,3]dioxin-4-yl) methyl sulfamate;
((S)-8-chloro-2,2-diethyl-4H-benzo[d][1,3]dioxin-4-yl) methyl sulfamate;
(8-chloro-2,2-diethyl-4H-benzo[d][1,3]dioxin-4-yl)methyl sulfamate;
((R)-8-chloro-4H-spiro[benzo[d][1,3]dioxine-2,1'-cyclopentan]-4-yl)methyl sulfamate;
((S)-8-chloro-4H-spiro[benzo[d][1,3]dioxine-2,1'-cyclopentan]-4-yl)methyl sulfamate;
(8-chloro-4H-spiro[benzo[d][1,3]dioxine2,1'-cyclopentan]-4-yl)methyl sulfamate;
((R)-8-chloro-4H-spiro[benzo[d][1,3]dioxine-2,1'-cyclohexan]-4-yl)methyl sulfamate;
((S)-8-chloro-4H-spiro[benzo[d][13]dioxine-2,1'-cyclohexan]-4-yl)methyl sulfamate;
(8-chloro-4H-spiro[benzo[d][1,3]dioxine-2,1'-cyclohexan]-4-yl)methyl sulfamate;
2-(8-chloro-2,2-dimethyl-4H-benzo[d][1,3]dioxin-4-yl) ethyl sulfamate;
2-(8-chloro-2,2-diethyl-4H-benzo[d][1,3]dioxin-4-yl)ethyl sulfamate;
2-(8-chloro-4H-spiro[benzo[c][1,3]dioxine-2,1'-cyclopentan]-4-yl)ethyl sulfamate;
2-(9-chloro-4H-spiro[benzo[d][1,3]dioxine-2,1'-cyclohexan]-4-yl)ethyl sulfamate;
2-(9-chloro-2,2-dimethyl-4,5-dihydrobenzo[d][1,3]dioxepin-4-yl)ethyl sulfamate;
2-(9-chloro-2,2-diethyl-4,5-dihydrobenzo[d][1,3]dioxepin-4-yl)ethyl sulfamate;
2-(9-chloro-4,5-dihydrospiro[benzo[d][1,3]dioxepine-2,1'-cyclopentan]-4-yl)ethyl sulfamate;
2-(9-chloro-4,5-dihydrospiro[benzo[d][1,3]dioxepine-2,1'-cyclohexan]-4-yl)ethyl sulfamate;
(7-chloro-2,2-dimethyl-4H-benzo[c][1,3]dioxin-4-yl) methyl sulfamate;
((R)-6-chloro-2,2-dimethyl-4H-benzo[d][1,3]dioxin-4-yl) methyl sulfamate;
((S)-6-chloro-2,2-dimethyl-4H-benzo[d][1,3]dioxin-4-yl) methyl sulfamate;
(6-chloro-2,2-dimethyl-4H-benzo[d][1,3]dioxin-4-yl) methyl sulfamate;
((R)-6-chloro-2,2-diethyl-4H-benzo[d][1,3]dioxin-4-yl) methyl sulfamate;
((S)-6-chloro-2,2-diethyl-4H-benzo[d][1,3]dioxin-4-yl) methyl sulfamate;
(6-chloro-2,2-diethyl-4H-benzo[d][1,3]dioxin-4-yl)methyl sulfamate;
(6-chloro-4H-spiro[benzo[d][1,3]dioxine-2,1'-cyclopentan]-4-yl)methyl sulfamate;
(6-chloro-4H-spiro[benzo[d][1,3]dioxine-2,1'-cyclohexan]-4-yl)methyl sulfamate;
(6-fluoro-2,2-dimethyl-4H-benzo[d][1,3]dioxin-4-yl)methyl sulfamate;
2-(6-fluoro-2,2-dimethyl-4H-benzo[d][1,3]dioxin-4-yl) ethyl sulfamate;
(7-fluoro-2,2-dimethyl-4,5-dihydrobenzo[d][1,3]dioxepin-4-yl)methyl sulfamate;
(6-methoxy-2,2-dimethyl-4H-benzo[d][1,3]dioxin-4-yl) methyl sulfamate;
Sodium (R)-(((2,2-dimethyl-4H-benzo[d][1,3]dioxin-4-yl) methoxy)sulfonyl)amide Trihydrate;
Sodium (S)-(((2,2-dimethyl-4H-benzo[d][1,3]dioxin-4-yl) methoxy)sulfonyl)amide Trihydrate;
Sodium (((2,2-dimethyl-4H-benzo[d][1,3]dioxin-4-yl) methoxy)sulfonyl)amide Trihydrate;
Sodium (R)-(((6-chloro-2,2-dimethyl-4H-benzo[d][1,3]dioxin-4-yl)methoxy)sulfonyl)amide;
Sodium (S)-(((6-chloro-2,2-dimethyl-4H-benzo[d][1,3]dioxin-4-yl)methoxy)sulfonyl)amide;
Sodium (((6-chloro-2,2-dimethyl-4H-benzo[d][1,3]dioxin-4-yl)methoxy)sulfonyl)amide;
Sodium (R)-(((4H-spiro[benzo[d][1,3]dioxine-2,1'-cyclopentan]-4-yl)methoxy)sulfonyl)amide;
Sodium (S)-(((4H-spiro[benzo[d][1,3]dioxine-2,1'-cyclopentan]-4-yl)methoxy)sulfonyl)amide;
Sodium (((4H-spiro[benzo[d][1,3]dioxine-2,1'-cyclopentan]-4-yl)methoxy)sulfonyl)amide;
Sodium ((6-chloro-(4H-spiro[benzo[c][1,3]dioxine-2,1'-cyclopentan]-4-yl)methoxy)sulfonyl)amide;
Sodium ((2-(2,2-dimethyl-4H-benzo[d][1,3]dioxin-4-yl) ethoxy)sulfonyl)amide;
Sodium ((2-(4H-spiro[benzo[d][1,3]dioxine2,1'-cyclopentan]-4-yl)ethoxy)sulfonyl)amide;
Potassium (R)-(((2,2-dimethyl-4H-benzo[d][1,3]dioxin-4-yl)methoxy)sulfonyl)amide;
Potassium (S)-(((2,2-dimethyl-4H-benzo[d][1,3]dioxin-4-yl)methoxy)sulfonyl)amide;
Potassium (((2,2-dimethyl-4H-benzo[d][1,3]dioxin-4-yl) methoxy)sulfonyl)amide; and
Lithium (S)-(((2,2-dimethyl-4H-benzo[d][1,3]dioxin-4-yl) methoxy)sulfonyl)amide.

According to a concrete embodiment, the compound is in the form of a racemate, an enantiomer, a diastereomer, a mixture of enantiomers or a mixture of diastereomers.

As seen in the Examples, the present inventors have synthesized the compounds of various stereochemistries, and investigated their relief pain activity by multilateral experiments.

The term "enantiomer" as used herein, refers to one of two stereoisomers that are mirror images of each other which are non-superimposable due to the existence of one or more chiral carbons. According to a concrete embodiment, the enantiomer of the present invention is one in which chiral carbons of $C_4$ and $C_5$ are diverse in stereo-configuration.

The term "diastereomer" as used herein, refers to stereoisomers that are not enantiomers, which occurs when two or more stereoisomers of a compound have different configurations at one or more (but not all) of the equivalent chiral centers and thus are not mirror images of each other.

The term "racemate" as used herein, refers to one that amounts of two enantiomers of different stereo-configuration, and lack in optical activity.

It would be obvious to the skilled artisan from the Examples below that the compounds of this invention are not limited to those with specific stereochemistry.

According to a concrete embodiment, the pharmaceutically acceptable salt is produced by reacting the compound with an inorganic acid, an organic acid, an amino acid, sulfonic acid, an alkali metal or ammonium ion.

The pharmaceutically acceptable salts of the present invention are those which can be manufactured by using a method known in the art, for example, but not limited to, salts with inorganic acids such as hydrochloric acid, bromic acid, sulfuric acid, sodium hydrogen sulfate, phosphate, nitrate and carbonate; and salts with organic acids such as formic acid, acetic acid, propionic acid, oxalic acid, succinic acid, benzoic acid, citric acid, maleic acid, malonic acid, tartaric acid, gluconic acid, lactic acid, gestisic acid, fumaric acid, lactobionic acid, salicylic acid, trifluoroacetic acid and acetylsalicylic acid (aspirin); or salts with amino acids such as glycine, alanine, valine, isoleucine, serine, cysteine, cystine, aspartic acid, glutamine, lysine, arginine, tyrosine, and proline; salts with sulfonic acid such as methane sulfonate, ethane sulfonate, benzene sulfonate and toluene sulfonate; metal salts by reaction with an alkali metal such as sodium, lithium and potassium; or salts with ammonium ion.

In another aspect of this invention, there is provided a method for the treatment or alleviation of pain comprising administering a pharmaceutically effective amount of the compound of the present invention or the pharmaceutically acceptable salt thereof to a subject in need thereof.

The term "pharmaceutically effective amount" as used herein, refers to an amount enough to show and accomplish efficacies and activities for preventing, alleviating, or treating a disease associated with pain.

The pharmaceutical composition of this invention includes a pharmaceutically acceptable carrier besides the active ingredient compound. The pharmaceutically acceptable carrier contained in the pharmaceutical composition of the present invention, which is commonly used in pharmaceutical formulations but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in Remington's Pharmaceutical Sciences (19th ed., 1995).

The pharmaceutical composition according to the present invention may be administered orally or parenterally, and concretely, administered parenterally. For parenteral administration, it may be administered intravenously, subcutaneously, intramuscularly, intraperitoneally, transdermally or intra-articularly. More concretely, it is administered intramuscularly or intraperitoneally.

The compound or the pharmaceutically acceptable salt thereof according to the pain is one or more selected from the group consisting of nociceptive pain, psychogenic pain, inflammatory pain, and pathological pain. More concretely, the pain is one or more selected from the group consisting of neuropathic pain, cancer pain, postoperative pain, trigeminal neuralgia pain, idiopathic pain, diabetic neuropathic pain, and migraine.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, pharmaceutical composition of the present invention may be administered with a daily dosage of 0.001-10000 mg/kg (body weight).

According to the conventional techniques known to those skilled in the art, the pharmaceutical composition according to the present invention may be formulated with a pharmaceutically acceptable carrier and/or vehicle as described above, finally providing several forms including a unit close form and a multi-dose form. Non-limiting examples of the formulations include, but not limited to, a solution, a suspension or an emulsion in oil or aqueous medium, an elixir, a powder, a granule, a tablet and a capsule, and may further comprise a dispersion agent or a stabilizer.

The sulfamate derivative compound of the present invention may be prepared by the following reaction scheme.

[Reaction scheme 1-1] Synthesis of alcohol compound (l = 0 or 1, m = 0)

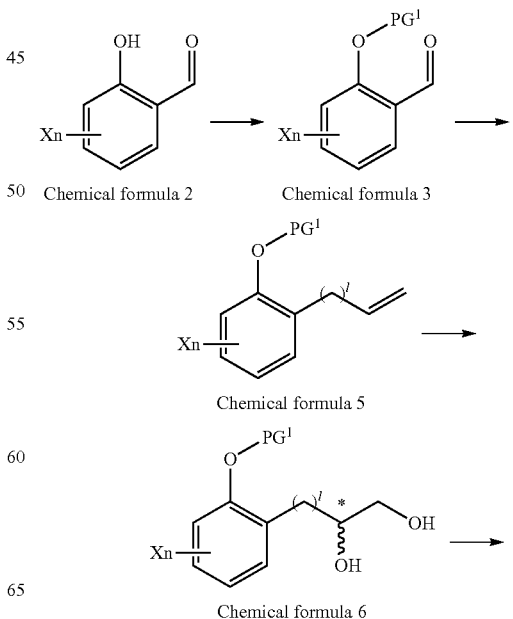

Chemical formula 2    Chemical formula 3

Chemical formula 5

Chemical formula 6

-continued

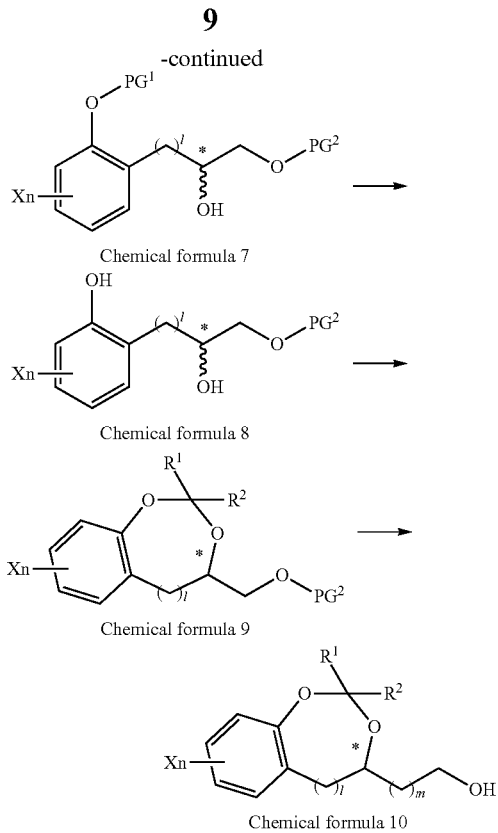

Chemical formula 7

Chemical formula 8

Chemical formula 9

Chemical formula 10

[Reaction scheme 2] Synthesis of protected aldehyde compound.

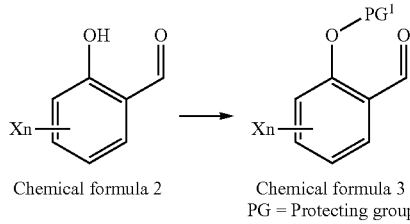

Chemical formula 2

Chemical formula 3
PG = Protecting group

OH of a phenol compound of formula 2 is protected by a protecting group, including but not limited to, Bn (benxyl), Tityl (Triphenylmethyl), Acetyl, Benzoyl, Piv (Pivaloyl), MOM (Methoxymethyl), TMS (Trimethyl silyl), TES (Triethyl silyl), TIPS (Triisopropyl silyl), TBDMS (tert-butyldimethyl silyl), TBDPS (tert-butyldiphenyl silyl) and so on.

[Reaction scheme 3] Synthesis of protected vinyl compound

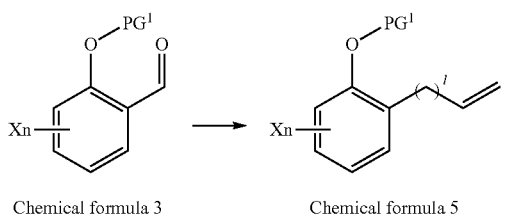

Chemical formula 3

Chemical formula 5

A protected vinyl compound of formula 5 is synthesized by Wittig reaction using a protected aldehyde compound of formula 3 with a Wittig salt, including but not limited to, ethyltriphenyl phosphonium bromide.

[Reaction scheme 4] Synthesis of protected diol compound

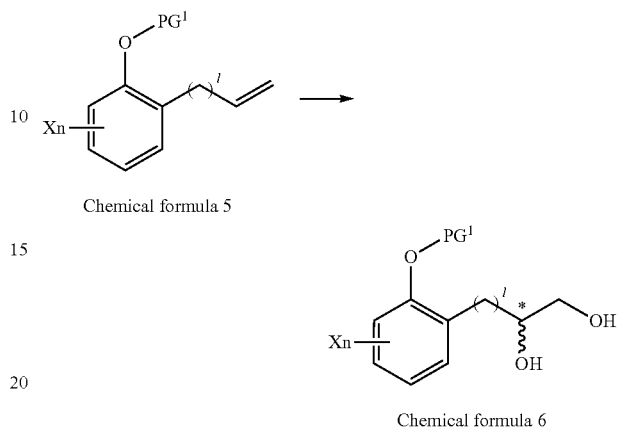

Chemical formula 5

Chemical formula 6

The asymmetric dihydroxylation catalyst may be one or more selected from the group consisting of a chiral ligand (e.g., $(DHQD)_2PHAL$, $(DHQ)_2PHAL$, etc.), an osmium catalyst (e.g., $OsO_4$, $K_2OsO_2(OH)_4$, etc.), $K_2CO_3$, $K_3Fe(CN)_6$, N-methylmorpholine oxide (NMO), methane sulfone amide ($CH_3SO_2NH_2$), and the like. For example, the asymmetric dihydroxylation catalyst may include, but are not limited to, AD-mix-α ($K_2OsO_2(OH)_4$(cat), $K_2CO_3$, $K_3Fe(CN)_6$, $(DHQ)_2PHAL$(cat)) and methane sulfone amide ($CH_3SO_2NH_2$), or $OsO_4$ and N-methylmorpholine oxide (NMO).

[Reaction scheme 5] Synthesis of protected alcohol compound

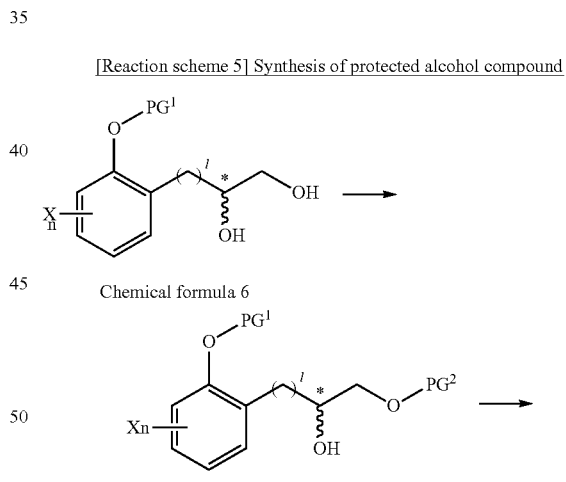

Chemical formula 6

Chemical formula 7

Chemical formula 8

A primary alcohol group of the two OH group of a diol compound of formula 6 is protected by a protecting group, including but not limited to, Piv (Pivaloyl), TBDMS (tert-butyldimethyl silyl), TBDPS (tert-butyldiphenyl silyl), Bn (benxyl), Tityl (Triphenylmethyl), Acetyl, Benzoyl, Piv (Pivaloyl), and MOM (Methoxymethyl) to produce the compound of formula 7, followed by removing PG$^1$ using hydrogenation to afford the compound of formula 8.

[Reaction scheme 6] Synthesis of protected dioxolan alcohol compound

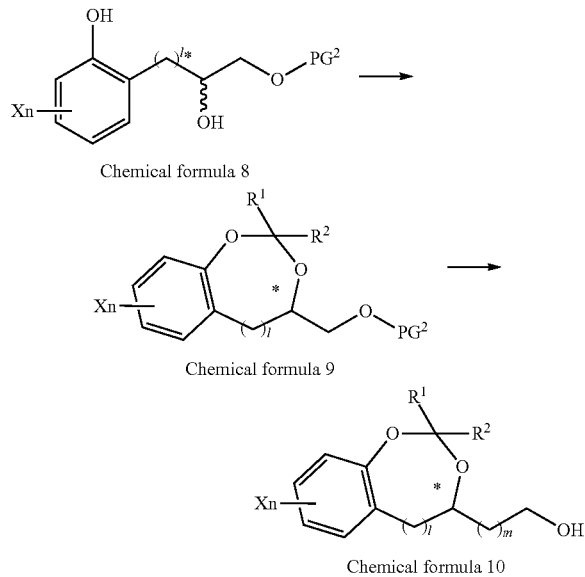

Chemical formula 8

Chemical formula 9

Chemical formula 10

A compound of formula 8 is reacted with a ketone compound (such as acetone, 3-pentanone, cyclopentanone, or cyclohexanone), an alkoxy compound (such as dimethoxymethane, dimethoxypropan, diethoxyethane, or methoxy propene, (E)-3-methoxypent-2-ene, 1-methoxycyclopent-1-ene, 1-methoxycyclohex-1-ene), or an aldehyde compound (such as benzaldyde, cyclopentanecarboxaldehyde, or cyclohexaecarboxaldehyde) in an acidic condition, for example, a solution dissolved with an acid such as p-TsOH (p-toluenesulfonic acid), $H_2SO_4$(Sulfuric acid), $HNO_3$(Nitric acid), followed by removing a protecting group PG$^2$ to afford the dioxolan alcohol compound of formula 10. But while we have described several examples of the ketone compound, the alkoxy compound, the aldehyde compound and the acid for the above reaction, it is not limited thereto and may be appropriately selected depending on the intended purpose.

[Reaction scheme 1-2] Synthesis of alcohol compound (l = 0 or 1, m = 1)

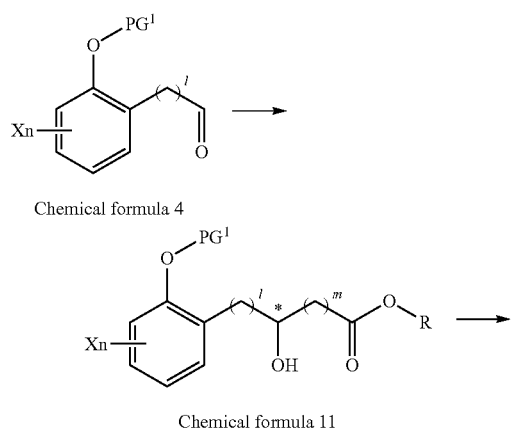

Chemical formula 4

Chemical formula 11

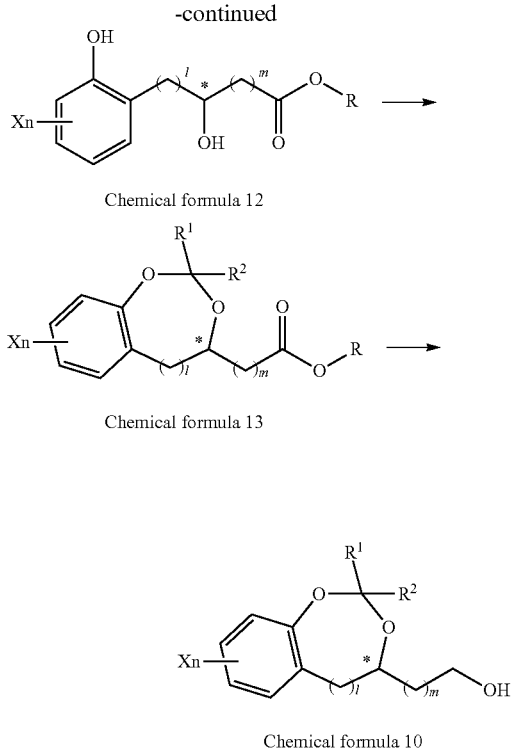

Chemical formula 12

Chemical formula 13

Chemical formula 10

[Reaction scheme 7] Synthesis of ester alcohol compound

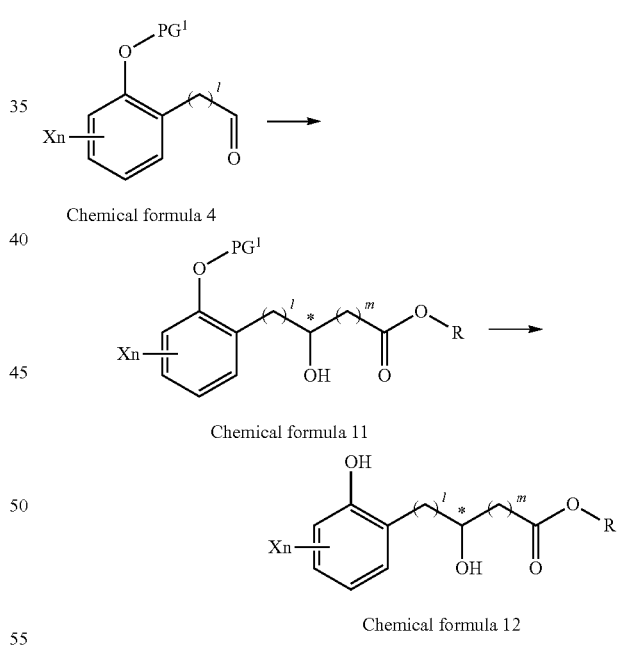

Chemical formula 4

Chemical formula 11

Chemical formula 12

An alkyl ester compound, such as ethyl acetate, methyl acetate, propyl acetate, or benzyl acetate is reacted with a compound of formula 4 in basic condition using a base such as LDA (Lithiumdiisopropyl amide), n-BuLi (n-butyllithium), or t-BuOK (Potassium tert-butoxide), followed by removing a protecting group PG$^1$ to afford the compound of formula 12. But while we have described several examples of the base and the alkyl ester compound for the above reaction, it is not limited thereto and may be appropriately selected depending on the intended purpose.

[Reaction scheme 8] Synthesis of dioxolan ester compound

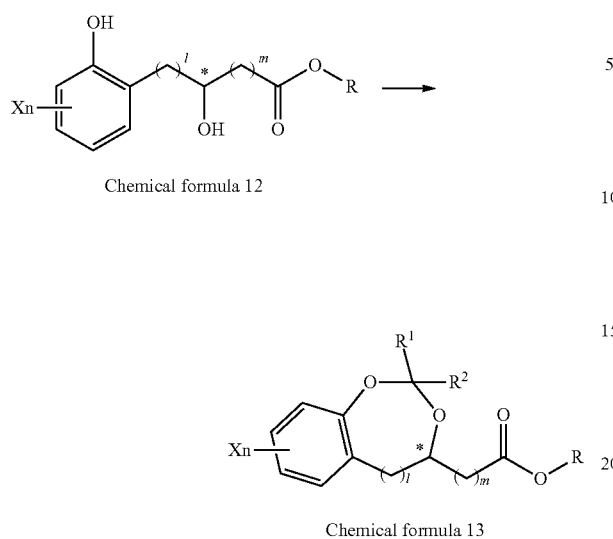

Chemical formula 12

Chemical formula 13

A compound of formula 12 is reacted with a ketone compound (such as acetone, 3-pentanone, cyclopentanone, or cyclohexanone), or an alkoxy compound (such as dimethoxymetane, dimethoxypropan, diethoxyethane, or methoxy propene, (E)-3-methoxypent-2-ene, 1-methoxycyclopent-1-ene, 1-methoxycyclohex-1-ene) in an acidic condition using an acid such as p-TsOH (p-toluenesulfonic acid), $H_2SO_4$(Sulfuric acid), $HNO_3$(Nitric acid), to produce the dioxolan ester compound of formula 13. But while we have described several examples of the ketone compound, the alkoxy compound, the aldehyde compound and the acid for the above reaction, it is not limited thereto and may be appropriately selected depending on the intended purpose.

[Reaction scheme 9] Synthesis of dioxolan alcohol compound

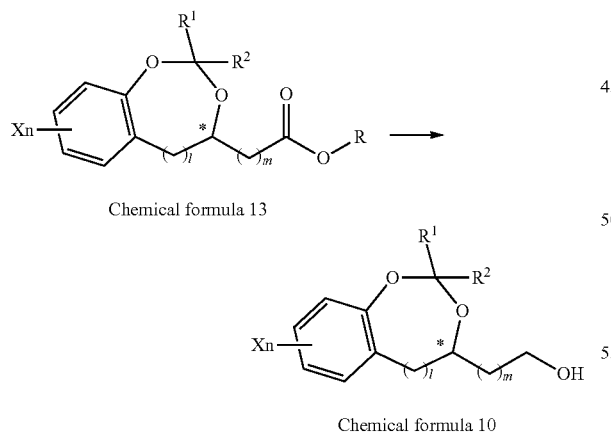

Chemical formula 13

Chemical formula 10

A dioxolan alcohol compound of formula 10 is synthesized by a reduction reaction from a compound formula 13 in a basic condition using a base, including but not limited to, $LiAlH_4$(Lithium aluminum hydride), $NaBH_4$(Sodium borohydride), $Zn(BH_4)_2$ (Zincborohydride), NaH (Sodium hydride), KH (Potassium hydride), $AlH_3$ (Aluminum hydride), or NaOMe (Sodiummethoxyde).

[Reaction scheme 1-3] Synthesis of alcohol compound (l = 0, m = 0)

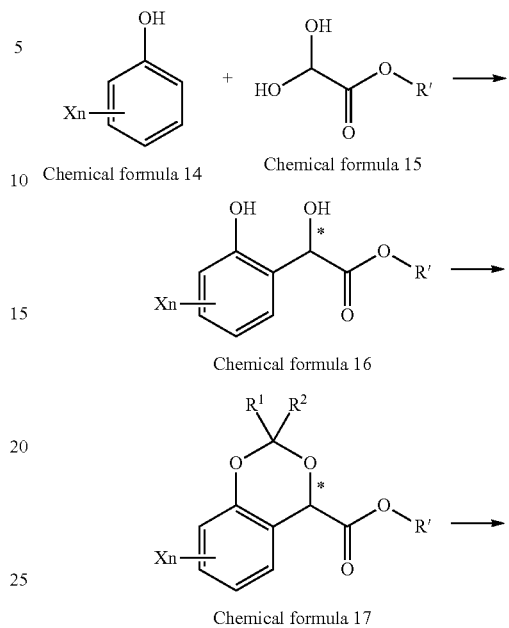

Chemical formula 14     Chemical formula 15

Chemical formula 16

Chemical formula 17

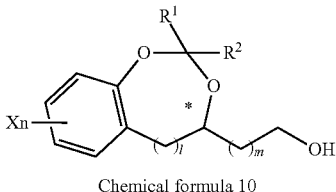

Chemical formula 10

[Reaction scheme 10] Synthesis of alcohol ester compound

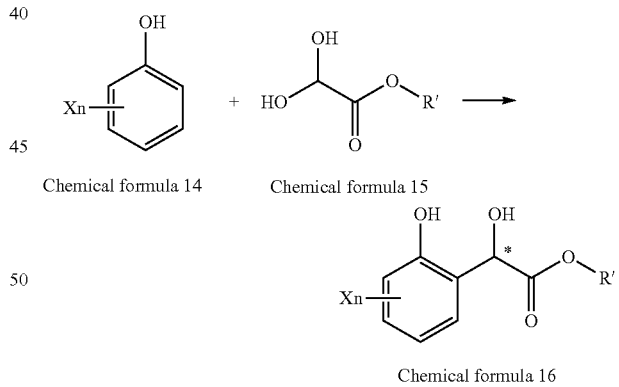

Chemical formula 14     Chemical formula 15

Chemical formula 16

An alcohol ester compound of formula 16 is synthesized by a reaction using a phenol of formula 14 with an alkyl-dihydroacetate (alkyl glyoxylate, such as (1R)-(−)-mentyl glyoxylate, (1S)-(+)-mentyl glyoxylate, ethyl glyoxylate) compound of formula 15 in an acidic condition using a Lewis acid, such as $TiCl_4$, $SnCl_4$, $ZnCl_4$, $AlCl_3$, or $BF_3$ diethyl etherate. But while we have described several examples of the Lewis acid and the alkyldihydroacetate (alkyl glyoxylate) compound for the above reaction, it is not limited thereto and may be appropriately selected depending on the intended purpose.

[Reaction scheme 11] Synthesis of dioxolan ester compound

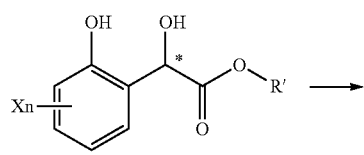

Chemical formula 16

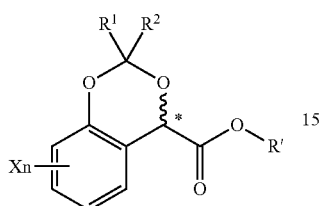

Chemical formula 17

A compound of formula 16 is reacted with a ketone compound (such as acetone, 3-pentanone, cyclopentanone, or cyclohexanone), or an alkoxy compound (such as dimethoxymetane, dimethoxypropan, diethoxyethane, or methoxy propene, (E)-3-methoxypent-2-ene, 1-methoxycyclopent-1-ene, 1-methoxycyclohex-1-ene) in an acidic condition using an acid such as p-TsOH (p-toluenesulfonic acid), $H_2SO_4$(Sulfuric acid), $HNO_3$(Nitric acid), to produce the dioxolan ester compound of formula 17. But while we have described several examples of the ketone compound, the alkoxy compound, the aldehyde compound and the acid for the above reaction, it is not limited thereto and may be appropriately selected depending on the intended purpose.

[Reaction scheme 12] Synthesis of dioxolan alcohol compound

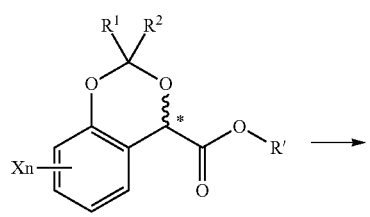

Chemical formula 17

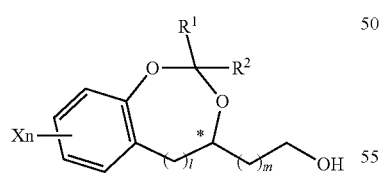

Chemical formula 10

A dioxolan alcohol compound of formula 10 is synthesized by a reduction reaction from a compound of formula 17 in a basic condition using a reducing agent, including but not limited to, $LiAlH_4$(Lithium aluminum hydride), $NaBH_4$ (Sodium borohydride), $Zn(BH_4)_2$ (Zincborohydride), NaH (Sodium hydride), KH (Potassium hydride), $AlH_3$ (Aluminum hydride), NaOMe (Sodiummethoxyde).

[Reaction scheme 13] Synthesis of sulfamate compound

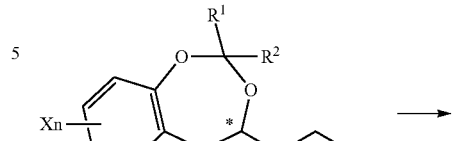

Chemical formula 10

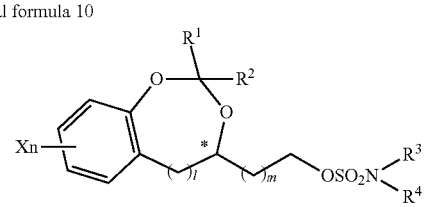

Chemical formula 1

A sulfamate compound of formula 1 is synthesized by a reaction from a compound of formula 10 using a sulfamoylation reagent, including but not limited to, sulfamoyl chloride synthesized from CSI (chlorosulfonyl isocyanate) and formic acid, and Boc-sulfonyl chloride synthesized from CSI and t-BuOH (tert-butyl alcohol).

Preparation Example 1:
1-allyl-2-(benzyloxy)benzene

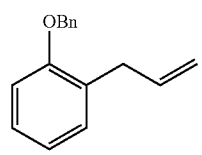 [SMILES: C=CCc1ccccc1OCc1ccccc1]

To a stirred solution of 2-allylphenol (15 g, 111.8 mmol) in acetonitrile (100 mL) was added benzylbromide (14.6 mL, 122.9 mmol) and $K_2CO_3$ (30.9 g, 223.6 mmol) at room temperature sequentially. The mixture was heated to reflux then stirred for 4 hr. The resulting mixture was cooled to room temperature, filtered through celite, and concentrated under reduced pressure. The crude compound was purified by a silica gel column to produce the title compound (34.7 g, 85~90%).
$^1$H NMR (400 MHz, $CDCl_3$) δ 3.50 (s, 2H), 5.10 (s, 4H), 6.02~6.09 (m, 1H), 6.96 (s, 2H), 7.21 (s, 2H), 7.37~7.48 (m, 5H)

Preparation Example 2:
3-(2-(benzyloxy)phenyl)propane-1,2-diol

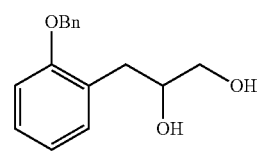 [SMILES: OCC(O)Cc1ccccc1OCc1ccccc1]

A 1000 mL round bottomed flask equipped with a magnetic stirrer was charged with 250 mL of tert-butyl alcohol, 250 mL of water, K$_3$Fe(CN)$_6$ (88 g, 267.49 mmol), K$_2$CO$_3$ (36.9 g, 267.49 mmol), (DHQ)$_2$-PHAL (0.70 g, 0.89 mmol), K$_2$OsO$_2$(OH)$_4$ (66 mg, 0.18 mmol), and methanesulfonamide (8.5 g, 89.17 mmol). The mixture was cooled to 0° C. 1-Allyl-2-(benzyloxy)benzene (Preparation example 1, 20 g, 89.17 mmol) was added at once and the heterogeneous slurry was stirred at 0° C. for overnight. The reaction was quenched by solid Na$_2$SO$_3$ (56 g, 445.8 mmol). Ethyl acetate was added to the reaction mixture, and after separation of the layers, the aqueous phase was further extracted with ethyl acetate. The combined organic layers were washed with 2N KOH and brine, dried over anhydrous MgSO$_4$, filtered and concentrated under reduced pressure. The crude compound was purified by a silica gel column to produce the title compound (3.3 g, 75~90%).

$^1$H NMR (400 MHz, CDCl$_3$) δ 2.07~2.12 (m, 2H), 2.42 (s, 1H), 2.77~2.97 (m, 2H), 3.50~3.61 (m, 2H), 3.97 (s, 1H), 5.11 (s, 1H), 6.98 (s, 2H), 7.22~7.27 (m, 2H), 7.38~7.44 (m, 5H)

Preparation Example 3:
3-(2-(benzyloxy)phenyl)-2-hydroxypropyl pivalate

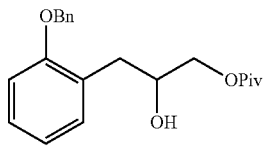

To a stirred solution of 3-(2-(benzyloxy)phenyl)propane-1,2-diol (Preparation example 2, 10.8 g, 41.81 mmol) in pyridine (100 mL) was added trimethylacetyl chloride (6.1 ml, 35.1 mmol) at 0° C. The mixture was stirred for 1 hr. The resulting mixture was diluted with EtOAc, washed with water, dried over anhydrous MgSO$_4$, filtered and concentrated under reduced pressure. The crude compound was purified by a silica gel column to produce the title compound (11.9 g, 75~90%)

$^1$H NMR (400 MHz, CDCl$_3$) δ 1.19 (s, 9H), 2.38 (d, J=4.0, 1H), 2.86~2.97 (m, 2H), 4.03 (s, 1H), 4.08~4.15 (m, 2H), 5.09 (s, 2H), 6.91~6.95 (m, 2H), 7.18~7.23 (m, 2H), 7.31~7.43 (m, 5H)

Preparation Example 4:
2-hydroxy-3-(2-hydroxyphenyl)propyl pivalate

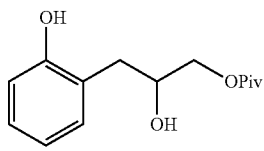

To a stirred solution of 3-(2-(benzyloxy)phenyl)-2-hydroxypropyl pivalate (Preparation example 3, 11.9 g 34.75 mmol) in ethyl acetate (100 mL) was added Pd(OH)$_2$ (2.97 g, 0.25 w/w) at room temperature and then hydrogen gas was installed. The mixture was stirred for 2 hr. The resulting mixture was filtered through celite and concentrated under reduced pressure. The crude compound was purified by a silica gel column to produce the title compound (8.7, 80~99%)

$^1$H NMR (400 MHz, CDCl$_3$) δ 1.29 (s, 9H), 2.85~2.95 (m, 2H), 3.39 (s, 1H), 4.02~4.07 (m, 1H), 4.31~4.40 (m, 2H), 6.86 (t, J=8.0, 1H), 7.05 (d, J=8.0, 1H), 7.18 (t, J=8.0, 1H), 7.94 (d, J=8.0, 1H), 7.95 (s, 1H)

Preparation Example 5: (2,2-dimethyl-4,5-dihydrobenzo[d][1,3]dioxepin-4-yl)methyl pivalate

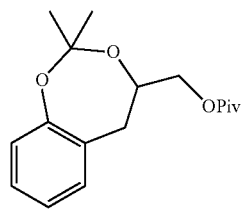

To a stirred solution of 2-hydroxy-3-(2-hydroxyphenyl)propyl pivalate (Preparation example 4, 5.0 g, 19.89 mmol) in dichloromethane (50 mL) was added 2-methoxypropene (3.79 mL, 39.79 mmol) and pyridinium p-toluenesulfonate (0.56 g, 1.98 mmol) at room temperature then stirred for overnight. The resulting mixture was diluted with dichloromethane, washed with water, dried over anhydrous MgSO$_4$, filtered and concentrated under reduced pressure. The crude compound was purified by a silica gel column to produce the title compound (5.7 g, 75~99%)

$^1$H NMR (400 MHz, CDCl$_3$) δ 1.25 (s, 9H), 1.47 (s, 6H), 2.81~2.92 (m, 1H), 3.00~3.09 (m, 1H), 4.06~4.20 (m, 2H), 4.42~4.68 (m, 1H), 6.92 (d, J=8.0, 1H), 7.04~7.11 (m, 2H), 7.17 (t, J=8.0, 1H)

Preparation Example 6: (2,2-dimethyl-4,5-dihydrobenzo[d][1,3]dioxepin-4-yl)methanol

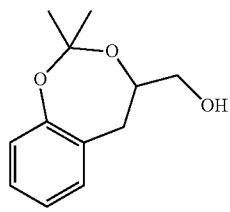

To a stirred solution of (2,2-dimethyl-4,5-dihydrobenzo[d][1,3]dioxepin-4-yl)methyl pivalate (Preparation example 5, 5.75 g, 19.66 mmol) in MeOH (50 mL) was add sodium methoxide (3.52 g, 59.00 mmol) at room temperature. The mixture was warmed to 30~40° C. then stirred for 5 hr. The resulting mixture was diluted with ethyl acetate, washed with water, dried over anhydrous MgSO$_4$, filtered and concentrated under reduced pressure. The crude compound was purified by a silica gel column to produce the title compound (3.9 g, 75~99%)

$^1$H NMR (400 MHz, CDCl$_3$) δ 1.48 (s, 3H), 1.53 (s, 3H), 2.02~2.06 (m, 1H), 2.84~2.91 (m, 2H), 3.58~3.70 (m, 2H), 4.07~4.31 (m, 1H), 6.93 (d, J=8.0, 1H), 7.03~7.11 (m, 2H), 7.17 (dt, J=8.0, 4.0, 1H)

Preparation Example 7: (2,2-diethyl-4,5-dihydrobenzo[d][1,3]dioxepin-4-yl)methyl pivalate

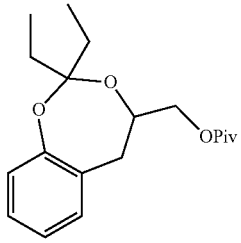

To a stirred solution of 2-hydroxy-3-(2-hydroxyphenyl)propyl pivalate (Preparation example 4, 1.7 g, 6.7 mmol) in dichloromethane (20 mL) was added (E)-3-methoxypent-2-ene (6.0 g, 61.1 mmol) and pyridinium p-toluenesulfonate (0.19 g, 0.67 mmol) at room temperature then stirred for overnight. The resulting mixture was diluted with dichloromethane, washed with water, dried over anhydrous MgSO$_4$, filtered and concentrated under reduced pressure. The crude compound was purified by a silica gel column to produce the title compound (1.4 g, 60~80%)

$^1$H NMR (400 MHz, CDCl$_3$) δ 1.25 (s, 9H), 1.58~1.91 (m, 9H), 2.85~3.17 (m, 2H), 3.32 (s, 1H), 4.13 (t, J=8.0, 2H), 6.92~6.94 (m, 1H), 7.00~7.06 (m, 1H), 7.08~7.11 (m, 2H), 7.14~7.19 (m, 1H)

Preparation Example 8: (2,2-diethyl-4,5-dihydrobenzo[d][1,3]dioxepin-4-yl)methanol

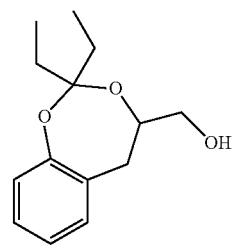 [SMILES: CCC1(CC)Oc2ccccc2CC(CO)O1]

The substantially same method as described in Preparation example 6 was conducted, except that (2,2-diethyl-4,5-dihydrobenzo[d][1,3]dioxepin-4-yl)methyl pivalate obtained in Preparation example 7 was used instead of (2,2-dimethyl-4,5-dihydrobenzo[d][1,3]dioxepin-4-yl)methyl pivalate (Preparation example 5), to obtain the title compound (0.99 g, 39%)

1H NMR (400 MHz, CDCl$_3$) δ 1.08~1.92 (m, 6H) 1.93~1.65 (m, 4H) 2.19~2.03 (m, 1H) 2.79~2.64 (m, 1H) 2.93~2.82 (m, 1H) 3.63~3.41 (m, 2H) 4.18~4.12 (m, 1H) 6.94~6.92 (m, 1H) 7.05~7.01 (m, 1H) 7.10~7.08 (m, 1H) 7.16 (t, J=6.0, 1H)

Preparation Example 9: (4,5-dihydrospiro[benzo[d][1,3]dioxepine-2,1'-cyclopentane]-4-yl)methyl pivalate

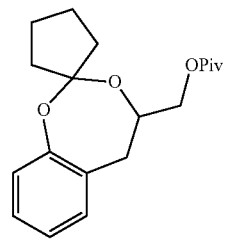

The substantially same method as described in Preparation example 7 was conducted, except that 1-methoxycyclopent-1-ene was used instead (E)-3-methoxypent-2-ene, to obtain the title compound (1.9 g, 50~70%)

1H NMR (400 MHz, CDCl$_3$) δ 1.89~1.68 (s, 9H) 2.12~2.03 (m, 8H) 2.89~2.84 (m, 1H) 3.02~2.98 (m, 1H) 4.15~4.10 (m, 2H) 4.23~4.18 (m, 1H) 6.94~6.92 (m, 1H) 7.06~7.02 (m, 1H) 7.10 (S, 1H) 7.19~7.15 (m, 1H)

Preparation Example 10: (4,5-dihydrospiro[benzo[d][1,3]dioxepine-2,1'-cyclopentane]-4-yl)methanol

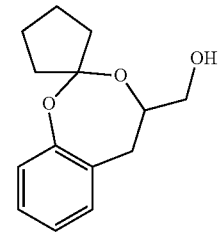 [SMILES: OCC1Cc2ccccc2OC2(CCCC2)O1]

The substantially same method as described in Preparation example 6 was conducted, except that (4,5-dihydrospiro[benzo[d][1,3]dioxepine-2,1'-cyclopentane]-4-yl)methyl pivalate obtained in Preparation example 9 was used instead of (2,2-dimethyl-4,5-dihydrobenzo[d][1,3]dioxepin-4-yl)methyl pivalate (Preparation example 5), to obtain the title compound (0.68 g, 47%)

1H NMR (400 MHz, CDCl$_3$) δ 1.95~1.66 (m, 7H) 2.13~2.04 (m, 1H) 2.74 (d, J=2, 1H) 3.53~3.24 (m, 1H) 3.88~3.85 (m, 2H) 4.06~4.00 (m, 1H) 6.94 (dd, J=8.0, 1H) 7.05 (dt, J=7, 3, 1H) 7.15~7.10 (m, 1H) 7.21 (dt, J=12, 3, 1H)

Preparation Example 11: (4,5-dihydrospiro[benzo[d][1,3]dioxepine-2,1'-cyclohexane]-4-yl)methyl pivalate

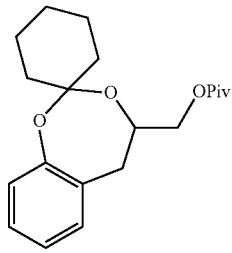

The substantially same method as described in Preparation example 7 was conducted, except that 1-methoxycyclohex-1-ene was used instead (E)-3-methoxypent-2-ene, to obtain the title compound (2.3 g, 50~70%)

1H NMR (400 MHz, CDCl$_3$) δ 1.28 (s, 9H) 1.78~1.40 (m, 10H) 3.14~2.88 (m, 2H) 4.17~4.08 (m, 1H) 4.38~4.32 (m, 1H) 6.96~6.91 (m, 1H) 7.04~7.01 (m, 1H) 7.08 (S, 1H) 7.17~7.15 (m, 1H)

Preparation Example 12: (4,5-dihydrospiro[benzo[d][1,3]dioxepine-2,1'-cyclohexane]-4-yl)methanol

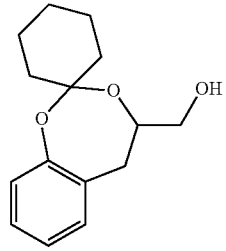 [SMILES: OCC1Cc2ccccc2OC2(CCCCC2)O1]

The substantially same method as described in Preparation example 6 was conducted, except that (4,5-dihydrospiro[benzo[d][1,3]dioxepine-2,1'-cyclohexane]-4-yl)methyl pivalate obtained in Preparation example 11 was used instead of (2,2-dimethyl-4,5-dihydrobenzo[d][1,3]dioxepin-4-yl)methyl pivalate (Preparation example 5), to obtain the title compound (1.1 g, 50~70%)

1H NMR (400 MHz, CDCl$_3$) δ 1.85~1.42 (m, 10H) 2.93~2.69 (m, 1H) 3.11~2.95 (m, 1H) 3.99~3.68 (m, 2H) 4.33~4.18 (m, 1H) 6.94~6.82 (m, 1H) 6.97 (d, J=8.0, 1H) 7.03 (t, J=6.0, 1H) 7.10 (s, 1H) 7.17 (t, J=8.0, 1H)

Preparation Example 13: 2-(Benzyloxy)benzaldehyde

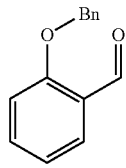

To a stirred solution of salicylaldehyde (8.7 mL, 81.8 mmol) in acetonitrile (80 mL) was added benzylbromide (13.2 mL, 90.07 mmol) and K$_2$CO$_3$ (13.6 g, 98.3 mmol) at room temperature sequentially. The mixture was heated to reflux then stirred for 5 hr. The resulting mixture was cooled to room temperature, filtered through celite, diluted with EtOAc, washed with water, dried over anhydrous MgSO$_4$, filtered and concentrated under reduced pressure. (17.4 g, 80~100%).

1H NMR (400 MHz, CDCl$_3$) δ 5.20 (s, 2H), 7.03~7.06 (m, 2H), 7.33~7.46 (m, 5H), 7.52~7.56 (m, 1H), 7.85~7.88 (m, 1H), 10.5 (d, J=0.40, 1H).

Preparation Example 14: 1-(Benzyloxy)-2-vinylbenzene

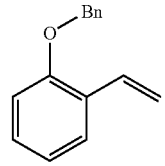 [SMILES: C=Cc1ccccc1OCc1ccccc1]

To a stirred solution of methyltriphenylphosphonium bromide (38 g, 106.4 mmol) in THF (150 mL) was added sodium amide (6.4 g, 163.7 mmol) at room temperature then stirred for 1 hr. 2-(benzyloxy)benzaldehyde (Preparation example 13, 17.39 g, 81.8 mmol) in THF (70 mL) was added then stirred for 1 hr. The resulting mixture was filtered through celite, diluted with n-hexanes, washed with H$_2$O, dried over MgSO$_4$, filtered and concentrated under reduced pressure. (16.9 g, 80~100%).

1H NMR (400 MHz, CDCl$_3$) δ 5.11 (s, 2H), 5.24~5.27 (m, 1H), 5.73~5.78 (m, 1H), 6.91~6.97 (m, 2H), 7.09~7.17 (m, 1H), 7.19~7.23 (m, 1H), 7.31~7.34 (m, 1H), 7.37~7.40 (m, 2H), 7.43~7.45 (m, 2H), 7.45~7.52 (m, 1H).

Preparation Example 15: (R)-1-(2-(benzyloxy)phenyl)ethane-1,2-diol

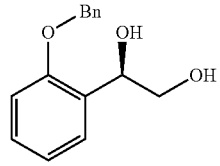 [SMILES: OC[C@H](O)c1ccccc1OCc1ccccc1]

A 1000 mL round bottomed flask equipped with a magnetic stirrer was charged with 250 mL of tert-butyl alcohol, 250 mL of water, K$_3$Fe(CN)$_6$ (56.3 g, 171.0 mmol), K$_2$CO$_3$ (23.7 g, 171.0 mmol), (DHQD)$_2$-PHAL (0.45 g, 0.57 mmol). K$_2$OsO$_2$(OH)$_4$ (42 mg, 0.12 mmol), and methanesulfonamide (5.42 g, 57 mmol). The mixture was cooled to 0° C. 1-(benzyloxy)-2-vinylbenzene (Preparation example 14, 12.0 g, 57.0 mmol) was added at once and the heterogeneous slurry was stirred at 0° C. for overnight. The reaction was quenched by solid Na$_2$SO$_3$ (69.0 g, 570.0 mmol). Ethyl acetate was added to the reaction mixture, and after separation of the layers, the aqueous phase was further extracted with ethyl acetate. The combined organic layers were washed with 2N KOH and brine, dried over anhydrous MgSO$_4$, filtered and concentrated under reduced pressure.

The crude compound was purified by a silica gel column to produce the title compound (11.7 g, 75~90%).

1H NMR (400 MHz, CDCl₃) δ 2.05~2.09 (m, 1H), 2.84 (d, J=5.6, 1H), 3.68~3.74 (m, 1H), 3.81~3.86 (m, 1H), 5.07~5.13 (m, 3H), 6.95 (d, J=8.0, 1H), 7.00 (t, J=7.4, 1H), 7.24~7.28 (m, 1H), 7.33~7.42 (m, 6H).

Preparation Example 16: (R)-1-(2-(benzyloxy)phenyl)-2-(tert-butyldimethylsilyloxy) ethanol

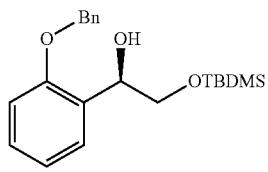 [SMILES: CC(C)(C)[Si](C)(C)OC[C@H](O)c1ccccc1OCc1ccccc1]

To a stirred solution of (R)-1-(2-(benzyloxy)phenyl)ethane-1,2-diol (Preparation example 15, 11.6 g, 47.5 mmol) in dichloromethane (116 mL) was added imidazole (3.9 g, 57.0 mmol) and tert-butyldimethylsilyl chloride (7.9 g, 52.3 mmol) at room temperature then stirred for 1 hr. The resulting mixture was diluted with dichloromethane, washed with H₂O, dried over MgSO₄, filtered and concentrated under reduced pressure. (17.8 g, 80~100%).

¹H NMR (400 MHz, CDCl₃) δ 0.10~0.12 (m, 6H), 0.90~0.95 (m, 9H), 2.06 (q, J=4.1, 1H), 2.84 (d, J=5.6, 1H), 3.68~3.74 (m, 1H), 3.81~3.86 (m, 1H), 5.07~5.14 (m, 3H), 6.94~6.96 (m, 1H), 6.98~7.02 (m, 1H), 7.24~7.28 (m, 1H), 7.32~7.43 (m, 5H).

Preparation Example 17: (R)-2-(2-(tert-butyldimethylsilyloxy)-1-hydroxyethyl)phenol

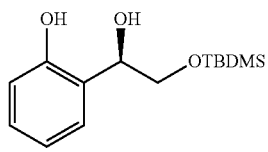 [SMILES: CC(C)(C)[Si](C)(C)OC[C@H](O)c1ccccc1O]

To a stirred solution of (R)-1-(2-(benzyloxy)phenyl)-2-(tert-butyldimethylsilyloxy)ethanol (Preparation example 16, 17.8 g, 47.5 mmol) in EtOH (178 mL) was added Pd/C (10%, 0.89 g) and ammonium formate (9.0 g, 142.5 mmol) at 35° C. then stirred for 1 hr. The resulting mixture was diluted with EtOAc, washed with H₂O, dried over MgSO₄, filtered and concentrated under reduced pressure. The crude compound was purified by a silica gel column to produce to produce the title compound. (10.2 g, 65~85%).

¹H NMR (400 MHz, CDCl₃) δ 0.10~0.12 (m, 6H), 0.90~0.95 (m, 9H), 3.45 (d, J=1.2, 1H), 3.71~3.77 (m, 2H), 4.86~4.89 (m, 1H), 6.85~6.89 (m, 2H), 6.96~6.99 (m, 1H), 7.17~7.21 (m, 1H), 8.35 (s, 1H).

Preparation Example 18: (R)-tert-butyl((2,2-dimethyl-4H-benzo[d][1,3]dioxin-4-yl)methoxy) dimethylsilane

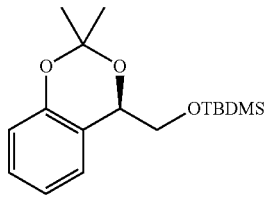 [SMILES: CC1(C)Oc2ccccc2[C@H](CO[Si](C)(C)C(C)(C)C)O1]

To a stirred solution of (R)-2-(2-(tert-butyldimethylsilyloxy)-1-hydroxyethyl)phenol (Preparation example 17, 10.2 g, 37.8 mmol) in DMF (100 mL) was added 2,2-dimethoxypropane (9.3 mL, 75.6 mmol) and p-toluenesulfonic acid (71 mg, 0.4 mmol) at 0° C. sequentially then stirred for 1.5 hr. The resulting mixture was diluted with dichloromethane, washed with H₂O, dried over MgSO₄, filtered and concentrated under reduced pressure. The crude compound was purified by a silica gel column to produce the title compound (9.9 g, 70~90%).

¹H NMR (400 MHz, DMSO) δ=−0.01 (s, 6H), 0.81 (s, 9H), 1.41 (s, 3H), 1.51 (s, 3H), 3.82 (q, J=5.7, 1H), 4.01 (dd, J=3.6, J=11.2, 1H), 4.89 (t, J=4.8, 1H), 6.77 (d, J=8.0, 1H), 6.89 (d, J=7.6, 1H), 7.19~7.15 (m, 1H), 7.27d, J=7.6, 1H).

Preparation Example 19: (R)-(2,2-dimethyl-4H-benzo[d][1,3]dioxin-4-yl)methanol

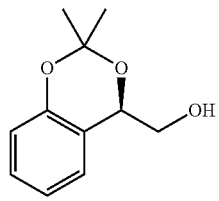

To a stirred solution of (R)-tert-butyl((2,2-dimethyl-4H-benzo[d][1,3]dioxin-4-yl)methoxy)dimethylsilane (Preparation example 18, 6.6 g, 21.3 mmol) in THF (70 mL) was added tetrabutylammonium fluoride hydrate (1M in THF, 25.6 mL, 25.6 mmol) at 0° C. then stirred for 5 hr. The resulting mixture was diluted with EtOAc, washed with H₂O, dried over MgSO₄, filtered and concentrated under reduced pressure. The crude compound was purified by a silica gel column to produce to produce the title compound. (3.7 g, 70~90%).

¹H NMR (400 MHz, CDCl₃) δ 1.50 (s, 3H), 1.62 (s, 3H), 2.12 (t, J=5.8, 1H), 3.78~3.85 (m, 1H), 4.01~4.09 (m, 1H), 4.98~5.01 (m, 1H), 6.82~6.84 (m, 1H), 6.90~6.94 (m, 1H), 7.04 (d, J=7.6, 1H), 7.16~7.21 (m, 1H).

Preparation Example 20: (S)-1-(2-(benzyloxy)phenyl)ethane-1,2-diol

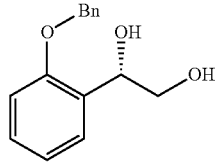 [SMILES: OC[C@@H](O)c1ccccc1OCc1ccccc1]

The substantially same method as described in Preparation example 15 was conducted, except that (DHQ)2PHAL was used instead of (DHQD)2PHAL, to obtain the title compound (21.0 g, 50~70%).

1H NMR (400 MHz, DMSO) δ=3.29 (m, 1H), 3.53 (m, 1H), 4.74 (t, J=6.0, 1H), 5.00 (m, 1H), 5.17 (m, 3H), 6.92~7.02 (m, 2H), 7.17~7.21 (m, 1H), 7.32~7.42 (m, 6H).

Preparation Example 21: (S)-1-(2-(benzyloxy)phenyl)-2-(tert-butyldimethylsilyloxy) ethanol

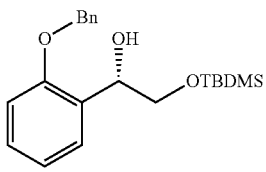

The substantially same method as described in Preparation example 16 was conducted, except that (S)-1-(2-(benzyloxy)phenyl)ethane-1,2-diol obtained in Preparation example 20 was used instead of (R)-1-(2-(benzyloxy)phenyl)ethane-1,2-diol (Preparation example 15), to obtain the title compound (30 g, 75~99%)

1H NMR (400 MHz, DMSO) δ=-0.01 (s, 6H), 0.81 (s, 9H), 3.46 (q, J=6.0, 1H), 3.69 (dd, J=3.4, J=10.2, 1H), 5.00 (m, 1H), 5.10 (m, 3H), 6.97~6.93 (m, 1H), 7.04~7.02 (m, 1H), 7.23~7.19 (m, 1H), 7.48~7.32 (m, 6H).

Preparation Example 22: (S)-2-(2-(tert-butyldimethylsilyloxy)-1-hydroxyethyl)phenol

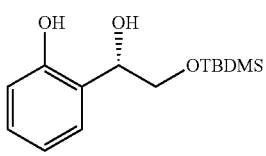 [SMILES: CC(C)(C)[Si](C)(C)OC[C@@H](O)c1ccccc1O]

The substantially same method as described in Preparation example 17 was conducted, except that (S)-1-(2-(benzyloxy)phenyl)-2-(tert-butyldimethylsilyloxy)ethanol obtained in Preparation example 21 was used instead of (R)-1-(2-(benzyloxy)phenyl)-2-(tert-butyldimethylsilyloxy) ethanol (preparation example 16), to obtain the title compound (19.9 g, 75~95%)

1H NMR (400 MHz, DMSO) δ=-0.01 (s, 6H), 0.81 (s, 9H), 3.48~3.38 (m, 1H), 3.68 (dd, J=3.2, J=10.4, 1H), 4.87 (q, J=3.33, 1H), 5.03 (dd, J=2.8, J=7.6, 1H), 6.70~6.79 (m, 2H), 6.96~7.06 (m, 1H), 7.27~7.31 (m, 1H), 9.37 (s, 1H).

Preparation Example 23: (S)-tert-butyl((2,2-dimethyl-4H-benzo[d][1,3]dioxin-4-yl)methoxy)dimethylsilane

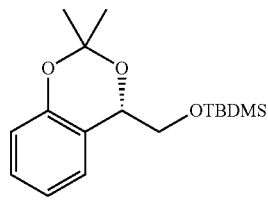 [SMILES: CC1(C)Oc2ccccc2[C@@H](CO[Si](C)(C)C(C)(C)C)O1]

The substantially same method as described in Preparation example 18 was conducted, except that (S)-2-(2-(tert-butyldimethylsilyloxy)-1-hydroxyethyl)phenol obtained in Preparation example 22 was used instead of (R)-2-(2-(tert-butyldimethylsilyloxy)-1-hydroxyethyl)phenol (Preparation example 17), to obtain the title compound (18.0 g, 80%)

1H NMR (400 MHz, DMSO) δ=-0.01 (s, 6H), 0.81 (s, 9H), 1.41 (s, 3H), 1.51 (s, 3H), 3.82 (q, J=5.7, 1H), 4.01 (dd, J=3.6, 11.2, 1H), 4.89 (t, J=4.8, 1H), 6.77 (d, J=8.0, 1H), 6.89 (d, J=7.6, 1H), 7.19~7.15 (m, 1H), 7.27 (d, J=7.6, 1H).

Preparation Example 24: (S)-(2,2-dimethyl-4H-benzo[d][1,3]dioxin-4-yl)methanol

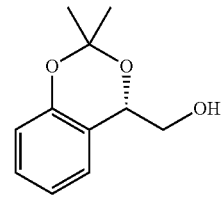

The substantially same method as described in Preparation example 19 was conducted, except that (S)-tert-butyl ((2,2-dimethyl-4H-benzo[d][1,3]dioxin-4-yl) methoxy) dimethylsilane obtained in Preparation example 23 was used instead of (R)-tert-butyl((2,2-dimethyl-4H-benzo[d][1,3]dioxin-4-yl) methoxy)dimethylsilane (Preparation example 18), to obtain the title compound (11.0 g, 80~98%)

1H NMR (400 MHz, DMSO) δ=1.41 (s, 3H), 1.51 (s, 3H), 3.67~3.61 (m, 1H), 3.85~3.80 (m, 1H), 4.87~4.85 (m, 1H), 4.94 (t, J=7.0, 1H), 6.77 (d, J=8.0, 1H), 6.89 (d, J=7.6, 1H), 7.19~7.15 (m, 1H), 7.27 (d, J=7.6, 1H).

Preparation Example 25: 1-(2-(benzyloxy)phenylethane-1,2-diol

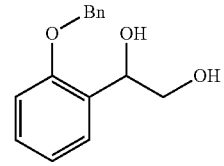 [SMILES: OCC(O)c1ccccc1OCc1ccccc1]

To a stirred solution of 1-(benzyloxy)-2-vinylbenzene (Preparation example 14, 9.0 g) in a 5:1:1 mixture of acetone/tert-butyl alcohol/water was added N-methylmorpholine-N-oxide (7.5 g) and OsO$_4$ (0.54 g) at 0° C. then stirred for 5 hr. The resulting mixture was diluted with EtOAc, washed with H$_2$O, dried over MgSO$_4$, filtered and concentrated under reduced pressure. The crude compound was purified by a silica gel column to produce to produce the title compound (8.3 g, 70~90%).

1H NMR (400 MHz, DMSO) δ=3.29 (m, 1H), 3.53 (m, 1H), 4.74 (t, J=6.0, 1H), 5.00 (m, 1H), 5.17 (m, 3H), 6.92~7.02 (m, 2H), 7.17~7.21 (m, 1H), 7.32~7.42 (m, 6H).

Preparation Example 26: 1-(2-(benzyloxy)phenyl)-2-(tert-butyldimethylsilyloxy) ethanol

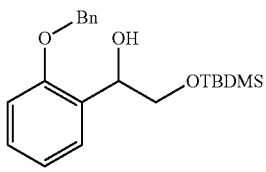 [SMILES: CC(C)(C)[Si](C)(C)OCC(O)c1ccccc1OCc1ccccc1]

The substantially same method as described in Preparation example 16 was conducted, except that 1-(2-(benzyloxy)phenyl)ethane-1,2-diol obtained in Preparation example 25 was used instead of (R)-1-(2-(benzyloxy)phenyl)ethane-1,2-diol (Preparation example 15), to obtain the title compound (5.3 g, 75~99%)

1H NMR (400 MHz, DMSO) δ=-0.01 (s, 6H), 0.81 (s, 9H), 3.46 (q, J=6.0, 1H), 3.69 (dd, J=3.4, 10.2, 1H), 5.00 (m, 1H), 5.10 (m, 3H), 6.97~6.93 (m, 1H), 7.04~7.02 (m, 1H), 7.23~7.19 (m, 1H), 7.48~7.32 (m, 6H).

Preparation Example 27: 2-(2-(tert-butyldimethylsilyloxy)-1-hydroxyethyl)phenol

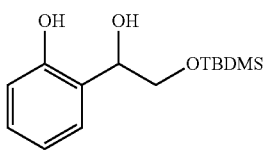 [SMILES: CC(C)(C)[Si](C)(C)OCC(O)c1ccccc1O]

The substantially same method as described in Preparation example 17 was conducted, except that 1-(2-(benzyloxy)phenyl)ethane-1,2-diol obtained in Preparation example 26 was used instead of (R)-1-(2-(benzyloxy)phenyl)-2-(tert-butyldimethylsilyloxy) ethanol (preparation example 16), to obtain the title compound (4.1 g, 75~95%)

1H NMR (400 MHz, DMSO) δ=-0.01 (s, 6H), 0.81 (s, 9H), 3.48~3.38 (m, 1H), 3.68 (dd, J=3.2, 10.4, 1H), 4.87 (q, J=3.33, 1H), 5.03 (dd, J=2.8, J=7.6, 1H), 6.70~6.79 (m, 2H), 6.96~7.06 (m, 1H), 7.27~7.31 (m, 1H), 9.37 (s, 1H).

Preparation Example 28: tert-butyl((2,2-dimethyl-4H-benzo[d][1,3]dioxin-4-yl) methoxy) dimethylsilane

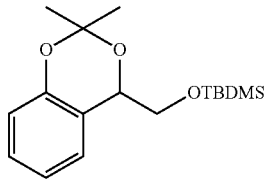 [SMILES: CC1(C)Oc2ccccc2C(CO[Si](C)(C)C(C)(C)C)O1]

The substantially same method as described in Preparation example 18 was conducted, except that 2-(2-(tert-butyldimethylsilyloxy)-1-hydroxyethyl)phenol obtained in Preparation example 27 was used instead of (R)-2-(2-(tert-butyldimethylsilyloxy)-1-hydroxyethyl)phenol (Preparation example 17), to obtain the title compound (4.3 g, 70~90%)

1H NMR (400 MHz, DMSO) δ=-0.01 (s, 6H), 0.81 (s, 9H), 1.41 (s, 3H), 1.51 (s, 3H), 3.82 (q, J=5.7, 1H), 4.01 (dd, J=3.6, 11.2, 1H), 4.89 (t, J=4.8, 1H), 6.77 (d, J=8.0, 1H), 6.89 (d, J=7.6, 1H), 7.19~7.15 (m, 1H), 7.27d, J=7.6, 1H).

Preparation Example 29: (2,2-dimethyl-4H-benzo[d][1,3]dioxin-4-yl)methanol

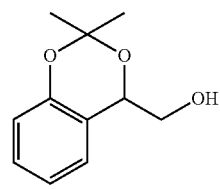

The substantially same method as described in Preparation example 19 was conducted, except that tert-butyl((2,2-dimethyl-4H-benzo[d][1,3]dioxin-4-yl) methoxy) dimethylsilane obtained in Preparation example 28 was used instead of (R)-tert-butyl((2,2-dimethyl-4H-benzo[d][1,3]dioxin-4-yl) methoxy) dimethylsilane (Preparation example 18), to obtain the title compound (3.6 g, 80~98%)

1H NMR (400 MHz. DMSO) δ=1.41 (s, 3H), 1.51 (s, 3H), 3.67~3.61 (m, 1H), 3.85~3.80 (m, 1H), 4.87~4.85 (m, 1H), 4.94 (t, J=7.0, 1H), 6.77 (d, J=8.0, 1H), 6.89 (d, J=7.6, 1H), 7.19~7.15 (m, 1H), 7.27d, J=7.6, 1H).

Preparation Example 30: (R)-tert-butyl((2,2-diethyl-4H-benzo[d][1,3]dioxin-4-yl)methoxy)dimethylsilane

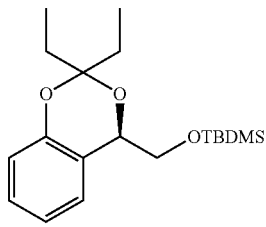 [SMILES: CCC1(CC)Oc2ccccc2[C@H](CO[Si](C)(C)C(C)(C)C)O1]

The substantially same method as described in Preparation example 18 was conducted, except that 3-methoxypent-2-ene was used instead of dimethoxymethane, to obtain the title compound (3.6 g, 50~70%)

1H NMR (400 MHz, DMSO) δ=−0.01 (s, 6H), 0.81 (s, 9H), 0.90 (s, 6H), 1.84 (m, 4H), 3.82 (q, J=5.7, 1H), 4.01 (dd, J=3.6, 11.2, 1H), 4.89 (t, J=4.8, 1H), 6.77 (d, J=8.0, 1H), 6.89 (d, J=7.6, 1H), 7.19~7.15 (m, 1H), 7.27 (d, J=7.6, 1H).

Preparation Example 31: (R)-(2,2-diethyl-4H-benzo[d][1,3]dioxin-4-yl)methanol

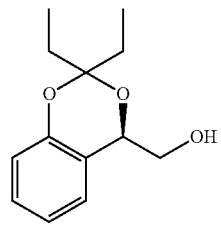 [SMILES: CCC1(CC)Oc2ccccc2[C@H](CO)O1]

The substantially same method as described in Preparation example 19 was conducted, except that (R)-tert-butyl ((2,2-diethyl-4H-benzo[d][1,3]dioxin-4-yl)methoxy)dimethylsilane obtained in Preparation example 30, was used instead of (R)-tert-butyl((2,2-dimethyl-4H-benzo[d][1,3]dioxin-4-yl)methoxy)dimethylsilane (Preparation example 18), to obtain the title compound (1.87 g, 80~98%)

$^1$H NMR (400 MHz, CDCl$_3$) δ 0.93 (t, 3H), 1.05 (t, 3H), 1.80~1.92 (m, 4H), 2.11 (dd, J=5.2, 8.0, 1H), 3.80~3.86 (m, 1H), 3.98~4.06 (m, 1H), 4.97 (dd, J=2.8, 6.4, 111), 6.87 (dd, J=1.0, 8.2, 1H), 6.93 (m, 1H), 7.03 (m, 1H), 7.19 (m, 1H).

Preparation Example 32: (S)-tert-butyl((2,2-diethyl-4H-benzo[d][1,3]dioxin-4-yl)methoxy)dimethylsilane

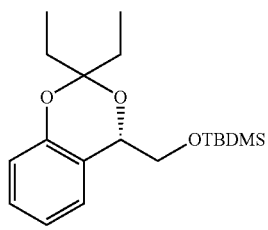 [SMILES: CCC1(CC)Oc2ccccc2[C@@H](CO[Si](C)(C)C(C)(C)C)O1]

The substantially same method as described in Preparation example 30 was conducted, except that (S)-2-(2-(tert-butyldimethylsilyloxy)-1-hydroxyethyl)phenol obtained in Preparation example 22 was used instead of (R)-2-(2-(tert-butyldimethylsilyloxy)-1-hydroxyethyl)phenol (Preparation example 17), to obtain the title compound (1.2 g, 50~70%)

1H NMR (400 MHz, DMSO) δ=−0.01 (s, 6H), 0.81 (s, 9H), 0.90 (s, 6H), 1.84 (m, 4H), 3.82 (q, J=5.7, 1H), 4.01 (dd, J=3.6, J=11.2, 1H), 4.89 (t, J=4.8, 1H), 6.77 (d, J=8.0, 1H), 6.89 (d, J=7.6, 1H), 7.19~7.15 (m, 1H), 7.27 (d, J=7.6, 1H).

Preparation Example 33: (S)-(2,2-diethyl-4H-benzo[d][1,3]dioxin-4-yl)methanol

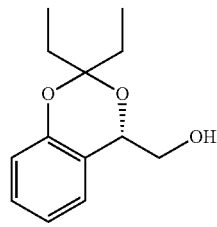 [SMILES: CCC1(CC)Oc2ccccc2[C@@H](CO)O1]

The substantially same method as described in Preparation example 19 was conducted, except that (S)-tert-butyl ((2,2-diethyl-4H-benzo[d][1,3]dioxin-4-yl)methoxy)dimethylsilane obtained in Preparation example 32 was used instead of (R)-tert-butyl((2,2-dimethyl-4H-benzo[d][1,3]dioxin-4-yl) methoxy) dimethylsilane (Preparation example 18), to obtain the title compound (0.8 g, 80~98%)

1H NMR (400 MHz, CDCl$_3$): δ=0.93 (t, 3H), 1.05 (t, 3H), 1.80~1.92 (m, 4H), 2.11 (dd, J=5.2, 8.0 OH), 3.80~3.86 (m, 1H), 3.98~4.06 (m, 1H), 4.97 (dd, J=2.8, 6.4 1H), 6.87 (dd, J=1.0, 8.2, 1H), 6.93 (m, 1H), 7.03 (m, 1H), 7.19 (m, 1H).

Preparation Example 34: tert-butyl((2,2-diethyl-4H-benzo[d][1,3]dioxin-4-yl)methoxy)dimethylsilane

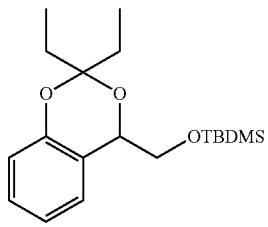

The substantially same method as described in Preparation example 30 was conducted, except that 2-(2-(tert-butyldimethylsilyloxy)-1-hydroxyethyl)phenol obtained in Preparation example 27 was used instead of (S)-2-(2-(tert-butyldimethylsilyloxy)-1-hydroxyethyl)phenol (Preparation example 22), to obtain the title compound (2.1 g, 50~70%)

1H NMR (400 MHz, DMSO) δ=−0.01 (s, 6H), 0.81 (s, 9H), 0.90 (s, 6H), 1.84 (m, 4H), 3.82 (q, J=5.7, 1H), 4.01 (dd, J=3.6, 11.2, 1H), 4.89 (t, J=4.8, 1H), 6.77 (d, J=8.0, 1H), 6.89 (d, J=7.6, 1H), 7.19~7.15 (m, 1H), 7.27 (d, J=7.6, 1H).

Preparation Example 35: (2,2-diethyl-4H-benzo[d][1,3]dioxin-4-yl)methanol

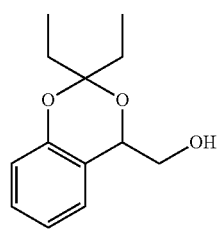 [SMILES: CCC1(CC)Oc2ccccc2C(CO)O1]

The substantially same method as described in Preparation example 19 was conducted, except that tert-butyl((2,2-diethyl-4H-benzo[d][1,3]dioxin-4-yl)methoxy)dimethylsilane obtained in Preparation example 34 was used instead of (R)-tert-butyl((2,2-dimethyl-4H-benzo[d][1,3]dioxin-4-yl) methoxy) dimethylsilane (Preparation example 18), to obtain the title compound (1.7 g, 80~98%)

1H NMR (400 MHz, CDCl$_3$): δ=0.93 (t, 3H), 1.05 (t, 3H), 1.80~1.92 (m, 4H), 2.11 (dd, J=5.2, 8.0 1H), 3.80~3.86 (m, 1H), 3.98~4.06 (m, 1H), 4.97 (dd, J=2.8, 6.4 1H), 6.87 (dd, J=1.0, 8.2, 1H), 6.93 (m, 1H), 7.03 (m, 1H), 7.19 (m, 1H).

Preparation Example 36: (R)-((4H-spiro[benzo[d][1,3]dioxine-2,1'-cyclopentan]-4-yl)methoxy)(tert-butyl)dimethylsilane

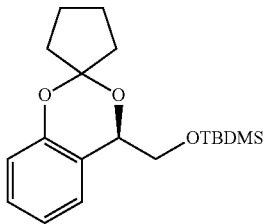 [SMILES: CC(C)(C)[Si](C)(C)OC[C@@H]1OC2(CCCC2)Oc2ccccc21]

The substantially same method as described in Preparation example 30 was conducted, except that cyclopentanone was used instead of pentanone, to obtain the title compound (2.7 g, 50~70%)

1H NMR (400 MHz, DMSO) δ=−0.01 (s, 6H), 0.81 (s, 9H), 1.46~1.56 (m, 4H), 1.90~2.15 (m, 4H), 3.82 (q, J=5.7, 1H), 4.01 (dd, J=3.6, 11.2, 1H), 4.89 (t, J=4.8, 1H), 6.77 (d, J=8.0, 1H), 6.89 (d, J=7.6, 1H), 7.19~7.15 (m, 1H), 7.27 (d, J=7.6, 1H).

Preparation Example 37: (R)-(4H-spiro[benzo[d][1,3]dioxine-2,1'-cyclopentan]-4-yl)methanol

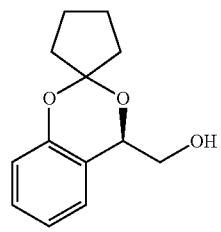 [SMILES: OC[C@@H]1OC2(CCCC2)Oc2ccccc21]

The substantially same method as described in Preparation example 19 was conducted, except that (R)-((4H-spiro[benzo[d][1,3]dioxine2,1'-cyclopentan]-4-yl)methoxy)(tert-butyl)dimethylsilane obtained in Preparation example 36 was used instead of (R)-tert-butyl((2,2-dimethyl-4H-benzo[d][1,3]dioxin-4-yl) methoxy) dimethylsilane (Preparation example 18), to obtain the title compound (1.7 g, 80~98%)

1H NMR (400 MHz, CDCl$_3$): δ=1.46~1.56 (m, 4H), 1.90~2.15 (m, 4H), 3.65 (brs, 1H), 3.82~3.88 (m, 1H), 3.95~4.17 (m, 1H), 5.04 (dd, J=3.0, 6.6, 1H), 6.86 (d, J=0.8 1H), 6.97 (dt, J=1.2, 7.6, 1H), 7.01 (d, J=6, 1H), 7.18~7.26 (m, 1H)

Preparation Example 38: (S)-((4H-spiro[benzo[d][1,3]dioxine-2,1'-cyclopentan]-4-yl)methoxy)(tert-butyl)dimethylsilane

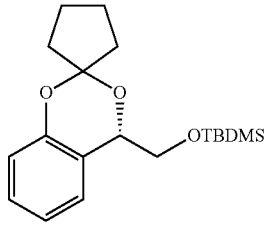 [SMILES: CC(C)(C)[Si](C)(C)OC[C@H]1OC2(CCCC2)Oc2ccccc21]

The substantially same method as described in Preparation example 36 was conducted, except that (S)-2-(2-(tert-butyldimethylsilyloxy)-1-hydroxyethyl)phenol obtained in Preparation example 22 was used instead of (R)-2-(2-(tert-butyldimethylsilyloxy)-1-hydroxyethyl)phenol (Preparation example 17), to obtain the title compound (2.9 g, 50~70%)

1H NMR (400 MHz, DMSO) δ=−0.01 (s, 6H), 0.81 (s, 9H), 1.46~1.56 (m, 4H), 1.90~2.15 (m, 4H), 3.82 (q, J=5.7, 1H), 4.01 (dd, J=3.6, 11.2, 1H), 4.89 (t, J=4.8, 1H), 6.77 (d, J=8.0, 1H), 6.89 (d, J=7.6, 1H), 7.19~7.15 (m, 1H), 7.27 (d, J=7.6, 1H).

Preparation Example 39: (S)-(4H-spiro[benzo[d][1,3]dioxine-2,1'-cyclopentan]-4-yl)methanol

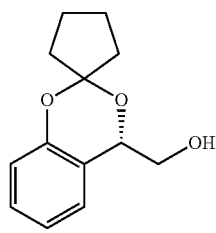 [SMILES: OC[C@H]1OC2(CCCC2)Oc2ccccc21]

The substantially same method as described in Preparation example 19 was conducted, except that (S)-((4H-spiro[benzo[d][1,3]dioxine-2,1'-cyclopentan]-4-yl)methoxy)(tert-butyl)dimethylsilane obtained in Preparation example 38 was used instead of (R)-tert-butyl((2,2-dimethyl-4H-benzo[d][1,3]dioxin-4-yl) methoxy) dimethylsilane (Preparation example 18), to obtain the title compound (1.4 g, 80~98%)

1H NMR (400 MHz, CDCl$_3$): δ=1.46~1.56 (m, 4H), 1.90~2.15 (m, 4H), 3.65 (brs, 1H), 3.82~3.88 (m, 1H), 3.95~4.17 (m, 1H), 5.04 (dd, J=3.0, 6.6, 1H), 6.86 (d, J=0.8 1H), 6.97 (dt, J=1.2, 7.6, 1H), 7.01 (d, J=6.0, 1H), 7.18~7.26 (m, 1H)

Preparation Example 40: ((4H-spiro[benzo[d][1,3]dioxine-2,1'-cyclopentan]-4-yl)methoxy)(tert-butyl)dimethylsilane

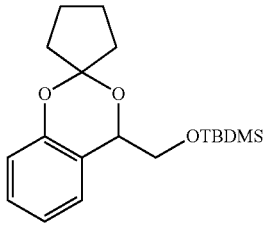 [SMILES: CC(C)(C)[Si](C)(C)OCC1OC2(CCCC2)Oc2ccccc21]

The substantially same method as described in Preparation example 39 was conducted, except that 2-(2-(tert-butyldimethylsilyloxy)-1-hydroxyethyl)phenol obtained in Preparation example 27 was used instead of (S)-2-(2-(tert-butyldimethylsilyloxy)-1-hydroxyethyl)phenol (Preparation example 22), to obtain the title compound (2.1 g, 50~70%)

1H NMR (400 MHz, DMSO) δ=−0.01 (s, 6H), 0.81 (s, 9H), 1.46~1.56 (m, 4H), 1.90~2.15 (m, 4H), 3.82 (q, J=5.7, 1H), 4.01 (dd, J=3.6, 11.2, 1H), 4.89 (t, J=4.8, 1H), 6.77 (d, J=8.0, 1H), 6.89 (d, J=7.6, 1H), 7.19~7.15 (m, 1H), 7.27 (d, J=7.6, 1H).

Preparation Example 41: (4H-spiro[benzo[d][1,3]dioxine-2,1'-cyclopentan]-4-yl)methanol

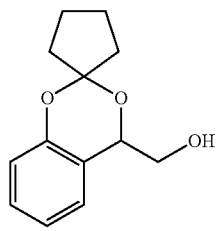 [SMILES: OCC1OC2(CCCC2)Oc2ccccc21]

The substantially same method as described in Preparation example 19 was conducted, except that ((4H-spiro[benzo[d][1,3]dioxine2,1'-cyclopentan]-4-yl)methoxy)(tert-butyl)dimethylsilane obtained in Preparation example 40 was used instead of (R)-tert-butyl((2,2-dimethyl-4H-benzo[d][1,3]dioxin-4-yl) methoxy) dimethylsilane (Preparation example 18), to obtain the title compound (0.8 g, 80~98%)

1H NMR (400 MHz, CDCl$_3$): δ=1.46~1.56 (m, 4H), 1.90~2.15 (m, 4H), 3.65 (brs, 1H), 3.82~3.88 (m, 1H), 3.95~4.17 (m, 1H), 5.04 (dd, J=3.0, 6.6, 1H), 6.86 (d, J=0.8 1H), 6.97 (dt, J=1.2, 7.6 1H), 7.01 (d, J=6, 1H), 7.18~7.26 (m, 1H)

Preparation Example 42: (R)-((4H-spiro[benzo[d][1,3]dioxine-2,1'-cyclohexan]-4-yl)methoxy)(tert-butyl)dimethylsilane

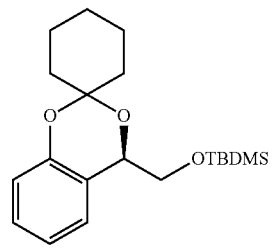 [SMILES: CC(C)(C)[Si](C)(C)OC[C@@H]1OC2(CCCCC2)Oc2ccccc21]

The substantially same method as described in Preparation example 30 was conducted, except that cyclohexanone was used instead of pentanone, to obtain the title compound (2.1 g, 50~70%)

1H NMR (400 MHz, DMSO) δ=−0.01 (s, 6H), 0.81 (s, 9H), 1.47~1.49 (m, 2H), 1.58 (m, 2H), 1.62~1.72 (m, 4H), 1.83 (m, 2H), 4.21 (t, J=4.4, 1H), 4.26 (dd, J=3.6, 11.2, 2H), 6.77 (d, J=8.0, 1H), 6.89 (d, J=7.6, 1H), 7.19~7.15 (m, 1H), 7.27 (d, J=7.6, 1H).

Preparation Example 43: (R)-(4H-spiro[benzo[d][1,3]dioxine-2,1'-cyclohexan]-4-yl)methanol

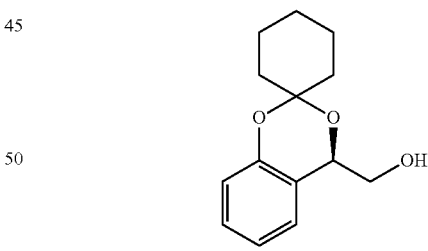

The substantially same method as described in Preparation example 19 was conducted, except that (R)-((4H-spiro[benzo[d][1,3]dioxine2,1'-cyclohexan]-4-yl)methoxy)(tert-butyl)dimethylsilane obtained in Preparation example 42 was used instead of (R)-tert-butyl((2,2-dimethyl-4H-benzo[d][1,3]dioxin-4-yl) methoxy) dimethylsilane (Preparation example 18), to obtain the title compound (1.7 g, 80~98%)

1H NMR (400 MHz, CDCl$_3$): δ=1.49~1.50 (m, 4H), 1.67~1.890 (m, 6H), 2.14 (brs, 1H), 3.79~3.84 (m, 1H), 4.03~4.09 (m, 1H), 4.98 (dd, J=2.8, 6.4 1H), 6.85 (dd, J=0.8, 8.0 1H), 6.915 (dt, J=1.0, 7.4, 1H), 7.02 (d, J=7.2, 1H), 7.16~7.20 (m, 1H)

Preparation Example 44: (S)-((4H-spiro[benzo[d][1,3]dioxine-2,1'-cyclohexan]-4-yl)methoxy)(tert-butyl)dimethylsilane

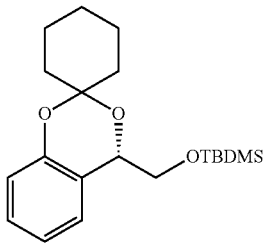 [SMILES: CC(C)(C)[Si](C)(C)OC[C@H]1OC2(CCCCC2)Oc2ccccc21]

The substantially same method as described in Preparation example 42 was conducted, except that (S)-2-(2-(tert-butyldimethylsilyloxy)-1-hydroxyethyl)phenol obtained in Preparation example 22 was used instead of (R)-2-(2-(tert-butyldimethylsilyloxy)-1-hydroxyethyl)phenol (Preparation example 17), to obtain the title compound (2.2 g, 50~70%)

1H NMR (400 MHz, DMSO) δ=−0.01 (s, 6H), 0.81 (s, 9H), 1.47~1.49 (m, 2H), 1.58 (m, 2H), 1.62~1.72 (m, 4H), 1.83 (m, 2H), 4.21 (t, J=4.4, 1H), 4.26 (dd, J=3.6, J=11.2, 2H), 6.77 (d, J=8.0, 1H), 6.89 (d, J=7.6, 1H), 7.19~7.15 (m, 1H), 7.27 (d, J=7.6, 1H).

Preparation Example 45: (S)-(4H-spiro[benzo[d][1,3]dioxine-2,1'-cyclohexan]-4-yl)methanol

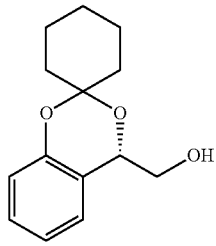 [SMILES: OC[C@H]1OC2(CCCCC2)Oc2ccccc21]

The substantially same method as described in Preparation example 19 was conducted, except that (S)-((4H-spiro[benzo[d][1,3]dioxine-2,1'-cyclohexan]-4-yl)methoxy)(tert-butyl)dimethylsilane obtained in Preparation example 44 was used instead of (R)-tert-butyl((2,2-dimethyl-4H-benzo[d][1,3]dioxin-4-yl) methoxy) dimethylsilane (Preparation example 18), to obtain the title compound (1.3 g, 80~98%)

1H NMR (400 MHz, CDCl₃): δ=1.49~1.50 (m, 4H), 1.67~1.890 (m, 6H), 2.14 (brs, 1H), 3.79~3.84 (m, 1H), 4.03~4.09 (m, 1H), 4.98 (dd, J=2.8, 6.4 1H), 6.85 (dd, J=0.8, 8.0 1H), 6.915 (dt, J=1.0, 7.4, 1H), 7.02 (d, J=7.2, 1H), 7.16~7.20 (m, 1H)

Preparation Example 46: ((4H-spiro[benzo[d][1,3]dioxine-2,1'-cyclohexan]-4-yl)methoxy)(tert-butyl)dimethylsilane

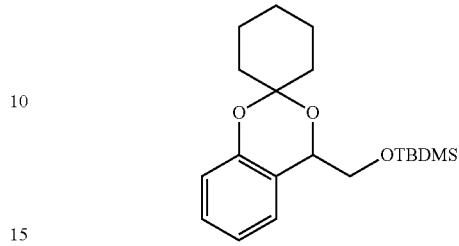

The substantially same method as described in Preparation example 42 was conducted, except that 2-(2-(tert-butyldimethylsilyloxy)-1-hydroxyethyl)phenol obtained in Preparation example 27 was used instead of (R)-2-(2-(tert-butyldimethylsilyloxy)-1-hydroxyethyl)phenol (Preparation example 17), to obtain the title compound (1.9 g, 50~70%)

1H NMR (400 MHz, DMSO) δ=−0.01 (s, 6H), 0.81 (s, 9H), 1.47~1.49 (m, 2H), 1.58 (m, 2H), 1.62~1.72 (m, 4H), 1.83 (m, 2H), 4.21 (t, J=4.4, 1H), 4.26 (dd, J=3.6, 11.2, 2H), 6.77 (d, J=8.0, 1H), 6.89 (d, J=7.6, 1H), 7.19~7.15 (m, 1H), 7.27 (d, J=7.6, 1H).

Preparation Example 47: (4H-spiro[benzo[d][1,3]dioxine-2,1'-cyclohexan]-4-yl)methanol

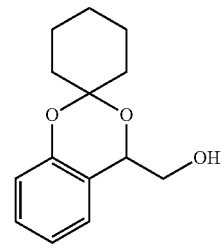 [SMILES: OCC1OC2(CCCCC2)Oc2ccccc21]

The substantially same method as described in Preparation example 19 was conducted, except that ((4H-spiro[benzo[d][1,3]dioxine-2,1'-cyclohexan]-4-yl)methoxy)(tert-butyl)dimethylsilane obtained in Preparation example 46 was used instead of (R)-tert-butyl((2,2-dimethyl-4H-benzo[d][1,3]dioxin-4-yl) methoxy) dimethylsilane (Preparation example 18), to obtain the title compound (1.4 g, 80~98%)

1H NMR (400 MHz, CDCl₃): δ=1.49~1.50 (m, 4H), 1.67~1.89 (m, 6H), 2.14 (brs, 1H), 3.79~3.84 (m, 1H), 4.03~4.09 (m, 1H), 4.98 (dd, J=2.8, 6.4 1H), 6.85 (dd, J=0.8, 8.0 1H), 6.92 (dt, J=1.0, 7.4, 1H), 7.02 (d, J=7.2, 1H), 7.16~7.20 (m, 1H)

Preparation Example 48: Ethyl 3-(2-(benzyloxy)phenyl)-3-hydroxypropanoate

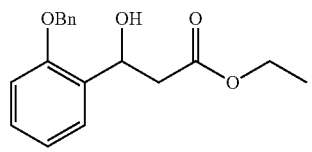 [SMILES: CCOC(=O)CC(O)c1ccccc1OCc1ccccc1]

To a solution of LDA (1.5M solution, 93.3 mL, 139.9 mmol) in THF (50 mL) was cooled to −78° C. and the solution of ethyl acetate (12.3 g, 139.9 mmol) in THF (11 mL) was slowly introduced. The mixture was stirred for 30 min at −78° C. A solution of 2-(benzyloxy)benzaldehyde (Preparation example 13, 14.8 g, 69.9 mmol) in THF (20 mL) was added dropwise, and then the mixture was stirred at same temperature for 30 min. The mixture was slowly warm to rt, and stirred an additional 2 hr. After aqueous work-up (quenched by 0.5M HCl). The organic layer was concentrated to crude oil. The residue was purified by silica gel column chromatography. (19.5 g, 80~99%)

1H NMR (400 MHz, CDCl$_3$) δ 1.239 (t, J=7.0, 3H), 2.65~2.75 (m, 1H), 2.85~2.91 (m, 1H), 3.49 (d, J=5.20, 1H), 4.09~4.22 (m, 2H), 5.12 (s, 2H), 5.41~5.49 (m, 1H), 6.91~6.94 (m, 1H), 6.97~7.02 (m, 1H), 7.21~7.26 (m, 1H), 7.31~7.44 (m, 5H), 7.45~7.49 (m, 1H)

Preparation Example 49: Ethyl 3-hydroxy-3-(2-hydroxyphenyl)propanoate

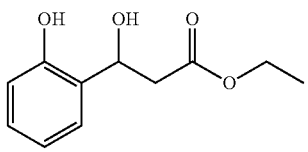

The substantially same method as described in Preparation example 17 was conducted, except that Ethyl 3-(benzyloxy)phenyl-3-hydroxypropanoate obtained in Preparation example 48 was used instead of (R)-1-(2-(benzyloxy)phenyl-2-(tert-butyldimethylsilyloxy)ethanol (Preparation example 16), to obtain the title compound. (15.3 g, 80~99%)

1H NMR (400 MHz, CDCl$_3$) δ1.30 (t, J=7.2, 3H), 2.68~2.77 (m, 1H), 2.92~3.02 (m, 1H), 4.19~4.27 (m, 1H), 4.453 (d, J=2.0, 1H), 5.25~5.31 (m, 1H), 6.82~6.92 (m, 2H), 6.95~7.02 (m, 1H), 7.15~7.24 (m, 1H), 8.171 (s, 1H)

Preparation Example 50: Ethyl 2-(2,2-dimethyl-4H-benzo[d][1,3]dioxin-4-yl)acetate

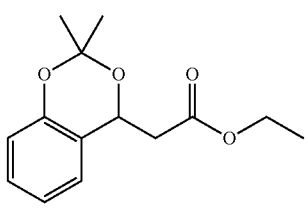 [SMILES: CCOC(=O)CC1OC(C)(C)Oc2ccccc21]

The substantially same method as described in Preparation example 18 was conducted, except that Ethyl 3-hydroxy-3-(2-hydroxyphenyl)propanoate obtained in Preparation example 49 was used instead of (R)-2-(2-(tert-butyldimethylsilyloxy)-1-hydroxyethyl)phenol (Preparation example 17), to obtain the title compound. (4.6 g, 55~85%)

$^1$H NMR (400 MHz, CDCl$_3$) δ 1.28 (t, J=7.0, 3H), 1.50 (s, 3H), 1.57 (s, 3H), 2.71 (q, J=8.1, 1H), 2.92 (q, J=6.4, 1H), 4.15~4.28 (m, 2H), 5.39 (q, J=4.3, 1H), 6.79~6.84 (m, 1H), 6.87~6.93 (m, 1H), 6.97~7.03 (m, 1H), 7.14~7.21 (m, 1H)

Preparation Example 51: 2-(2,2-dimethyl-4H-benzo[d][1,3]dioxin-4-yl)ethanol

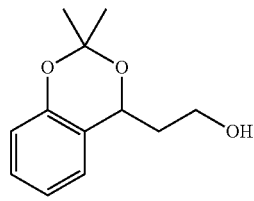

To a stirred solution of ethyl 2-(2,2-dimethyl-4H-benzo[d][1,3]dioxin-4-yl)acetate (Preparation example 50, 3.6 g, 14.5 mmol) in THF (72 mL) was added LAH (1.1 g, 29.1 mmol) at 0° C. then stirred for 1 hr. The resulting mixture was quenched with sat. Na$_2$SO$_4$ solution, filtered through celite, and THF was removed. The residue was diluted with EtOAc, washed with water, dried over MgSO$_4$, filtered and concentrated under reduce pressure. The crude compound was purified by a silica gel column to produce the title compound. (2.9 g, 75~99%)

$^1$H NMR (400 MHz, CDCl$_3$) δ 1.49 (s, 3H), 1.59 (s, 3H), 1.99~2.09 (m, 1H), 2.27~2.35 (m, 1H), 2.36 (t, J=5.0, 1H), 3.75~3.86 (m, 2H), 5.16 (q, J=3.7, 1H), 6.80~6.85 (m, 1H), 6.89~6.95 (m, 1H), 6.99~7.03 (m, 1H), 7.14~7.21 (m, 1H)

Preparation Example 52: 1-(2-(benzyloxy)phenyl)propane-1,3-diol

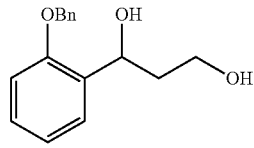 [SMILES: OCCC(O)c1ccccc1OCc1ccccc1]

The substantially same method as described in Preparation example 51 was conducted, except that 3-(2-(benzyloxy)phenyl)-3-hydroxypropanoate obtained in Preparation example 48 was used instead of ethyl 2-(2,2-dimethyl-4H-benzo[d][1,3]dioxin-4-yl)acetate (Preparation example 50), to obtain the title compound. (15.1 g, 60~85%)

1H NMR (400 MHz, CDCl$_3$) δ 1.95~2.13 (m, 2H), 2.48 (t, J=5.2, 1H), 3.04 (d, J=4.8, 1H), 3.82 (q, J=5.3, 2H), 5.10 (s, 2H), 5.23~5.29 (m, 1H), 6.93~6.98 (m, 1H), 6.98~7.03 (m, 1H), 7.22~7.27 (m, 1H), 7.30~7.46 (m, 6H)

Preparation Example 53: 3-(2-(benzyloxy)phenyl)-3-hydroxypropyl pivalate

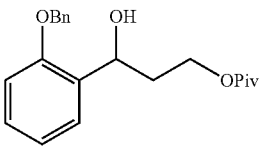

The substantially same method as described in Preparation example 3 was conducted, except that 1-(2-(benzyloxy)phenyl)propane-1,3-diol obtained in Preparation example 52 was used instead of 3-(2-(benzyloxy)phenyl)propane-1,2-diol (Preparation example 2), to obtain the title compound. (6.4 g, 60~85%) ¹H NMR (400 MHz, CDCl₃) δ 1.15 (s, 9H), 1.23 (s, 1H), 2.01~2.21 (m, 2H), 4.08~4.15 (m, 1H), 4.29~4.37 (m, 1H), 5.04 (q, J=4.4, 1H), 5.10 (s, 2H), 6.93~7.02 (m, 2H), 7.21~7.27 (m, 1H), 7.31~7.43 (m, 6H)

Preparation Example 54: 3-hydroxy-3-(2-hydroxyphenyl)propyl pivalate

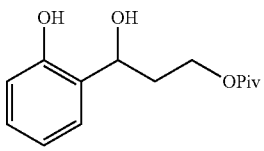

The substantially same method as described in Preparation example 17 was conducted, except that 3-(2-(benzyloxy)phenyl)-3-hydroxypropyl pivalate obtained in Preparation example 53 was used instead of (R)-1-(2-(benzyloxy)phenyl-2-(tert-butyldimethylsilyloxy)ethanol (Preparation example 16), to obtain the title compound. (4.6 g, 80~98%)

1H NMR (400 MHz, CDCl₃) δ 1.23 (s, 9H), 2.04~2.25 (m, 2H), 3.59 (s, 1H), 4.05~4.13 (m, 1H), 4.41~4.49 (m, 1H), 4.87 (q, J=4.13, 1H), 6.79~6.90 (m, H), 6.93 (d, J=7.60, 1H), 7.17 (t, J=7.6, 1H), 7.98 (s, 1H)

Preparation Example 55: 2-(2,2-diethyl-4H-benzo[d][1,3]dioxin-4-yl)ethyl pivalate

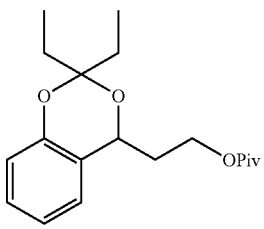

To a stirred solution of 3-hydroxy-3-(2-hydroxyphenyl) propyl pivalate (Preparation example 54, 2.0 g, 7.63 mmol) in 3-pentanone (16 mL) was added H₂SO₄ (0.76 mmol) at room temperature then stirred 1 hr.

The resulting mixture was quenched with sat. NaHCO₃, extracted with EtOAc, washed with brine, dried over Na₂SO₄, filtered and concentrated under reduced pressure. The crude compound was purified by a silica gel column to produce the title compound. (1.9 g, 70~90%)

¹H NMR (400 MHz, CDCl₃) δ 0.89 (t, J=6.2, 3H), 1.01 (t, J=7.4, 3H), 1.19 (s, 9H), 1.70~1.90 (m, 4H), 1.97~2.08 (m, 1H), 2.30~2.41 (m, 1H), 4.18~4.35 (m, 2H), 4.93~5.01 (m, 1H), 6.83~6.89 (m, 2H), 6.99 (d, J=7.6, 1H), 7.14~7.18 (m, 1H) 4H), 1.97~2.08 (m, 1H), 2.30~2.41 (m, 1H), 4.18~4.35 (m, 2H), 4.93~5.01 (m, 1H).

Preparation Example 56: 2-(2,2-diethyl-4H-benzo[d][1,3]dioxin-4-yl)ethanol

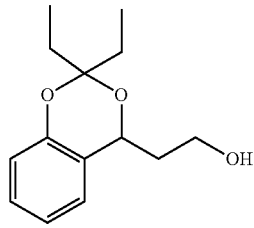 [SMILES: CCC1(CC)Oc2ccccc2C(CCO)O1]

The substantially same method as described in Preparation example 6 was conducted, except that 2-(2,2-diethyl-4H-benzo[d][1,3]dioxin-4-yl)ethyl pivalate obtained in Preparation example 7 was used instead of (2,2-dimethyl-4,5-dihydrobenzo[d][1,3]dioxepin-4-yl)methyl pivalate (Preparation example 5), to obtain the title compound (1.9 g, 70~98%)

1H NMR (400 MHz, CDCl₃) δ 0.92 (t, J=7.60, 3H), 1.01 (t, J=7.40, 3H), 1.75~1.91 (m, 4H), 1.98~2.09 (m, 1H), 2.26~2.35 (m, 1H), 2.387 (t, J=5.40, 1H), 3.76~3.88 (m, 2H), 5.09~5.15 (m, 1H), 6.83 (d, J=8.40, 1H), 6.89 (t, J=7.40, 1H), 6.99 (d, J=7.60, 1H)

Preparation Example 57: 2-(4H-spiro[benzo[d][1,3]dioxine-2,1'-cyclopentane]-4-yl)ethyl pivalate

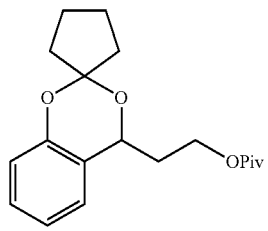

The substantially same method as described in Preparation example 55 was conducted, except that cyclopentanone was used instead of 3-pentanone, to obtain the title compound. (2.9 g, 60~85%)

¹H NMR (400 MHz, CDCl₃) δ 1.19 (s, 9H), 1.68~1.92 (m, 7H), 1.96~2.13 (m, 3H), 2.31~2.40 (m, 1H), 4.17~4.33 (m, 2H), 5.00~5.05 (m, 1H), 6.79~6.83 (m, 1H), 6.88~6.94 (m, 1H), 7.03 (d, J=7.6, 1H), 7.12~7.17 (m, 1H)

Preparation Example 58: 2-(4H-spiro[benzo[d][1,3]dioxine-2,1'-cyclopentane]-4-yl)ethanol

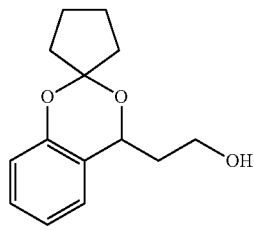 [SMILES: OCCC1OC2(CCCC2)Oc2ccccc21]

The substantially same method as described in Preparation example 6 was conducted, except that 2-(4H-spiro[benzo[d][1,3]dioxine-2,1'-cyclopentane]-4-yl)ethyl pivalate obtained in Preparation example 57 was used instead of (2,2-dimethyl-4,5-dihydrobenzo[d][1,3]dioxepin-4-yl)methyl pivalate (Preparation example 5), to obtain the title compound. (2.3 g, 75~99%)

¹H NMR (400 MHz, CDCl₃) δ 1.17~1.90 (m, 6H), 1.95~2.17 (m, 4H), 2.26~2.35 (m, 2H), 3.77~3.87 (m, 2H), 5.15~5.22 (m, 1H), 6.83 (d, J=8.0, 1H), 6.92 (t, J=7.6, 1H)

Preparation Example 59: 2-(4H-spiro[benzo[d][1,3]dioxine-2,1'-cyclohexane]-4-yl)ethyl pivalate

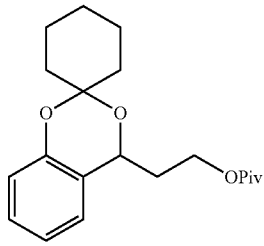

The substantially same method as described in Preparation example 55 was conducted, except that cyclohexanone was used instead of 3-pentanone, to obtain the title compound. (3.7 g, 70~95%)

1H NMR (400 MHz, CDCl₃) δ 1.19 (s, 9H), 1.37~2.55 (m, 4H), 1.62~1.95 (m, 6H), 1.96~2.08 (m, 1H), 2.32~2.42 (m, 1H), 4.21~4.37 (m, 2H), 4.95~5.02 (m, 1H), 6.82 (d, J=8.4, 1H), 6.89 (t, J=7.4, 1H), 7.025 (d, J=7.60, 1H), 7.12~7.18 (m, 1H)

Preparation Example 60: 2-(4H-spiro[benzo[d][1,3]dioxine-2,1'-cyclohexane]-4-yl)ethanol

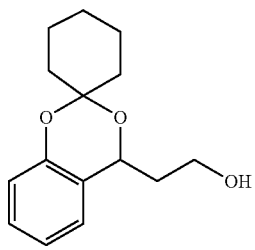 [SMILES: OCCC1OC2(CCCCC2)Oc2ccccc21]

The substantially same method as described in Preparation example 6 was conducted, except that 2-(4H-spiro[benzo[d][1,3]dioxine-2,1'-cyclohexane]-4-yl)ethyl pivalate obtained in Preparation example 59 was used instead of (2,2-dimethyl-4,5-dihydrobenzo[d][1,3]dioxepin-4-yl)methyl pivalate (Preparation example 5), to obtain the title compound. (2.8 g, 7599%)

1H NMR (400 MHz, CDCl₃) δ 1.41~1.94 (m, 10H), 1.98~2.08 (m, 1H), 2.27~2.36 (m, 1H), 2.45 (t, J=5.4, 1H), 3.84 (q, J=5.4, 2H), 5.12~5.17 (m, 1H), 6.82~6.86 (m, 1H), 6.87~6.93 (m, 1H), 6.99 (d, J=7.6, 1H), 7.13~7.20 (m, 1H)

Preparation Example 61: 2-(2-(benzyloxy)phenyl)acetaldehyde

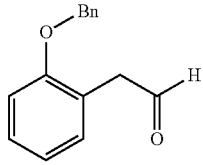 [SMILES: O=CCc1ccccc1OCc1ccccc1]

To a stirred solution of (methoxymethyl)triphenylphosphonium chloride (36.34 g 106 mmol) in THF was added t-BuOK (12.69 g, 113 mmol) at 0° C. After 10 min, the mixture was added 2-(benzyloxy)benzaldehyde (Preparation Example 13, 15 g, 70.67 mmol). When the reaction was completed, the resulting mixture was quenched with sat. NH₄Cl, extracted with Et₂O, washed with brine, dried over MgSO₄ and concentrated under reduced pressure. The crude product was dissolved in THF (150 mL) and then added 3N HCl solution. The reaction mixture was stirred under reflux for 2 h. The resulting mixture was cooled to room temperature, quenched with sat. NaHCO₃, extracted with Et₂O, washed with brine, dried over MgSO₄ and concentrated under reduced pressure. The crude product was purified by a silica gel column chromatography to produce the title compound (9.9 g, 55~70%)

1H NMR (400 MHz, CDCl₃) δ 3.74 (s, 2H), 5.12 (s, 2H), 6.95~7.04 (m, 2H) 7.19~7.21 (m, 1H), 7.25~7.39 (m, 2H), 7.41~7.47 (m, 4H), 9.86 (s, 1H)

Preparation Example 62: Ethyl 4-(2-(benzyloxy)phenyl)-3-hydroxybutanoate

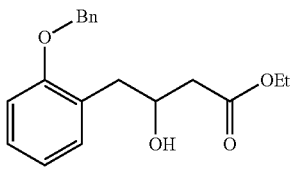 [SMILES: CCOC(=O)CC(O)Cc1ccccc1OCc1ccccc1]

To a stirred solution of lithium diisopropylamide (57.7 mL, 86.6 mol) in THF was slowly added ethylacetate (8.5 mL, 86.6 mmol) at −78° C. under N2. After 10 min, the mixture was added 2-(2-(benzyloxy)phenyl)acetaldehyde (Preparation Example 61, 9.8 g, 43.31 mmol). When the reaction was completed, the resulting mixture was warmed to room temperature, filtered through celite pad, extracted with EtOAc, washed with water, dried over MgSO₄, filtered and concentrated under reduced pressure. The crude product was purified by a silica gel column chromatography to produce the title compound (11.5 g, 70~90%)

1H NMR (400 MHz, CDCl₃) δ 1.26 (t, J=7.2, 3H), 2.42~2.55 (m, 1H), 2.91~3.00 (m, 2H), 3.05 (d, J=4.0, 1H), 4.14 (q, J=7.2, 2H), 4.36~4.42 (m, 1H), 5.11 (s, 2H), 6.93~6.97 (m, 2H), 7.21~7.25 (m, 2H), 7.33~7.46 (m, 5H)

Preparation Example 63: Ethyl 3-hydroxy-4-(2-(benzyloxy)phenyl)butanoate

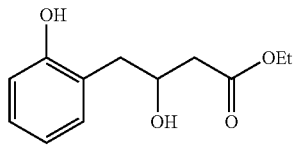 [SMILES: CCOC(=O)CC(O)Cc1ccccc1O]

To a stirred solution of ethyl 4-(2-(benzyloxy)phenyl)-3-hydroxybutanoate (Preparation Example 62, 1 g, 3.18 mmol) in EtOAc (10 mL) was added Pd(OH)$_2$ (0.2 g, 0.2 w/w) and then hydrogen gas balloon installed. The reaction mixture was stirred for 2 h at room temperature. The resulting mixture was filtered through celite pad and concentrated under reduced pressure (0.68 g, 80~95%)

1H NMR (400 MHz, CDCl3) δ 1.29 (t, J=7.0, 3H), 2.40~2.50 (m, 2H), 2.81~3.00 (m, 2H), 3.05 (s, 1H), 4.04 (q, J=7.2, 2H), 4.24 (q, J=7.2, 1H), 5.11 (s, 1H), 6.93~6.97 (m, 2H), 7.21~7.25 (m, 1H), 7.28 (s, 1H)

Preparation Example 64: Ethyl 2-(2,2-dimethyl-4,5-dihydrobenzo[d][1,3]dioxepin-4-yl)acetate

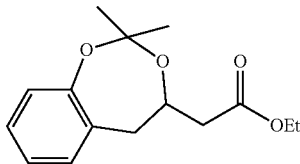 [SMILES: CCOC(=O)CC1Cc2ccccc2OC(C)(C)O1]

To a stirred solution of ethyl 3-hydroxy-4-(2-hydroxyphenyl)butanoate (Preparation Example 63, 0.68 g, 3 mmol) in dichloromethane was added 2-methoxypropene (0.86 mL, 9 mmol) and pyridinium p-toluenesulfonate (0.084 g, 0.3 mmol) then stirred at room temperature for overnight. The resulting mixture was diluted with dichloromethane, washed with water, dried over MgSO$_4$, filtered and concentrated under reduce pressure. The crude product was purified by a silica gel column chromatography to produce the title compound (0.65 g, 70~90%)

1H NMR (400 MHz, CDCl$_3$) δ 1.29 (t, J=7.0, 3H), 1.45 (s, 3H), 1.48 (s, 3H), 2.52 (dd, J=5.2, 15.2, 1H), 2.63 (dd, J=8.3, 15.2, 1H), 2.90~2.92 (m, 2H), 4.20 (q, J=6.0, 2H), 4.59~4.65 (m, 1H), 6.91 (d, J=8.0, 1H), 7.02~7.09 (m, 2H), 7.14~7.18 (m, 1H)

Preparation Example 65: 2-(2,2-dimethyl-4,5-dihydrobenzo[d][1,3]dioxepin-4-yl)ethanol

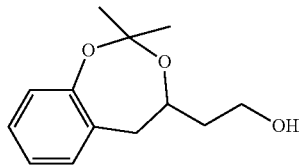 [SMILES: CC1(C)Oc2ccccc2CC(CCO)O1]

To a stirred solution of ethyl 2-(2,2-dimethyl-4,5-dihydrobenzo[d][1,3]dioxepin-4-yl)acetate (Preparation Example 64, 0.65 g, 2.46 mmol) in THF was added LAH solution (2.4M in THF, 0.7 mL, 1.7 mmol) at 0° C. The reaction mixture was stirred at 0° C. for 1 h. The resulting mixture was quenched with sat. Na$_2$SO$_4$ solution, filtered through celite pad and then removed THF. The residue was diluted with EtOAc, washed with H$_2$O, dried over MgSO$_4$, filtered and concentrated under reduce pressure. The crude product was purified by a silica gel column chromatography (0.48 g, 80~100%)

1H NMR (400 MHz, CDCl$_3$) δ 1.47 (s, 3H), 1.53 (s, 3H), 1.79~1.92 (m, 2H), 2.32~2.34 (m, 1H), 2.89 (dd, J=3.0, 15.4, 1H), 3.01 (dd, J=9.6, 15.2, 1H), 3.81~3.85 (m, 2H), 4.34~4.40 (m, 1H), 6.92 (d, J=8.0, 1H), 7.03~7.10 (m, 2H), 7.14~7.19 (m, 1H)

Preparation Example 66: Ethyl 2-(2,2-diethyl-4,5-dihydrobenzo[d][1,3]dioxepin-4-yl)acetate

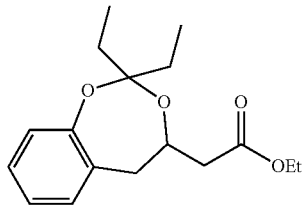 [SMILES: CCOC(=O)CC1Cc2ccccc2OC(CC)(CC)O1]

To a stirred solution of 3-hydroxy-4-(2-benzyloxy)phenyl)butanoate (Preparation Example 63, 2.0 g, 8.9 mmol) in 3-pentanone (4.7 mL, 44.5 mmol) was added a catalytic amount of H$_2$SO$_4$ (0.05 mL, 0.9 mmol) at room temperature. The mixture was stirred for 12 h. The resulting mixture was diluted with EtOAc, washed with water, dried over MgSO$_4$, filtered, and concentrated under reduced pressure. The crude compound was purified by a silica gel column to produce the title compound (1.9 g, 60~80%)

1H NMR (400 MHz, CDCl$_3$) δ 0.91~0.95 (m, 6H), 1.29 (t, J=7.0, 3H), 1.67~1.74 (m, 4H), 2.49 (dd, J=5.2, 15.2, 1H), 2.60 (dd, J=8.3, 15.2, 1H), 2.96~2.99 (m, 2H), 4.20 (q, J=6.0, 2H), 4.58~4.64 (m, 1H), 6.92 (d, J=8.0, 1H), 7.02~7.09 (m, 2H), 7.14~7.18 (m, 1H).

Preparation Example 67: 2-(2,2-diethyl-4,5-dihydrobenzo[d][1,3]dioxepin-4-yl)ethanol

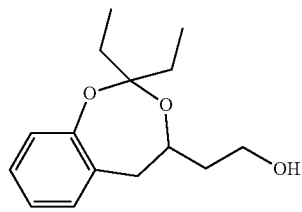 [SMILES: CCC1(CC)Oc2ccccc2CC(CCO)O1]

The substantially same method as described in Preparation example 65 was conducted, except that Ethyl 2-(2,2-diethyl-4,5-dihydrobenzo[d][1,3]dioxepin-4-yl)acetate (Preparation example 66) was used instead of Ethyl 2-(2,2-dimethyl-4,5-dihydrobenzo[d][1,3]dioxepin-4-yl)acetate (Preparation Example 64), to obtain the title compound. (1.6 g, 80~100%)

1H NMR (400 MHz, CDCl$_3$) δ 0.90~0.95 (m, 6H), 1.62~1.70 (m, 4H), 1.81~1.90 (m, 2H), 2.33~2.34 (m, 1H), 2.94 (dd, J=3.0, 15.4, 1H), 3.06 (dd, J=9.6, 15.2, 1H), 3.78~3.83 (m, 2H), 4.37~4.42 (m, 1H), 6.91 (d, J=8.0, 1H), 7.02~7.09 (m, 2H), 7.14~7.18 (m, 1H).

Preparation Example 68: Ethyl 2-(4,5-dihydrospiro[benzo[d][1,3]dioxepine-2,1'-cyclopentan]-4-yl)acetate

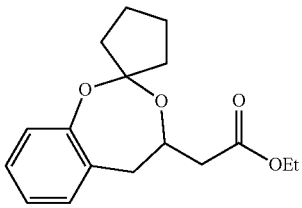 [SMILES: CCOC(=O)CC1Cc2ccccc2OC2(CCCC2)O1]

The substantially same method as described in Preparation example 66 was conducted, except that cyclopentanone was used instead of 3-pentanon, to obtain the title compound. (1.7 g, 60~80%)

1H NMR (400 MHz, CDCl$_3$) δ 1.29 (t, J=7.0, 3H), 1.64~1.80 (m, 5H), 1.88~2.00 (m, 3H), 2.52 (dd, J=5.2, 15.2, 1H), 2.63 (dd, J=8.3, 15.2, 1H), 2.89~2.92 (m, 2H), 4.20 (q, J=6.0, 2H), 4.59~4.66 (m, 1H), 6.91 (d, J=8.0, 1H), 7.02~7.09 (m, 2H), 7.14~7.18 (m, 1H).

Preparation Example 69: 2-(4,5-dihydrospiro[benzo[d][1,3]dioxepine-2,1'-cyclopentan]-4-yl)ethanol

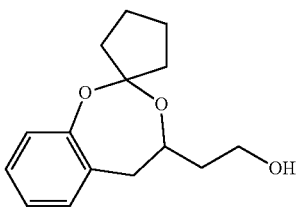 [SMILES: OCCC1Cc2ccccc2OC2(CCCC2)O1]

The substantially same method as described in Preparation example 65 was conducted, except that Ethyl 2-(4,5-dihydrospiro[benzo[d][1,3]dioxepine-2,1'-cyclopentan]-4-yl)acetate (Preparation example 68) was used instead of Ethyl 2-(2,2-dimethyl-4,5-dihydrobenzo[d][1,3]dioxepin-4-yl)acetate (Preparation Example 64), to obtain the title compound. (1.4 g, 80~100%)

1H NMR (400 MHz, CDCl$_3$) δ 1.68~1.74 (m, 3H), 1.80~1.87 (m, 5H), 1.78~1.93 (m, 2H), 2.32~2.35 (m, 1H), 2.89 (dd, J=3.0, 15.4, 1H), 3.01 (dd, J=9.6, 15.2, 1H), 3.81~3.85 (m, 2H), 4.34~4.40 (m, 1H), 6.91 (d, J=8.0, 1H), 7.02~7.09 (m, 2H), 7.14~7.18 (m, 1H).

Preparation Example 70: Ethyl 2-(4,5-dihydrospiro[benzo[d][1,3]dioxepine-2,1'-cyclohexan]-4-yl)acetate

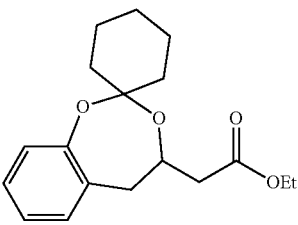 [SMILES: CCOC(=O)CC1Cc2ccccc2OC2(CCCCC2)O1]

The substantially same method as described in Preparation example 66 was conducted, except that cyclohexanone was used instead of 3-pentanon, to obtain the title compound. (1.7 g, 60~80%)

1H NMR (400 MHz, CDCl$_3$) δ 1.29 (t, J=7.0, 3H), 1.55~1.66 (m, 10H), 2.48 (dd, J=5.2, 15.2, 1H), 2.58 (dd, J=8.3, 15.2, 1H), 2.96~2.98 (m, 2H), 4.20 (q, J=6, 2H), 4.59~4.65 (m, 1H), 6.91 (d, J=8.0, 1H), 7.02~7.09 (m, 2H), 7.14~7.18 (m, 1H).

Preparation Example 71: 2-(4,5-dihydrospiro[benzo[d][1,3]dioxepine-2,1'-cyclohexan]-4-yl)ethanol

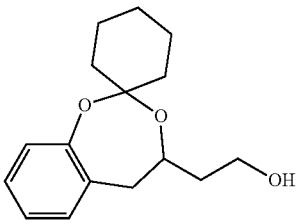 [SMILES: OCCC1Cc2ccccc2OC2(CCCCC2)O1]

The substantially same method as described in Preparation example 65 was conducted, except that Ethyl 2-(4,5-dihydrospiro[benzo[d][1,3]dioxepine-2,1'-cyclohexan]-4-yl)acetate (Preparation example 70) was used instead of Ethyl 2-(2,2-dimethyl-4,5-dihydrobenzo[d][1,3]dioxepin-4-yl)acetate (Preparation Example 64), to obtain the title compound. (1.0 g, 80~100%)

1H NMR (400 MHz, CDCl$_3$) δ 1.55~1.66 (m, 10H), 1.82~1.90 (m, 2H), 2.32~2.34 (m, 1H), 2.92 (dd, J=3.0, 15.4, 1H), 3.08 (dd, J=9.6, 15.2, 1H), 3.78~3.82 (m, 2H), 4.38~4.42 (m, 1H), 6.91 (d, J=8.0, 1H), 7.02~7.09 (m, 2H), 7.14~7.18 (m, 1H).

Preparation Example 72: (S)-((1R,2S,5R)-2-isopropyl-5-methyl cyclohexyl) 2-(3-chloro-2-hydroxyphenyl)-2-hydroxyacetate

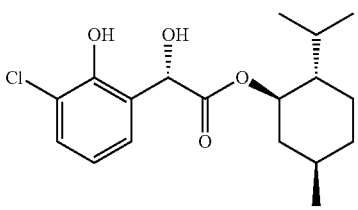 [SMILES: CC(C)[C@@H]1CC[C@@H](C)C[C@H]1OC(=O)[C@@H](O)c1cccc(Cl)c1O]

To a stirred solution of TiCl$_4$ (1M solution, 140 mL, 140 mmol) in CH$_2$Cl$_2$ (50 mL) was added 2-chlorophenol (15 g, 116.68 mmol) in CH$_2$Cl$_2$ (20 mL) at −30° C. The mixture was stirred for 30 min then was added (1R)-(−)-menthyl glyoxylate hydrate (26.87 g, 116.68 mmol) in CH$_2$Cl$_2$ (300 mL). The mixture was slowly warmed to room temperature and stirred for overnight. The resulting mixture was quenched with H$_2$O, extracted with CH$_2$Cl$_2$, washed with H$_2$O, dried over MgSO$_4$, filtered and concentrated under reduced pressure. The crude compound was dissolved in hexane and warmed to 40° C. The mixture was slowly cooled to 0° C. then became white precipitate, stirred for 1 hr, and filtered. (26.7 g, 45~70%, 96% ee)

1H NMR (400 MHz, CDCl$_3$) δ 0.75~1.90 (m, 18H), 3.63 (d, J=5.20, 1H) 4.75~4.84 (m, 1H), 5.34 (d, J=5.5, 1H), 6.87 (t, J=8.0, 1H) 7.13~7.18 (m, 1H), 7.28~7.34 (m, 1H)

Preparation Example 73: (S)-((1R,2S,5R)-2-isopropyl-5-methylcyclohexyl) 8-chloro-2,2-dimethyl-4H-benzo[d][1,3]dioxine-4-carboxylate

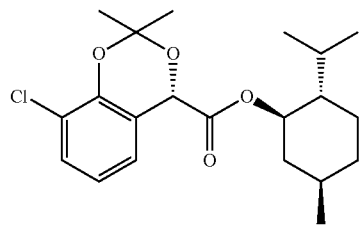 [SMILES: CC(C)[C@@H]1CC[C@@H](C)C[C@H]1OC(=O)[C@H]1OC(C)(C)Oc2c(Cl)cccc21]

To a stirred solution of (S)-((1R,2S,5R)-2-isopropyl-5-methylcyclohexyl) 2-(3-chloro-2-hydroxyphenyl)-2-hydroxyacetate (Preparation example 72, 1.0 g, 2.95 mol) in THF (10 mL) was added 2-methoxypropene (1.06 g, 14.75 mmol) and a catalytic amount of H$_2$SO$_4$ at 35° C. then stirred for 2 hr. The resulting mixture was diluted with dichloromethane, washed with water, dried over anhydrous MgSO$_4$, filtered and concentrated under reduced pressure. The crude compound was purified by a silica gel column to produce the title compound (0.98 g, 80~95%), 1H NMR (400 MHz, CDCl$_3$) δ 0.68~2.05 (m, 24H), 4.76~4.86 (m, 1H), 5.41 (s, 1H). 6.86 (t, J=8.0, 1H), 7.19~7.24 (m, 1H), 7.27~7.32 (m, 1H)

Preparation Example 74: (S)-(8-chloro-2,2-dimethyl-4H-benzo[d][1,3]dioxin-4-yl)methanol

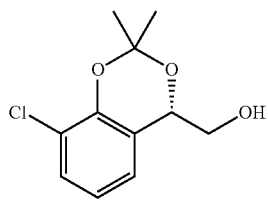

To a stirred solution of (S)-((1S,2S,5R)-2-isopropyl-5-methylcyclohexyl) 8-chloro-2,2-dimethyl-4H-benzo[d][1,3]dioxine-4-carboxylate (Preparation example 73, 1.7 g, 4.46 mmol) in THF (17 mL) was added LAH solution (2.4M in THF, 1.2 mL, 2.95 mmol) at 0° C. The reaction mixture was stirred at 0° C. for 1 hr. The resulting mixture was quenched with sat. Na$_2$SO$_4$ solution, filtered through celite and then THF was removed. The residue, was diluted with EtOAc, washed with H$_2$O, dried over MgSO$_4$, filtered and concentrated under reduced pressure. The crude product was purified by silica gel column chromatography (0.8 g, 70~90%).

$^1$H NMR (400 MHz, CDCl$_3$) δ 1.52 (s, 3H), 1.69 (s, 3H), 2.09 (t, J=6.6, 1H), 3.78~3.86 (m, 1H), 4.01~4.09 (m, 1H), 4.95~5.02 (m, 1H), 6.86 (t. J=7.8, 1H), 6.90 (d, J=7.6, 1H), 7.25~7.29 (m, 1H).

Preparation Example 75: (R)-((1S,2R,5S)-2-isopropyl-5-methylcyclohexyl) 2-(3-chloro-2-hydroxyphenyl)-2-hydroxyacetate

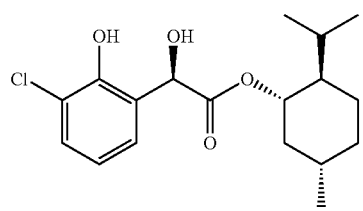 [SMILES: CC(C)[C@H]1CC[C@H](C)C[C@@H]1OC(=O)[C@H](O)c1cccc(Cl)c1O]

The substantially same method as described in Preparation example 72 was conducted, except that (1S)-(+)-Menthyl glyoxylate monohydrate (Alfa Aesar, L19785) was used instead of (1R)-(−)-menthyl glyoxylate hydrate, to obtain the title compound (6.1 g, 45~70%, 96% ee)

1H NMR (400 MHz, CDCl$_3$) δ 0.75~1.90 (m, 18H), 3.63 (d, J=5.20, 1H) 4.75~4.84 (m, 1H), 5.34 (d, J=5.5, 1H), 6.87 (t, J=8.0, 1H) 7.13~7.18 (m, 1H), 7.28~7.34 (m, 1H)

Preparation Example 76: (R)-((1S,2R,5S)-2-isopropyl-5-methylcyclohexyl) 8-chloro-2,2-dimethyl-4H-benzo[d][1,3]dioxine-4-carboxylate

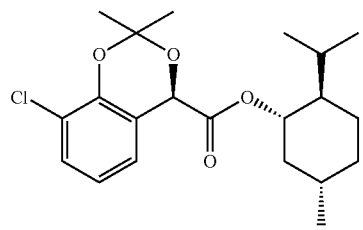 [SMILES: CC(C)[C@H]1CC[C@H](C)C[C@@H]1OC(=O)[C@@H]1OC(C)(C)Oc2c(Cl)cccc21]

The substantially same method as described in Preparation example 73 was conducted, except that (R)-((1S,2R,5S)-2-isopropyl-5-methylcyclohexyl) 2-(3-chloro-2-hydroxyphenyl)-2-hydroxyacetate (Preparation example 75) was used instead of (S)-((1R,2S,5R)-2-isopropyl-5-methylcyclohexyl) 2-(3-chloro-2-hydroxyphenyl)-2-hydroxyacetate (Preparation example 72, to obtain the title compound. (1.8 g, 80~95%)

1H NMR (400 MHz, CDCl$_3$) δ 0.7~2.05 (m, 24H), 4.76~4.86 (m, 1H), 5.41 (s, 1H), 6.86 (t, J=8.0, 1H), 7.19~7.24 (m, 1H), 7.27~7.32 (m, 1H)

Preparation Example 77: (R)-(8-chloro-2,2-dimethyl-4H-benzo[d][1,3]dioxin-4-yl)methanol

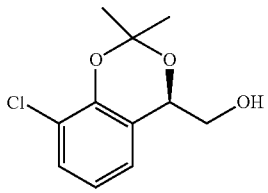

The substantially same method as described in Preparation example 74 was conducted, except that (R)-((1S,2R,5S)-2-isopropyl-5-methylcyclohexyl) 8-chloro-2,2-dimethyl-4H-benzo[d][1,3]dioxine-4-carboxylate (Preparation example 76) was used instead of (S)-((1R,2S,5R)-2-isopropyl-5-methylcyclohexyl) 8-chloro-2,2-dimethyl-4H-benzo[d][1,3]dioxine-4-carboxylate (Preparation example 73), to obtain the title compound. (0.6 g, 70~90%)

1H NMR (400 MHz, CDCl₃) δ 1.52 (s, 3H), 1.69 (s, 3H), 2.09 (t, J=6.6, 1H), 3.78~3.86 (m, 1H), 4.01~4.09 (m, 1H), 4.95~5.02 (m, 1H), 6.86 (t, J=7.8, 1H), 6.97 (d, J=7.6, 1H), 7.25~7.29 (m, 1H)

Preparation Example 78: Ethyl 2-(3-chloro-2-hydroxyphenyl)-2-hydroxyacetate

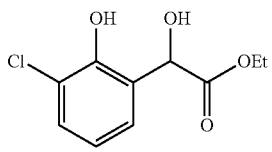 [SMILES: CCOC(=O)C(O)c1cccc(Cl)c1O]

To a stirred solution of 2-chlorophenol (0.63 g, 4.9 mmol)) in CH₂Cl₂ was added ethyl glyoxylate solution (1.0 mL, 5.39 mmol) at room temperature. And then the reaction mixture was added TiCl₄ in CH₂Cl₂ (1.47 mL, 1.47 mmol) at −30° C. The mixture was stirred for 20 hr then the resulting mixture was diluted with CH₂Cl₂, washed with water, dried over MgSO₄, filtered, and concentrated under reduced pressure. The crude product was purified by a silica gel column to obtain the title compound (0.53 g, 45~70%).

¹H NMR (400 MHz, CDCl₃) δ 1.42 (t, J=6.4, 3H), 4.05 (s, 1H), 4.06~4.31 (m, 2H), 5.27 (s, 1H), 5.34 (s, 1H), 6.88 (t, J=8.0, 1H), 7.04~7.10 (m, 1H), 7.21~7.25 (m, 1H).

Preparation Example 79: Ethyl 8-chloro-2,2-dimethyl-4H-benzo[d][1,3]dioxine-4-carboxylate

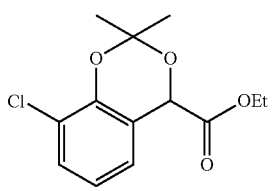 [SMILES: CCOC(=O)C1OC(C)(C)Oc2c(Cl)cccc21]

The substantially same method as described in Preparation example 73 was conducted, except that Ethyl 2-(3-chloro-2-hydroxyphenyl)-2-hydroxyacetate (Preparation example 78) was used instead of (S)-((1R,2S,5R)-2-isopropyl-5-methylcyclohexyl) 2-(3-chloro-2-hydroxyphenyl)-2-hydroxyacetate (Preparation example 72), to obtain the title compound. (1.2 g, 80~95%)

1H NMR (400 MHz, CDCl₃) δ=1.40 (t, J=6.4, 3H), 1.52 (S, 3H), 1.63 (s, 3H), 4.06~4.31 (m, 2H), 5.01 (s, 1H), 6.87 (t, J=8.0, 1H), 7.13~7.18 (m, 1H), 7.28~7.34 (m, 1H).

Preparation Example 80: (8-chloro-2,2-dimethyl-4H-benzo[d][1,3]dioxin-4-yl)methanol

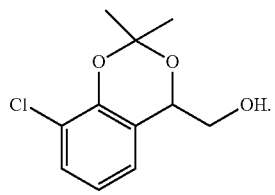

The substantially same method as described in Preparation example 74 was conducted, except that Ethyl 8-chloro-2,2-dimethyl-4H-benzo[d][1,3]dioxine-4-carboxylate (Preparation example 79) was used instead of (S)-((1R,2S,5R)-2-isopropyl-5-methylcyclohexyl) 8-chloro-2,2-dimethyl-4H-benzo[d][1,3]dioxine-4-carboxylate (Preparation example 73), to obtain the title compound. (1.5 g, 70~90%)

¹H NMR (400 MHz, CDCl₃) δ 1.52 (s, 3H), 1.69 (s, 3H), 2.09 (t, J=6.6, 1H), 3.78~3.86 (m, 1H), 4.01~4.09 (m, 1H), 4.95~5.02 (m, 1H), 6.86 (t, J=7.8, 1H), 6.97 (d, J=7.6, 1H), 7.25~7.29 (m, 1H).

Preparation Example 81: (S)-((1R,2S,5R)-2-isopropyl-5-methylcyclohexyl) 8-chloro-2,2-diethyl-4H-benzo[d][1,3]dioxine-4-carboxylate

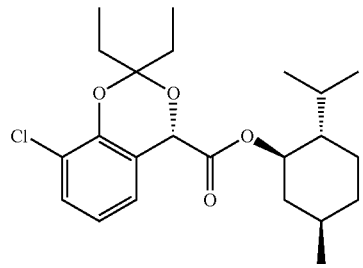 [SMILES: CCC1(CC)Oc2c(Cl)cccc2[C@@H](C(=O)O[C@@H]2C[C@H](C)CC[C@H]2C(C)C)O1]

To a stirred solution of (S)-(1R,2S,5R)-2-isopropyl-5-methylcyclohexyl 2-(3-chloro-2-hydroxyphenyl)-2-hydroxyacetate (Preparation example 72, 3.0 g, 8.80 mmol) in benzene (30 mL) was added 3-pentanone (1.52 g, 17.6 mmol), P₂O₅ (6.25 g, 44.03 mmol) and pyridinium p-toluenesulfonate (0.17 g, 0.87 mmol) then stirred at room temperature for 2 hr. The resulting mixture was diluted with dichloromethane, washed with water, dried over MgSO₄, filtered and concentrated under reduced pressure. The crude product was purified by silica gel column chromatography to produce the title compound (3.6 g, 80~95%).

¹H NMR (400 MHz, CDCl₃) δ 0.64~2.10 (m, 28H), 4.70~4.85 (m, 1H), 5.37 (s, 1H), 6.84 (t, J=7.8, 1H), 7.18 (d, J=8.0, 1H), 7.28 (d, J=8.0, 1H).

Preparation Example 82: (S)-(8-chloro-2,2-diethyl-4H-benzo[d][1,3]dioxin-4-yl)methanol

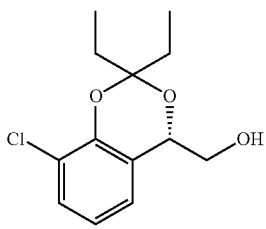

The substantially same method as described in Preparation example 74 was conducted, except that (S)-((1R,2S,5R)-2-isopropyl-5-methylcyclohexyl) 8-chloro-2,2-diethyl-4H-benzo[d][1,3]dioxine-4-carboxylate (Preparation example 81) was used instead of (S)-((1R,2S,5R)-2-isopropyl-5-methylcyclohexyl) 8-chloro-2,2-dimethyl-4H-benzo[d][1,3]dioxine-4-carboxylate (Preparation example 73), to obtain the title compound. (1.8 g, 70~90%)

$^1$H NMR (400 MHz, CDCl$_3$) δ 0.93 (t, J=7.6, 3H), 1.06 (t, J=7.4, 3H), 1.71~1.86 (m, 2H), 1.86~1.97 (m, 2H), 2.13 (q, J=4.4, 1H), 3.77~3.86 (m, 1H), 4.00~4.08 (m, 1H), 4.91~4.97 (m, 1H), 6.84 (t, J=7.8, 1H), 6.92~6.97 (m, 1H), 7.22~7.28 (m, 1H).

Preparation Example 83: (R)-((1S,2R,5S)-2-isopropyl-5-methylcyclohexyl) 8-chloro-2,2-diethyl-4H-benzo[d][1,3]dioxine-4-carboxylate

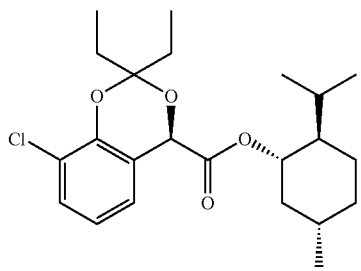 [SMILES: CCC1(CC)Oc2c(Cl)cccc2[C@H](C(=O)O[C@H]2C[C@@H](C)CC[C@@H]2C(C)C)O1]

The substantially same method as described in Preparation example 81 was conducted, except that (R)-(1S,2R,5S)-2-isopropyl-5-methylcyclohexyl 2-(3-chloro-2-hydroxyphenyl)-2-hydroxyacetate (Preparation example 75) was used instead of (S)-(1R,2S,5R)-2-isopropyl-5-methylcyclohexyl 2-(3-chloro-2-hydroxyphenyl)-2-hydroxyacetate (Preparation example 72), to obtain the title compound. (1.9 g, 80~95%)

$^1$H NMR (400 MHz, CDCl$_3$) δ 0.64~2.10 (m, 28H), 4.70~4.85 (m, 1H), 5.37 (s, 1H), 6.83 (t, J=7.8, 1H), 7.17 (d, J=8.0, 1H), 7.27 (d, J=8.0, 1H).

Preparation Example 84: (R)-(8-chloro-2,2-diethyl-4H-benzo[d][1,3]dioxin-4-yl)methanol

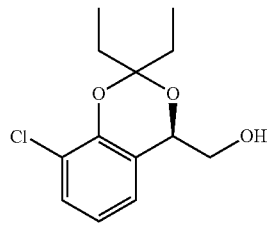 [SMILES: CCC1(CC)Oc2c(Cl)cccc2[C@H](CO)O1]

The substantially same method as described in Preparation example 74 was conducted, except that (R)-((1S,2R,5S)-2-isopropyl-5-methylcyclohexyl) 8-chloro-2,2-diethyl-4H-benzo[d][1,3]dioxine-4-carboxylate (Preparation example 83) was used instead of (S)-((1R,2S,5R)-2-isopropyl-5-methylcyclohexyl) 8-chloro-2,2-dimethyl-4H-benzo[d][1,3]dioxine-4-carboxylate (Preparation example 73), to obtain the title compound. (1.2 g, 70~90%)

$^1$H NMR (400 MHz, CDCl$_3$) δ 0.93 (t, J=7.6, 3H), 1.06 (t, J=7.4, 3H), 1.71~1.86 (m, 2H), 1.86~1.97 (m, 2H), 2.13 (q, J=4.4, 1H), 3.77~3.86 (m, 1H), 4.00~4.08 (m, 1H), 4.91~4.97 (m, 1H), 6.84 (t, J=7.8, 1H), 6.92~6.97 (m, 1H), 7.22~7.28 (m, 1H).

Preparation Example 85: Ethyl 8-chloro-2,2-diethyl-4H-benzo[d][1,3]dioxin-4-carboxylate

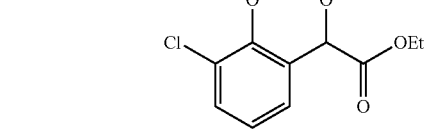

The substantially same method as described in Preparation example 81 was conducted, except that Ethyl 2-(3-chloro-2-hydroxyphenyl)-2-hydroacetate (Preparation example 78) was used instead of (S)-(1R,2S,5R)-2-isopropyl-5-methylcyclohexyl 2-(3-chloro-2-hydroxyphenyl)-2-hydroxyacetate (Preparation example 72), to obtain the title compound. (1.1 g, 80~95%)

1H NMR (400 MHz, CDCl$_3$) δ 0.93 (t, J=7.6, 3H), 1.06 (t, J=7.4, 3H), 1.42 (t, J=6.4, 3H), 1.71~1.86 (m, 2H), 1.86~1.97 (m, 2H), 4.06~4.31 (m, 2H), 4.96 (s, 1H), 6.84 (t, J=7.8, 1H), 6.92~6.97 (m, 1H), 7.22~7.28 (m, 1H)

Preparation Example 86: (8-chloro-2,2-diethyl-4H-benzo[d][1,3]dioxin-4-yl)methanol

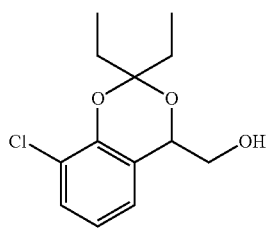

The substantially same method as described in Preparation example 74 was conducted, except that Ethyl 8-chloro-2,2-diethyl-4H-benzo[d][1,3]dioxin-4-carboxylate (Preparation example 85) was used instead of (S)-((1R,2S,5R)-2-isopropyl-5-methylcyclohexyl) 8-chloro-2,2-dimethyl-4H-benzo[d][1,3]dioxine-4-carboxylate (Preparation example 73), to obtain the title compound. (1.2 g, 70~90%)

¹H NMR (400 MHz, CDCl$_3$) δ 0.93 (t, J=7.6, 3H), 1.06 (t, J=7.4, 3H), 1.71~1.86 (m, 2H), 1.86~1.97 (m, 2H), 2.13 (q, J=4.4, 1H), 3.77~3.86 (m, 1H), 4.00~4.08 (m, 1H), 4.91~4.97 (m, 1H), 6.84 (t, J=7.80, 1H), 6.92~6.97 (m, 1H), 7.22~7.28 (m, 1H)

Preparation Example 87: (S)-((1R,2S,5R)-2-isopropyl-5-methylcyclohexyl) 8-chloro-4H-spiro[benzo[d][1,3]dioxine-2,1'-cyclopentane]-4-carboxylate

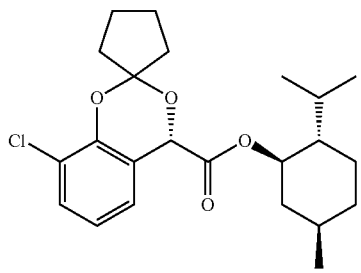 [SMILES: CC(C)[C@@H]1CC[C@@H](C)C[C@H]1OC(=O)[C@H]1OC2(CCCC2)Oc2c(Cl)cccc21]

The substantially same method as described in Preparation example 81 was conducted, except that cyclopentanone was used instead of 3-pentanone, to obtain the title compound. (3.7 g, 80~95%)

¹H NMR (400 MHz, CDCl$_3$) δ 0.71 (d, J=6.8, 3H), 0.84 (d, J=7.2, 3H), 0.90 (d, J=6.4, 3H), 0.99~1.15 (m, 2H), 1.41~2.33 (m, 15H), 2.80 (t, J=7.4, 1H), 4.77~4.87 (m, 1H), 5.43 (s, 1H), 6.85 (t, J=8.0, 1H), 7.18~7.23 (m, 1H), 7.26~7.31 (m, 1H).

Preparation Example 88: (S)-(8-chloro-4H-spiro[benzo[d][1,3]dioxine-2,1'-cyclopentan]-4-yl)methanol

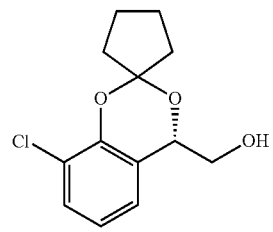 [SMILES: OC[C@H]1OC2(CCCC2)Oc2c(Cl)cccc21]

The substantially same method as described in Preparation example 74 was conducted, except that (R)-((1S,2R,5S)-2-isopropyl-5-methylcyclohexyl) 8-chloro-4H-spiro[benzo[d][1,3]dioxine-2,1'-cyclopentane]-4-carboxylate (Preparation example 87) was used instead of (S)-((1R,2S,5R)-2-isopropyl-5-methylcyclohexyl) 8-chloro-2,2-dimethyl-4H-benzo[d][1,3]dioxine-4-carboxylate (Preparation example 73), to obtain the title compound. (1.9 g, 70~90%)

1H NMR (400 MHz, CDCl$_3$) δ 1.72~1.98 (m, 2H), 2.02~2.17 (m, 2H), 2.21~2.30 (m, 1H), 3.78~3.88 (m, 1H), 4.01~4.09 (m, 1H), 4.96~5.06 (m, 1H), 6.87 (t, J=7.8, 1H), 6.96 (d, J=7.6, 1H), 7.26 (d, J=7.6, 1H)

Preparation Example 89: (R)-((1S,2R,5S)-2-isopropyl-5-methylcyclohexyl) 8-chloro-4H-spiro[benzo[d][1,3]dioxine-2,1'-cyclopentane]-4-carboxylate

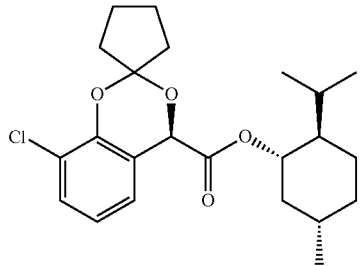 [SMILES: CC(C)[C@H]1CC[C@H](C)C[C@@H]1OC(=O)[C@@H]1OC2(CCCC2)Oc2c(Cl)cccc21]

The substantially same method as described in Preparation example 83 was conducted, except that cyclopentanone was used instead of 3-pentanone, to obtain the title compound. (2.5 g, 80~95%)

1H NMR (400 MHz, CDCl$_3$) δ 0.72 (d, J=6.8, 3H), 0.84 (d, J=7.2, 3H), 0.91 (d, J=6.4, 2H), 0.99~1.15 (m, 2H), 1.41~2.33 (m, 15H), 2.8 (t, J=7.4, 1H), 4.77~4.87 (m, 1H), 5.44 (s, 1H), 6.86 (t, J=8.0, 1H), 7.18~7.23 (m, 1H), 7.26~7.31 (m, 1H).

Preparation Example 90: (R)-(8-chloro-4H-spiro[benzo[d][1,3]dioxine-2,1'-cyclopentan]-4-yl)methanol

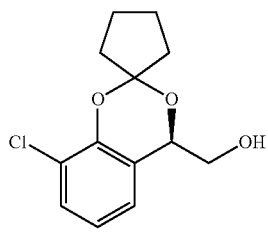 [SMILES: OC[C@@H]1OC2(CCCC2)Oc2c(Cl)cccc21]

The substantially same method as described in Preparation example 74 was conducted, except that (R)-((1S,2R,5S)-2-isopropyl-5-methylcyclohexyl) 8-chloro-4H-spiro[benzo[d][1,3]dioxine-2,1'-cyclopentane]-4-carboxylate (Preparation example 89) was used instead of (S)-((1R,2S,5R)-2-isopropyl-5-methylcyclohexyl) 8-chloro-2,2-dimethyl-4H-benzo[d][1,3]dioxine-4-carboxylate (Preparation example 73), to obtain the title compound. (1.9 g, 70~90%)

$^1$H NMR (400 MHz, CDCl$_3$) δ 1.72~1.98 (m, 4H), 2.02~2.17 (m, 4H), 2.21~2.30 (m, 1H), 3.78~3.88 (s, 1H), 4.01~4.09 (m, 1H), 4.96~5.06 (m, 1H), 6.87 (t, J=7.8, 1H), 6.96 (d, J=7.6, 1H), 7.26 (d, J=7.6, 1H)

Preparation Example 91: Ethyl 8-chloro-4H-spiro[benzo[d][1,3]dioxine-2,1'-cyclopentane]-4-carboxylate

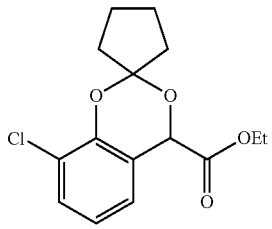 [SMILES: CCOC(=O)C1OC2(CCCC2)Oc2c(Cl)cccc21]

The substantially same method as described in Preparation example 87 was conducted, except that Ethyl 2-(3-chloro-2-hydroxyphenyl)-2-hydroxyacetate (Preparation example 78) was used instead of (R)-(1S,2R,5S)-2-isopropyl-5-methyl cyclohexyl 2-(3-chloro-2-hydroxyphenyl)-2-hydroxyacetate (Preparation example 75), to obtain the title compound. (2.5 g, 80~95%)

1H NMR (400 MHz, CDCl$_3$) δ 1.31 (t, J=7.1, 3H), 1.67~1.69 (m, 2H), 1.71~1.72 (m, 2H), 1.91~1.97 (m, 4H), 4.17 (q, J=7.1, 2H), 5.25~5.30 (m, 1H), 7.00 (dd, J=7.9, 1.3, 1H), 7.34 (dd, J=7.9, 7.5, 1H), 7.55 (dd, J=7.5, 1.3, 1H)

Preparation Example 92: (8-chloro-4H-spiro[benzo[d][1,3]dioxine-2,1'-cyclopentan]-4-yl)methanol

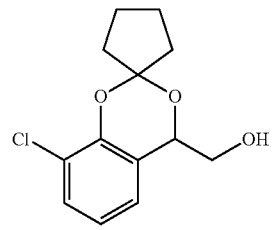 [SMILES: OCC1OC2(CCCC2)Oc2c(Cl)cccc21]

The substantially same method as described in Preparation example 74 was conducted, except that Ethyl 8-chloro-4H-spiro[benzo[d][1,3]dioxine-2,1'-cyclopentane]-4-carboxylate (Preparation example 91) was used instead of (S)-((1R,2S,5R)-2-isopropyl-5-methylcyclohexyl) 8-chloro-2,2-dimethyl-4H-benzo[d][1,3]dioxine-4-carboxylate (Preparation example 73), to obtain the title compound. (1.1 g, 70~90%)

$^1$H NMR (400 MHz, CDCl$_3$) δ 1.72~1.98 (m, 4H), 2.02~2.17 (m, 4H), 2.21~2.30 (m, 1H), 3.78~3.88 (s, 1H), 4.01~4.09 (m, 1H), 4.96~5.06 (m, 1H), 6.87 (t, J=7.8, 1H), 6.96 (d, J=7.6, 1H), 7.26 (d, J=7.6, 1H)

Preparation Example 93: (S)-((1R,2S,5R)-2-isopropyl-5-methylcyclohexyl) 8-chloro-4H-spiro[benzo[d][1,3]dioxine-2,1'-cyclohexane]-4-carboxylate

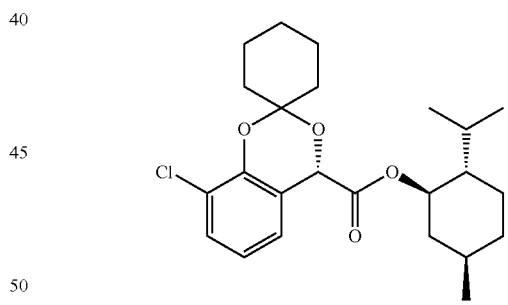

The substantially same method as described in Preparation example 87 was conducted, except that cyclohexanone was used instead of cyclopentanone, to obtain the title compound. (2.8 g, 80~95%)

1H NMR (400 MHz, CDCl$_3$) δ 0.88 (d, J=6.8, 3H), 0.88 (d, J=6.8, 3H), 0.92 (d, J=6.9, 3H), 1.34~1.36 (m, 2H), 1.46~50 (m, 5H), 1.52~1.59 (m, 4H), 1.67~1.79 (m, 6H), 1.85~1.97 (m, 2H), 5.09 (q, J=2.8, 1H), 5.55~5.59 (m, 1H), 7.01 (dd, J=7.9, J=1.3, 1H), 7.34 (dd, J=7.9, 7.5, 1H), 7.54 (dd, J=7.5, 1.3, 1H)

Preparation Example 94: (S)-(8-chloro-4H-spiro[benzo[d][1,3]dioxine-2,1'-cyclohexan]-4-yl)methanol

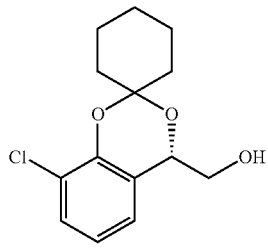 [SMILES: OC[C@H]1OC2(CCCCC2)Oc2c(Cl)cccc21]

The substantially same method as described in Preparation example 74 was conducted, except that (S)-((1R,2S,5R)-2-isopropyl-5-methylcyclohexyl) 8-chloro-4H-spiro[benzo[d][1,3]dioxine-2,1'-cyclohexane]-4-carboxylate (Preparation example 93) was used instead of (S)-((1R,2S,5R)-2-isopropyl-5-methylcyclohexyl) 8-chloro-2,2-dimethyl-4H-benzo[d][1,3]dioxine-4-carboxylate (Preparation example 73), to obtain the title compound. (2.3 g, 70~90%)

$^1$H NMR (400 MHz, CDCl$_3$) δ 1.52~1.58 (m, 3H), 1.74~1.92 (m, 6H), 1.98~2.06 (m, 1H), 2.12~2.15 (m, 1H), 3.81~3.86 (m, 1H), 4.03~4.09 (m, 1H), 4.99~5.01 (m, 1H), 6.87 (t, J=7.6, 1H), 6.95~6.98 (m, 1H), 7.27~7.29 (m, 1H)

Preparation Example 95: (R)-((1S,2R,5S)-2-isopropyl-5-methylcyclohexyl) 8-chloro-4H-spiro[benzo[d][1,3]dioxine-2,1'-cyclohexane]-4-carboxylate

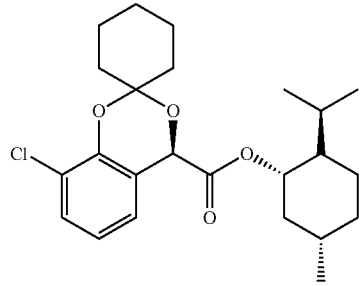

The substantially same method as described in Preparation example 89 was conducted, except that cyclohexanone was used instead of cyclopentanone, to obtain the title compound. (2.4 g, 80~95%)

$^1$H NMR (400 MHz, CDCl$_3$) δ 0.88 (d, J=6.8, 3H), 0.88 (d, J=6.8, 3H), 0.92 (d, J=6.9, 3H), 1.34~1.36 (m, 2H), 1.46~50 (m, 5H), 1.52~1.59 (m, 4H), 1.67~1.79 (m, 6H), 1.85~1.97 (m, 2H), 5.09 (q, J=2.8, 1H), 5.55~5.59 (m, 1H), 7.01 (dd, J=7.9, J=1.3, 1H), 7.34 (dd, J=7.9, 7.5, 1H), 7.54 (dd, J=7.5, 1.3, 1H)

Preparation Example 96: (R)-(8-chloro-4H-spiro[benzo[d][1,3]dioxine-2,1'-cyclohexan]-4-yl)methanol

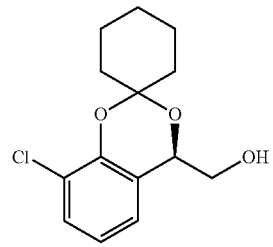 [SMILES: OC[C@@H]1OC2(CCCCC2)Oc2c(Cl)cccc21]

The substantially same method as described in Preparation example 74 was conducted, except (R)-((1S,2R,5S)-2-isopropyl-5-methylcyclohexyl) 8-chloro-4H-spiro[benzo[d][1,3]dioxine-2,1'-cyclohexane]-4-carboxylate (Preparation example 95) was used instead of (S)-((1R,2S,5R)-2-isopropyl-5-methylcyclohexyl) 8-chloro-2,2-dimethyl-4H-benzo[d][1,3]dioxine-4-carboxylate (Preparation example 73), to obtain the title compound. (2.1 g, 70~90%)

$^1$H NMR (400 MHz, CDCl$_3$) δ 1.52~1.58 (m, 3H), 1.74~1.92 (m, 6H), 1.98~2.06 (m, 1H), 2.12~2.15 (m, 1H), 3.81~3.86 (m, 1H), 4.03~4.09 (m, 1H), 4.99~5.01 (m, 1H), 6.87 (t, J=7.6, 1H), 6.95~6.98 (m, 1H), 7.27~7.29 (m, 1H)

Preparation Example 97: Ethyl 8-chloro-4H-spiro[benzo[d][1,3]dioxine-2,1'-cyclohexane]-4-carboxylate

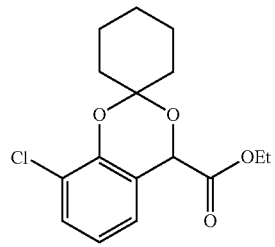 [SMILES: CCOC(=O)C1OC2(CCCCC2)Oc2c(Cl)cccc21]

The substantially same method as described in Preparation example 95 was conducted, except that Ethyl 2-(3-chloro-2-hydroxyphenyl)-2-hydroxyacetate (Preparation example 78) was used instead of that (R)-(1S,2R,5S)-2-isopropyl-5-methyl cyclohexyl 2-(3-chloro-2-hydroxyphenyl)-2-hydroxyacetate (Preparation example 75), to obtain the title compound. (2.2 g, 80~95%)

1H NMR (400 MHz, CDCl$_3$) δ 1.31 (t, J=7.1, 3H), 1.47~1.49 (m, 3H), 1.52~1.59 (m, 3H), 1.75~1.79 (m, 2H), 1.84~1.89 (m, 1H), 1.96~2.05 (m, 1H), 4.17 (q, J=7.1, 2H), 5.46~5.54 (m, 1H), 7.00 (dd, J=7.9, 1.3, 1H), 7.34 (dd, J=7.8, 7.5, 1H), 7.54 (dd, J=7.5, 1.3, 1H)

Preparation Example 98: (8-chloro-4H-spiro[benzo[d][1,3]dioxine-2,1'-cyclohexan]-4-yl)methanol

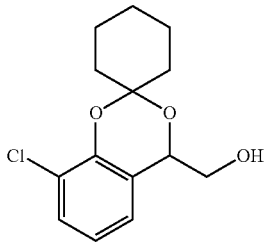 [SMILES: OCC1OC2(CCCCC2)Oc2c(Cl)cccc21]

The substantially same method as described in Preparation example 74 was conducted, except Ethyl 8-chloro-4H-spiro[benzo[d][1,3]dioxine-2,1'-cyclohexane]-4-carboxylate (Preparation example 97) was used instead of (S)-((1R,2S,5R)-2-isopropyl-5-methylcyclohexyl) 8-chloro-2,2-dimethyl-4H-benzo[d][1,3]dioxine-4-carboxylate (Preparation example 73), to obtain the title compound. (1.6 g, 70~90%)

1H NMR (400 MHz, CDCl$_3$) δ 1.52~1.58 (m, 3H), 1.74~1.92 (m, 6H), 1.98~2.06 (m, 1H), 2.12~2.15 (m, 1H), 3.81~3.86 (m, 1H), 4.03~4.09 (m, 1H), 4.99~5.01 (m, 1H), 6.87 (t, J=7.6, 1H), 6.95~6.98 (m, 1H), 7.27~7.29 (m, 1H)

Preparation Example 99: 3-chloro-2-hydroxybenzaldehyde

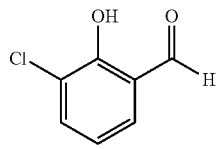

To a stirred solution of 2-chlorophenol (20.0 g, 155.60 mmol) in acetonitrile (200 mL) was added MgCl$_2$ (22.2 g, 233.35 mmol) and triethylamine (59.03 g, 583.39 mmol) at room temperature. The mixture was added paraformaldehyde (31.52 g, 1.05 mol) then refluxed for 4 hr. The resulting mixture was cooled to room temperature, quenched with 2N HCl, extracted with ether, dried over MgSO$_4$, filtered and concentrated under reduced pressure. The crude compound was purified by silica gel column chromatography to obtain the title compound. (16.7 g, 60~80%)

$^1$H NMR (400 MHz, CDCl$_3$) δ 7.01 (t, J=7.8, 1H), 7.49~7.56 (m, 1H), 7.63 (d, J=8.0, 1H), 9.91 (s, 1H), 11.50 (s, 1H).

Preparation Example 100: 2-(benzyloxy)-3-chlorobenzaldehyde

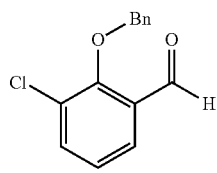 [SMILES: O=Cc1cccc(Cl)c1OCc1ccccc1]

To a stirred solution of 3-chloro-2-hydroxybenzaldehyde (Preparation example 99, 16.5 g, 106.98 mmol) in acetonitrile (165 mL) was added benzylbromide (19.21 g, 112.33 mmol) and K$_2$CO$_3$ (17.74 g, 128.38 mmol) at room temperature sequentially. The mixture was heated to reflux then stirred for 4 hr. The resulting mixture was cooled to room temperature, filtered through celite, and concentrated under reduced pressure. The crude compound was purified by a silica gel column to produce the title compound. (22.4 g, 80~95%).

$^1$H NMR (400 MHz, CDCl$_3$) δ 5.16 (s, 2H), 7.18~7.23 (m, 1H), 7.35~7.45 (m, 5H), 7.66~7.71 (m, 2H), 7.71~7.76 (m, 1H), 10.12 (d, J=0.8, 1H).

Preparation Example 101: Ethyl 3-(2-(benzyloxy)-3-chlorophenyl)-3-hydroxypropanoate

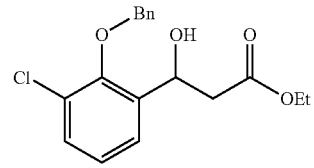 [SMILES: CCOC(=O)CC(O)c1cccc(Cl)c1OCc1ccccc1]

The substantially same method as described in Preparation example 62 was conducted, except that 2-(benzyloxy)-3-chlorobenzaldehyde (Preparation example 100) was used instead of 2-(2-(benzyloxy)phenyl)acetaldehyde (Preparation Example 61), to obtain the title compound. (1.9 g, 70~90%)

$^1$H NMR (400 MHz, CDCl$_3$) δ 1.24 (t, J=7.2, 1H), 2.55~2.80 (m, 2H), 3.30 (d, J=3.6, 1H), 4.15 (q, J=7.2, 2H), 4.98 (d, J=10.8, 1H), 5.16 (d, J=10.8, 1H), 5.29~5.34 (m, 1H), 7.12 (t, J=8.0, 1H), 7.34~7.55 (m, 8H).

Preparation Example 102: Ethyl 3-(3-chloro-2-hydroxyphenyl)-3-hydroxypropanoate

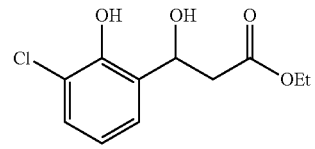 [SMILES: CCOC(=O)CC(O)c1cccc(Cl)c1O]

The substantially same method as described in Preparation example 63 was conducted, except that Ethyl 3-(2-(benzyloxy)-3-chlorophenyl)-3-hydroxypropanoate (Preparation example 101) was used instead of ethyl 4-(2-(benzyloxy)phenyl)-3-hydroxybutanoate (Preparation Example 62), to obtain the title compound. (3.6 g, 80~95%)

$^1$H NMR (400 MHz, CDCl$_3$) δ 1.28 (t, J=7.2, 1H), 2.70~2.90 (m, 2H), 4.20 (q, J=7.2, 2H), 4.33 (d, J=4.0, 1H), 5.30~5.40 (m, 1H), 6.83 (t, J=7.8, 1H,), 7.06~7.12 (m, 1H), 7.23~7.31 (m, 1H).

Preparation Example 103: Ethyl 2-(8-chloro-2,2-dimethyl-4H-benzo[d][1,3]dioxin-4-yl)acetate

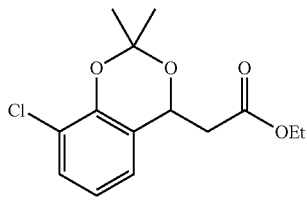 [SMILES: CCOC(=O)CC1OC(C)(C)Oc2c(Cl)cccc21]

To a stirred solution of ethyl 3-(3-chloro-2-hydroxyphenyl)-3-hydroxypropanoate (Preparation example 102, 2 g, 8.17 mmol) in THF (20 mL) was added 2-methoxypropene (1.6 mL, 16.34 mmol) and pyridinium p-toluenesulfonate (0.16 g, 0.82 mmol) then stirred at room temperature for 4 hr. The resulting mixture was diluted with dichloromethane, washed with water, dried over MgSO$_4$, filtered and concentrated under reduced pressure. The crude product was purified by silica gel column chromatography to produce the title compound. (2.0 g, 70~90%)

$^1$H NMR (400 MHz, CDCl$_3$) δ 1.30 (t, J=6.8, 3H), 1.54 (s, 3H), 1.66 (s, 3H), 2.71~2.77 (m, 1H), 2.89~2.94 (m, 1H), 4.23 (q, =6.8, 2H), 5.38~5.41 (m, 1H), 6.85 (t, J=8.0, 1H), 6.93 (d, J=8.0, 1H), 7.26~7.29 (m, 1H)

Preparation Example 104: 2-(8-chloro-2,2-dimethyl-4H-benzo[d][1,3]dioxin-4-yl)ethanol

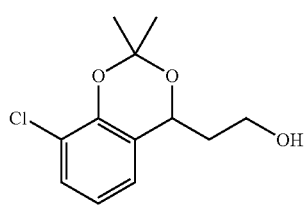 [SMILES: CC1(C)Oc2c(Cl)cccc2C(CCO)O1]

The substantially same method as described in Preparation example 65 was conducted, except that Ethyl 2-(8-chloro-2,2-dimethyl-4H-benzo[d][1,3]dioxin-4-yl)acetate (Preparation example 103) was used instead of ethyl 2-(2,2-dimethyl-4,5-dihydrobenzo[d][1,3]dioxepin-4-yl)acetate (Preparation Example 64), to obtain the title compound (1.6 g, 80~100%).

$^1$H NMR (400 MHz, CDCl$_3$), δ 1.53 (s, 3H), 1.69 (s, 3H), 2.0~2.08 (m, 1H), 2.28~2.36 (m, 1H), 3.80~3.85 (m, 2H), 5.16~5.18 (m, 1H), 6.87 (t, J=7.6, 1H), 6.95 (d, J=7.6, 1H), 7.26~7.28 (m, 1H).

Preparation Example 105: Ethyl 2-(8-chloro-2,2-diethyl-4H-benzo[d][1,3]dioxin-4-yl)acetate

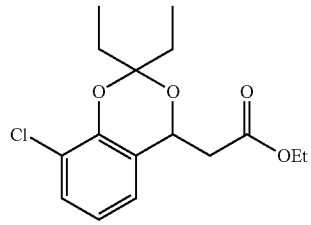 [SMILES: CCOC(=O)CC1OC(CC)(CC)Oc2c(Cl)cccc21]

The substantially same method as described in Preparation example 81 was conducted, except that Ethyl 3-(3-chloro-2-hydroxyphenyl)-3-hydroxypropanoate (Preparation example 102) was used instead of (S)-(1R,2S,5R)-2-isopropyl-5-methylcyclohexyl 2-(3-chloro-2-hydroxyphenyl)-2-hydroxyacetate (Preparation example 72), to obtain the title compound (1.5 g, 80~100%).

1H NMR (400 MHz, CDCl$_3$) δ 0.95 (t, J=7.6, 3H), 1.06 (t, J=7.6, 3H), 1.77~1.85 (m, 2H), 1.87~1.94 (m, 2H), 2.01~2.08 (m, 1H), 2.30~2.36 (m, 1H), 3.8~3.88 (m, 2H), 5.11~5.14 (m, 1H), 6.85 (t, J=8.0, 1H), 6.93 (d, J=7.6, 1H), 7.25~7.28 (m, 1H).

Preparation Example 106: 2-(8-chloro-2,2-dimethyl-4H-benzo[d][1,3]dioxin-4-yl)ethanol

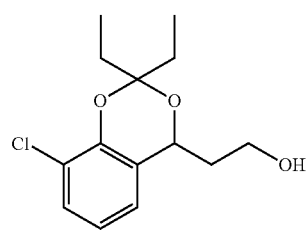 [SMILES: CCC1(CC)Oc2c(Cl)cccc2C(CCO)O1]

The substantially same method as described in Preparation example 65 was conducted, except that Ethyl 2-(8-chloro-2,2-diethyl-4H-benzo[d][1,3]dioxin-4-yl)acetate (Preparation example 105) was used instead of ethyl 2-(2,2-dimethyl-4,5-dihydrobenzo[d][1,3]dioxepin-4-yl)acetate (Preparation Example 64), to obtain the title compound (1.6 g, 80~100%).

1H NMR (400 MHz, CDCl$_3$) δ 0.96 (t, J=7.6, 3H), 1.0 (t, J=7.6, 3H), 1.29 (t, J=8.0, 3H), 1.78~1.9 (m, 4H), 2.68~2.74 (m, 1H), 2.91~2.95 (m, 1H), 4.22 (q, J=7.2, 2H), 5.33~5.36 (m, 1H), 6.82 (t, J=8.0, 1H), 6.91 (d, J=8.0, 1H), 7.25~7.27 (m, 1H).

Preparation Example 107: Ethyl 2-(8-chloro-4H-spiro[benzo[d][1,3]dioxine-2,1'-cyclopentane]-4-yl)acetate

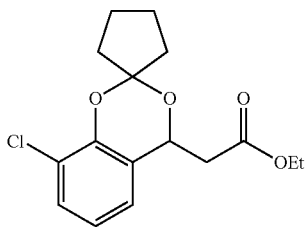 [SMILES: CCOC(=O)CC1OC2(CCCC2)Oc2c(Cl)cccc21]

The substantially same method as described in Preparation example 87 was conducted, except that Ethyl 3-(3-chloro-2-hydroxyphenyl)-3-hydroxypropanoate (Preparation example 102) was used instead of (S)-(1R,2S,5R)-2-isopropyl-5-methylcyclohexyl 2-(3-chloro-2-hydroxyphenyl)-2-hydroxyacetate (Preparation example 72), to obtain the title compound. (2.7 g, 40~60%)
$^1$H NMR (400 MHz, CDCl$_3$) δ 1.28 (t, J=7.0, 3H), 1.67~1.96 (m, 6H), 1.98~2.07 (m, 1H), 2.14~2.25 (m, 1H), 2.69~2.77 (m, 1H), 2.85~2.94 (m, 1H), 4.21 (q, J=7.2, 2H), 5.37~5.42 (m, 1H), 6.84 (t, J=7.8, 1H), 6.90 (d, 1=7.6, 1H), 7.25 (d, J=7.6, 1H)

Preparation Example 108: 2-(8-chloro-4H-spiro[benzo[d][1,3]dioxine-2,1'-cyclopentan]-4-yl)ethanol

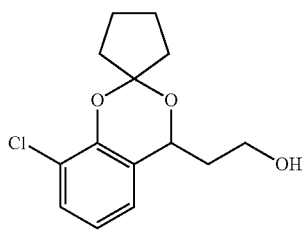 [SMILES: OCCC1OC2(CCCC2)Oc2c(Cl)cccc21]

The substantially same method as described in Preparation example 65 was conducted, except that Ethyl 2-(8-chloro-4H-spiro[benzo[d][1,3]dioxine-2,1'-cyclopentane]-4-yl)acetate (Preparation example 107) was used instead of ethyl 2-(2,2-dimethyl-4,5-dihydrobenzo[d][1,3]dioxepin-4-yl)acetate (Preparation Example 64), to obtain the title compound. (2.2 g, 80~100%)
$^1$H NMR (400 MHz, CDCl$_3$) δ 1.21~1.36 (m, 1H), 1.72~1.95 (m, 6H), 1.98~2.07 (m, 2H), 2.18~2.35 (m, 2H), 3.75~3.88 (m, 2H), 5.14~5.19 (m, 1H), 6.85 (t, J=7.8, 1H) 6.92 (d, J=7.6, 1H), 7.23~7.26 (m, 1H)

Preparation Example 109: Ethyl 2-(8-chloro-4H-spiro[benzo[d][1,3]dioxine-2,1'-cyclohexane]-4-yl)acetate

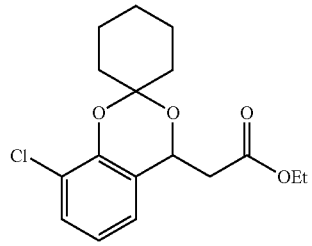 [SMILES: CCOC(=O)CC1OC2(CCCCC2)Oc2c(Cl)cccc21]

The substantially same method as described in Preparation example 93 was conducted, except that Ethyl 3-(3-chloro-2-hydroxyphenyl)-3-hydroxypropanoate (Preparation example 102) was used instead of (S)-(1R,2S,5R)-2-isopropyl-5-methylcyclohexyl 2-(3-chloro-2-hydroxyphenyl)-2-hydroxyacetate (Preparation example 72), to obtain the title compound. (3.6 g, 45~70%)
$^1$H NMR (400 MHz, CDCl$_3$) δ 1.28 (t, J=7.2, 3H), 1.43~1.95 (m, 12H), 2.65~2.75 (m, 1H), 2.85~2.95 (m, 1H), 4.21 (q, J=7.2, 2H), 5.35~5.40 (m, 1H), 6.81 (t, J=7.8, 1H), 6.86~6.92 (m, 1H), 7.23~2.27 (m, 1H).

Preparation Example 110: 2-(8-chloro-4H-spiro[benzo[d][1,3]dioxine-2,1'-cyclohexan]-4-yl)ethanol

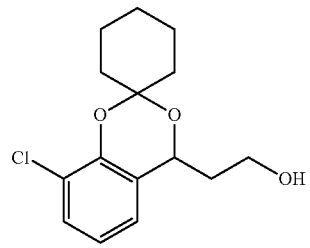 [SMILES: OCCC1OC2(CCCCC2)Oc2c(Cl)cccc21]

The substantially same method as described in Preparation example 65 was conducted, except that Ethyl 2-(8-chloro-4H-spiro[benzo[d][1,3]dioxine-2,1'-cyclohexane]-4-yl)acetate (Preparation example 109) was used instead of ethyl 2-(2,2-dimethyl-4,5-dihydrobenzo[d][1,3]dioxepin-4-yl)acetate (Preparation Example 64), to obtain the title compound. (2.6 g, 80~100%)
$^1$H NMR (400 MHz, CDCl$_3$) δ 1.42~1.63 (m, 4H), 1.64~1.75 (m, 1H), 1.75~1.91 (m, 4H), 2.92~2.08 (m, 2H), 2.25~2.50 (m, 2H), 3.78~3.92 (m, 2H), 5.12~5.19 (m, 1H), 6.85 (t, J=7.8, 1H), 6.92 (d, J=7.6, 1H), 7.23~7.28 (m, 1H).

Preparation Example 111: 2-(2-(benzyloxy)-3-chlorophenyl)acetaldehyde

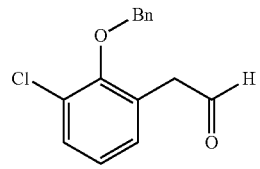 [SMILES: O=CCc1cccc(Cl)c1OCc1ccccc1]

The substantially same method as described in Preparation example 61 was conducted, except that 3-chloro-2-hydroxybenzaldehyde (Preparation example 99) was used instead of 2-(benzyloxy)benzaldehyde (Preparation Example 13), to obtain the title compound. (2.1 g, 55~70%)

1H NMR (400 MHz, CDCl₃) δ 3.72 (s, 2H), 5.12 (s, 2H), 6.92~7.03 (m, 1H) 7.19~7.21 (m, 1H), 7.25~7.39 (m, 2H), 7.40~7.47 (m, 4H), 9.87 (s, 1H)

Preparation Example 112: Ethyl 4-(2-(benzyloxy)-3-chlorophenyl)-3-hydroxybutanoate

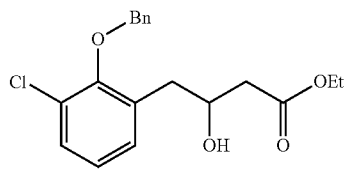 [SMILES: CCOC(=O)CC(O)Cc1cccc(Cl)c1OCc1ccccc1]

The substantially same method as described in Preparation example 62 was conducted, except that 2-(2-(benzyloxy)-3-chlorophenyl)acetaldehyde (Preparation example 111) was used instead of 2-(2-(benzyloxy)phenyl)acetaldehyde (Preparation Example 61), to obtain the title compound. (1.4 g, 70~90%)

$^1$H NMR (400 MHz, CDCl₃) δ 1.28 (t, J=7.2, 3H), 2.42~2.56 (m, 1H), 2.91~3.01 (m, 2H), 3.07 (d, J=4.0, 1H), 4.14 (q, J=7.2, 2H), 4.35~4.42 (m, 1H), 5.12 (s, 2H), 6.93~6.97 (m, 2H), 7.21~7.25 (m, 2H), 7.32~7.47 (m, 5H)

Preparation Example 113: Ethyl 4-(3-chloro-2-hydroxyphenyl)-3-hydroxybutanoate

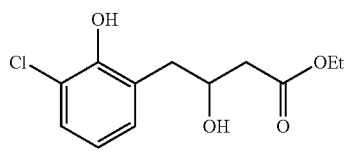 [SMILES: CCOC(=O)CC(O)Cc1cccc(Cl)c1O]

The substantially same method as described in Preparation example 63 was conducted, except that Ethyl 4-(2-(benzyloxy)-3-chlorophenyl)-3-hydroxybutanoate (Preparation example 112) was used instead of ethyl 4-(2-(benzyloxy)phenyl)-3-hydroxybutanoate (Preparation Example 62), to obtain the title compound. (1.1 g, 80~95%)

$^1$H NMR (400 MHz, CDCl₃) δ 1.29 (t, J=7.0, 3H), 2.41~2.52 (m, 2H), 2.81~3.01 (m, 2H), 3.05 (s, 1H), 4.03 (q, J=7.2, 2H), 4.26 (q, J=7.2, 1H), 5.11 (s, 1H), 6.93~6.97 (m, 1H), 7.21~7.25 (m, 1H), 7.29 (s, 1H)

Preparation Example 114: Ethyl 2-(9-chloro-2,2-dimethyl-4,5-dihydrobenzo[d][1,3]dioxepin-4-yl)acetate

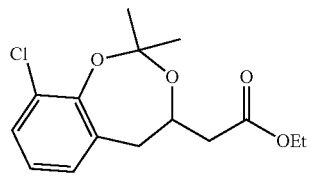 [SMILES: CCOC(=O)CC1Cc2cccc(Cl)c2OC(C)(C)O1]

The substantially same method as described in Preparation example 64 was conducted, except that Ethyl 4-(3-chloro-2-hydroxyphenyl)-3-hydroxybutanoate (Preparation example 113) was used instead of ethyl 3-hydroxy-4-(2-hydroxyphenyl)butanoate (Preparation Example 63), to obtain the title compound. (0.7 g, 70~90%)

$^1$H NMR (400 MHz, CDCl₃) δ 1.29 (t, J=7.0, 3H), 1.46 (s, 3H), 1.47 (s, 3H), 2.53 (dd, J=5.2, 15.2, 1H), 2.62 (dd, J=8.3, 15.2, 1H), 2.91~2.94 (m, 2H), 4.19 (q, J=6.0, 2H), 4.59~4.65 (m, 1H), 7.02~7.09 (m, 2H), 7.14~7.18 (m, 1H)

Preparation Example 115: 2-(9-chloro-2,2-dimethyl-4,5-dihydrobenzo[d][1,3]dioxepin-4-yl)ethanol

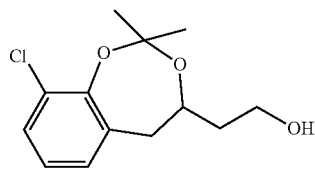 [SMILES: CC1(C)Oc2c(Cl)cccc2CC(CCO)O1]

The substantially same method as described in Preparation example 65 was conducted, except that Ethyl 2-(9-chloro-2,2-dimethyl-4,5-dihydrobenzo[d][1,3]dioxepin-4-yl)acetate (Preparation example 114) was used instead of ethyl 2-(2,2-dimethyl-4,5-dihydrobenzo[d][1,3]dioxepin-4-yl)acetate (Preparation Example 64), to obtain the title compound. (0.4 g, 80~100%)

$^1$H NMR (400 MHz, CDCl₃) δ 1.46 (s, 3H), 1.53 (s, 3H), 1.79~1.91 (m, 2H), 2.32~2.35 (m, 1H), 2.87 (dd, J=3.0, 15.4, 1H), 3.00 (dd, J=9.6, 15.2, 1H), 3.80~3.83 (m, 2H), 4.34~4.45 (m, 1H), 7.03~7.10 (m, 2H), 7.14~7.19 (m, 1H)

Preparation Example 116: Ethyl 2-(9-chloro-2,2-diethyl-4,5-dihydrobenzo[d][1,3]dioxepin-4-yl)acetate

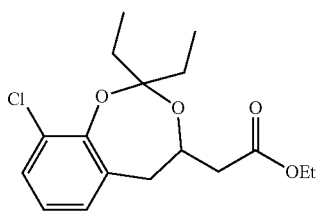 [SMILES: CCOC(=O)CC1Cc2cccc(Cl)c2OC(CC)(CC)O1]

The substantially same method as described in Preparation example 81 was conducted, except that Ethyl 4-(3-chloro-2-hydroxyphenyl)-3-hydroxybutanoate (Preparation example 113) was used instead of (S)-(1R,2S,5R)-2-isopropyl-5-methylcyclohexyl 2-(3-chloro-2-hydroxyphenyl)-2-hydroxyacetate (Preparation example 72), to obtain the title compound. (1.5 g, 60~80%)

$^1$H NMR (400 MHz, CDCl₃) δ 0.92~0.97 (m, 6H), 1.29 (t, J=7.0, 3H), 1.65~1.73 (m, 4H), 2.50 (dd, J=5.2, 15.2, 1H), 2.59 (dd, J=8.3, 15.2, 1H), 2.93~2.99 (m, 2H), 4.21 (q, J=6.0, 2H), 4.58~4.64 (m, 1H), 7.02~7.09 (m, 2H), 7.14~7.18 m, 1H)

Preparation Example 117: (9-chloro-2,2-diethyl-4,5-dihydrobenzo[d][1,3]dioxepin-4-yl)ethanol

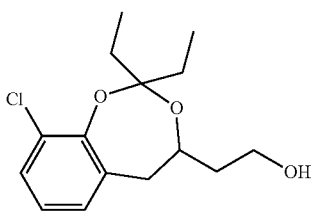 [SMILES: CCC1(CC)Oc2c(Cl)cccc2CC(CCO)O1]

The substantially same method as described in Preparation example 65 was conducted, except that Ethyl 2-(9-chloro-2,2-diethyl-4,5-dihydrobenzo[d][1,3]dioxepin-4-yl)acetate (Preparation example 116) was used instead of ethyl 2-(2,2-dimethyl-4,5-dihydrobenzo[d][1,3]dioxepin-4-yl)acetate (Preparation Example 64), to obtain the title compound. (1.1 g, 80~100%)

$^1$H NMR (400 MHz, CDCl$_3$) δ 0.90~0.96 (m, 6H), 1.61~1.70 (m, 4H), 1.80~1.89 (m, 2H), 2.33~2.35 (m, 1H), 2.93 (dd, J=3.0, 15.4, 1H), 3.06 (dd, J=9.6, 15.2, 1H), 3.78~3.83 (m, 2H), 4.37~4.43 (m, 1H), 7.02~7.09 (m, 2H), 7.14~7.18 (m, 1H)

Preparation Example 118: Ethyl 2-(9-chloro-4,5-dihydrospiro[benzo[d][1,3]dioxepine-2,1'-cyclopentan]4-yl)acetate

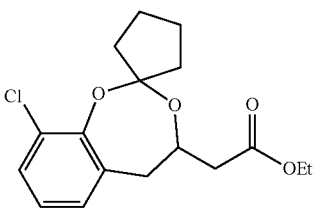 [SMILES: CCOC(=O)CC1Cc2cccc(Cl)c2OC2(CCCC2)O1]

The substantially same method as described in Preparation example 87 was conducted, except that Ethyl 4-(3-chloro-2-hydroxyphenyl)-3-hydroxybutanoate (Preparation example 113) was used instead of (S)-(1R,2S,5R)-2-isopropyl-5-methylcyclohexyl 2-(3-chloro-2-hydroxyphenyl)-2-hydroxyacetate (Preparation example 72), to obtain the title compound. (1.2 g, 60~80%)

$^1$H NMR (400 MHz, CDCl$_3$) δ 1.29 (t, J=7.0, 3H), 1.63~1.80 (m, 5H), 1.89~1.99 (m, 3H), 2.52 (dd, J=5.2, 15.2, 1H), 2.65 (dd, J=8.3, 15.2, 1H), 2.88~2.92 (m, 2H), 4.20 (q, J=6.0, 2H), 4.60~4.66 (m, 1H), 7.02~7.09 (m, 2H), 7.14~7.18 (m, 1H)

Preparation Example 119: (9-chloro-4,5-dihydrospiro[benzo[d][1,3]dioxepine-2,1'-cyclopentan]4-yl)ethanol

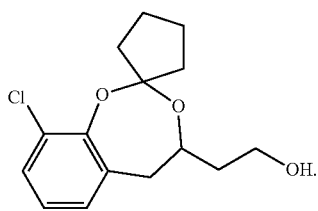 [SMILES: OCCC1Cc2cccc(Cl)c2OC2(CCCC2)O1]

The substantially same method as described in Preparation example 65 was conducted, except that Ethyl 2-(9-chloro-4,5-dihydrospiro[benzo[d][1,3]dioxepine-2,1'-cyclopentan]4-yl)acetate (Preparation example 118) was used instead of ethyl 2-(2,2-dimethyl-4,5-dihydrobenzo[d][1,3]dioxepin-4-yl)acetate (Preparation Example 64), to obtain the title compound. (0.7 g, 80~100%)

$^1$H NMR (400 MHz, CDCl$_3$) δ 1.67~1.74 (m, 3H), 1.80~1.87 (m, 5H), 1.80~1.93 (m, 2H), 2.31~2.35 (m, 1H), 2.88 (dd, J=3.0, 15.4, 1H), 3.00 (dd, J=9.6, 15.2, 1H), 3.80~3.86 (m, 2H), 4.33~4.40 (m, 1H), 7.02~7.09 (m, 2H), 7.14~7.18 (m, 1H)

Preparation Example 120: Ethyl 2-(9-chloro-4,5-dihydrospiro[benzo[d][1,3]dioxepine-2,1'-cyclohexan]4-yl)acetate

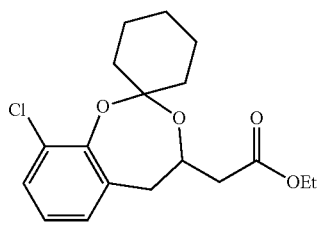 [SMILES: CCOC(=O)CC1Cc2cccc(Cl)c2OC2(CCCCC2)O1]

The substantially same method as described in Preparation example 93 was conducted, except that Ethyl 4-(3-chloro-2-hydroxyphenyl)-3-hydroxybutanoate (Preparation example 113) was used instead of (S)-(1R,2S,5R)-2-isopropyl-5-methyl cyclohexyl 2-(3-chloro-2-hydroxyphenyl)-2-hydroxyacetate (Preparation example 72), to obtain the title compound. (1.0 g, 60~80%)

$^1$H NMR (400 MHz, CDCl$_3$) δ 1.29 (t, J=7.0, 3H), 1.53~1.65 (m, 10H), 2.49 (dd, J=5.2, 15.2, 1H), 2.58 (dd, J=8.3, 15.2, 1H), 2.93~2.99 (m, 2H), 4.21 (q, J=6, 2H), 4.58~4.63 (m, 1H), 7.02~7.09 (m, 2H), 7.14~7.18 (m, 1H).

Preparation Example 121: (9-chloro-4,5-dihydrospiro[benzo[d][1,3]dioxepine-2,1'-cyclohexan]4-yl)ethanol

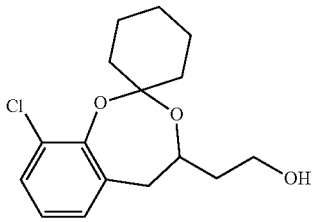 [SMILES: OCCC1Cc2cccc(Cl)c2OC2(CCCCC2)O1]

The substantially same method as described in Preparation example 65 was conducted, except that Ethyl 2-(9-chloro-4,5-dihydrospiro[benzo[d][1,3]dioxepine-2,1'-cyclopentan]4-yl)acetate (Preparation example 120) was used instead of ethyl 2-(2,2-dimethyl-4,5-dihydrobenzo[d][1,3]dioxepin-4-yl)acetate (Preparation Example 64), to obtain the title compound. (0.6 g, 80~100%)

$^1$H NMR (400 MHz, CDCl$_3$) δ 1.54~1.66 (m, 10H), 1.81~1.90 (m, 2H). 2.31~2.35 (m, 1H), 2.91 (dd, J=3.0, 15.4, 1H), 3.08 (dd, J=9.6, 15.2, 1H), 3.78~3.82 (m, 2H), 4.36~4.43 (m, 1H), 7.02~7.09 (m, 2H), 7.14~7.18 (m, 1H)

Preparation Example 122: Ethyl 2-(4-chloro-2-hydroxyphenyl)-2-hydroxyacetate

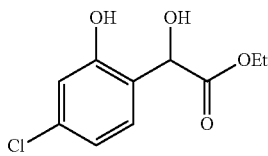 [SMILES: CCOC(=O)C(O)c1ccc(Cl)cc1O]

The substantially same method as described in Preparation example 78 was conducted, except that 3-chlorophenol was used instead of 2-chlorophenol, to obtain the title compound. (0.6 g, 45~70%)

$^1$H NMR (400 MHz, CDCl$_3$) δ 1.42 (t, J=6.4, 3H), 4.05 (s, 1H), 4.06~4.31 (m, 2H), 5.27 (s, 1H), 6.74~6.88 (m, 2H), 6.94~7.27 (m, 1H), 7.68 (s, 1H).

Preparation Example 123: Ethyl 7-chloro-2,2-dimethyl-4H-benzo[d][1,3]dioxine-4-carboxylate

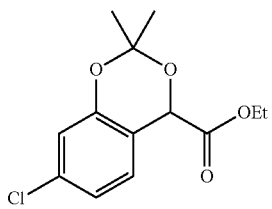 [SMILES: CCOC(=O)C1OC(C)(C)Oc2cc(Cl)ccc21]

The substantially same method as described in Preparation example 79 was conducted, except that Ethyl 2-(4-chloro-2-hydroxyphenyl)-2-hydroxyacetate (Preparation example 122) was used instead of Ethyl 2-(3-chloro-2-hydroxyphenyl)-2-hydroxyacetate (Preparation example 78), to obtain the title compound. (0.6 g, 80~95%)

$^1$H NMR (400 MHz, CDCl$_3$) δ 1.42 (t, J=6.4, 3H), 1.52 (s, 3H), 1.63 (s, 3H), 4.06~4.31 (m, 2H), 4.96 (s, 1H), 6.91~6.96 (m, 1H), 7.04~7.06 (m, 1H), 7.17~7.22 (m, 1H).

Preparation Example 124: (7-chloro-2,2-dimethyl-4H-benzo[d][1,3]dioxin-4-yl)methanol

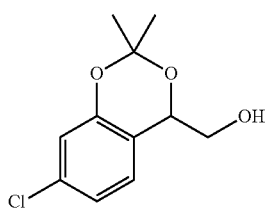

The substantially same method as described in Preparation example 80 was conducted, except that Ethyl 7-chloro-2,2-dimethyl-4H-benzo[d][1,3]dioxine-4-carboxylate (Preparation example 123) was used instead of Ethyl 8-chloro-2,2-dimethyl-4H-benzo[d][1,3]dioxine-4-carboxylate (Preparation example 79), to obtain the title compound. (0.4 g, 70~90%)

$^1$H NMR (400 MHz, CDCl$_3$) δ 1.52 (s, 3H), 1.63 (s, 3H), 2.19 (q, J=4.4, 1H), 3.80~3.86 (m, 1H), 4.03~4.09 (m, 1H), 5.00 (q, J=3.2, 1H), 6.85 (dd, J=1.0, 8.2, 1H), 7.04~7.06 (m, 1H), 7.17~7.22 (m, 1H).

Preparation Example 125: (R)-((1S,2R,5S)-2-isopropyl-5-methylcyclohexyl) 2-(5-chloro-2-hydroxyphenyl)-2-hydroxyacetate

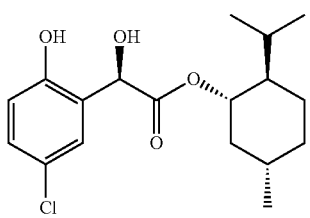 [SMILES: CC(C)[C@H]1CC[C@H](C)C[C@@H]1OC(=O)[C@H](O)c1cc(Cl)ccc1O]

The substantially same method as described in Preparation example 75 was conducted, except that 4-chlorophenol was used instead of 2-chlorophenol, to obtain the title compound (5.2 g, 45~70%)

$^1$H NMR (400 MHz, CDCl$_3$) δ 0.76~0.73 (m, 2H), 0.93~0.85 (m, 5H), 1.48~1.44 (m, 4H), 1.60 (S, 3H), 1.63 (S, 3H), 2.06~1.71 (m, 3H), 4.86~4.78 (m, 1H), 5.43 (s, 1H), 6.86 (t, J=8.0, 1H), 7.2 (d, J=9.2, 1H), 7.29 (d, J=5.6, 1H).

Preparation Example 126: (R)-((1S,2R,5S)-2-isopropyl-5-methylcyclohexyl) 6-chloro-2,2-dimethyl-4H-benzo[d][1,3]dioxine-4-carboxylate

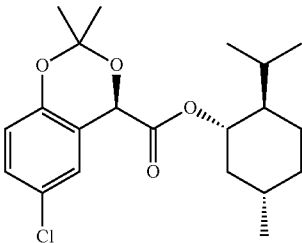 [SMILES: CC(C)[C@H]1CC[C@H](C)C[C@@H]1OC(=O)[C@@H]1OC(C)(C)Oc2ccc(Cl)cc21]

The substantially same method as described in Preparation example 76 was conducted, except that (R)-((1S,2R,5S)-2-isopropyl-5-methylcyclohexyl) 2-(5-chloro-2-hydroxyphenyl)-2-hydroxyacetate (Preparation example 125) was used instead of (S)-((1R,2S,5R)-2-isopropyl-5-methylcyclohexyl) 2-(3-chloro-2-hydroxyphenyl)-2-hydroxyacetate (Preparation example 72), to obtain the title compound. (1.7 g, 80~95%)

$^1$H NMR (400 MHz, CDCl$_3$) δ 0.73~0.76 (m, 2H), 0.85~0.93 (m, 8H), 1.02~1.14 (m, 2H), 1.44~1.48 (m, 5H), 1.60 (s, 3H), 1.63 (s, 3H), 1.71~1.94 (m, 2H), 1.71~2.06 (m, 4H), 4.86~4.80 (m, 1H), 5.36 (d, J=4.8, 1H), 6.77 (d, J=8.8, 1H), 7.17 (dd, J=8.8, 2, 1H), 7.34 (dd, J=10.8, 1.6, 1H).

Preparation Example 127: (R)-(6-chloro-2,2-dimethyl-4H-benzo[d][1,3]dioxin-4-yl)methanol

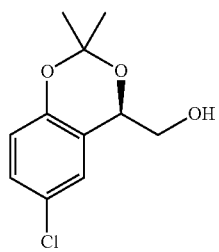

The substantially same method as described in Preparation example 74 was conducted, except that (R)-((1S,2R,5S)-2-isopropyl-5-methylcyclohexyl) 6-chloro-2,2-dimethyl-4H-benzo[d][1,3]dioxine-4-carboxylate (Preparation example 126) was used instead of (S)-((1R,2S,5R)-2-isopropyl-5-methylcyclohexyl) 8-chloro-2,2-dimethyl-4H-benzo[d][1,3]dioxine-4-carboxylate (Preparation example 73), to obtain the title compound. (2.1 g, 70~90%)

$^1$H NMR (400 MHz, CDCl$_3$) δ 1.62 (s, 3H), 1.68 (s, 3H), 3.86~3.77 (m, 1H), 4.19~4.12 (m, 1H), 4.95 (tq, J=3.2, 1H), 6.08 (d, J=5.6, 1H), 7.06 (d, J=2.4, 1H), 7.16 (dd, J=9.6, 8.4, 1H).

Preparation Example 128: (S)-((1R,2S,5R)-2-isopropyl-5-methylcyclohexyl) 2-(5-chloro-2-hydroxyphenyl)-2-hydroxyacetate

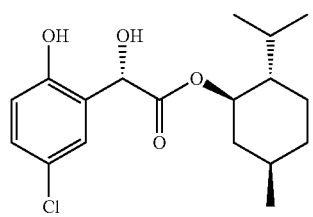 [SMILES: CC(C)[C@@H]1CC[C@@H](C)C[C@H]1OC(=O)[C@@H](O)c1cc(Cl)ccc1O]

The substantially same method as described in Preparation example 72 was conducted, except that 4-chlorophenol was used instead of 2-chlorophenol, to obtain the title compound (4.8 g, 45~70%)

$^1$H NMR (400 MHz, CDCl$_3$) δ 0.73~0.76 (m, 2H), 0.85~0.93 (m, 5H), 1.44~1.48 (m, 4H), 1.60 (s, 3H), 1.63 (s, 3H), 1.71~2.06 (m, 3H), 4.78~4.86 (m, 1H), 5.43 (s, 1H), 6.86 (t, J=8.0, 1H), 7.20 (d, J=9.2, 1H), 7.29 (d, J=5.6, 1H).

Preparation Example 129: (S)-((1R,2S,5R)-2-isopropyl-5-methylcyclohexyl) 6-chloro-2,2-dimethyl-4H-benzo[d][1,3]dioxine-4-carboxylate

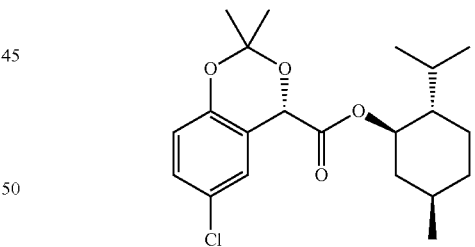

The substantially same method as described in Preparation example 76 was conducted, except that ((S)-((1R,2S,5R)-2-isopropyl-5-methylcyclohexyl) 2-(5-chloro-2-hydroxyphenyl)-2-hydroxyacetate (Preparation example 128) was used instead of (S)-((1R,2S,5R)-2-isopropyl-5-methylcyclohexyl) 2-(3-chloro-2-hydroxyphenyl)-2-hydroxyacetate (Preparation example 72), to obtain the title compound (4.9 g, 80~95%)

$^1$H NMR (400 MHz, CDCl$_3$) δ 0.73~0.76 (m, 2H), 0.85~0.93 (m, 8H), 1.02~1.14 (m, 2H), 1.44~1.48 (m, 5H), 1.60 (s, 3H), 1.63 (s, 3H), 1.71~1.94 (m, 2H), 1.71~2.06 (m, 4H), 4.86~4.80 (m, 1H), 5.36 (d, J=4.8, 1H), 6.77 (d, J=8.8, 1H), 7.17 (dd, J=8.8, 2, 1H), 7.34 (dd, J=10.8, 1.6, 1H).

Preparation Example 130: (S)-(6-chloro-2,2-dimethyl-4H-benzo[d][1,3]dioxine-4-yl)methanol

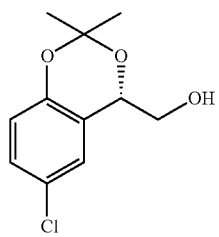

The substantially same method as described in Preparation example 74 was conducted, except that (S)-((1R,2S,5R)-2-isopropyl-5-methylcyclohexyl) 6-chloro-2,2-dimethyl-4H-benzo[d][1,3]dioxine-4-carboxylate (Preparation example 129) was used instead of (S)-((1R,2S,5R)-2-isopropyl-5-methylcyclohexyl) 8-chloro-2,2-dimethyl-4H-benzo[d][1,3]dioxine-4-carboxylate (Preparation example 73), to obtain the title compound. (2.4 g, 70~90%)

$^1$H NMR (400 MHz, CDCl$_3$) δ 1.62 (s, 3H), 1.68 (s, 3H), 3.86~3.77 (m, 1H), 4.19~4.12 (m, 1H), 4.95 (qt. J=3.2, 1H), 6.08 (d, J=5.6, 1H), 7.06 (d, J=2.4, 1H), 7.16 (dd, J=9.6, 8.4, 1H).

Preparation Example 131: Ethyl 2-(5-chloro-2-hydroxyphenyl)-2-hydroxyacetate

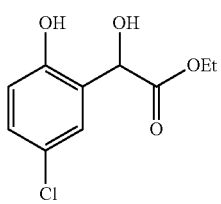 [SMILES: CCOC(=O)C(O)c1cc(Cl)ccc1O]

The substantially same method as described in Preparation example 78 was conducted, except that 4-chlorophenol was used instead of 2-chlorophenol, to obtain the title compound. (6.3 g, 45~70%)

1H NMR (400 MHz, CDCl$_3$) δ=1.42 (t, J=6.4, 3H), 4.05 (s, 1H), 4.06~4.31 (m, 2H), 5.27 (s, 1H), 6.74~6.88 (m, 2H), 7.20~7.27 (m, 1H), 7.39 (s, 1H).

Preparation Example 132: Ethyl 6-chloro-2,2-dimethyl-4H-benzo[d][1,3]dioxine-4-carboxylate

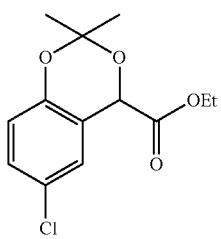 [SMILES: CCOC(=O)C1OC(C)(C)Oc2ccc(Cl)cc21]

The substantially same method as described in Preparation example 79 was conducted, except that Ethyl 2-(5-chloro-2-hydroxyphenyl)-2-hydroxyacetate (Preparation example 131) was used instead of Ethyl 2-(3-chloro-2-hydroxyphenyl)-2-hydroxyacetate (Preparation example 78), to obtain the title compound. (5.69 g, 80~95%)

1H NMR (400 MHz, CDCl$_3$) δ=1.42 (t, J=6.4, 3H), 1.52 (s, 3H), 1.63 (s, 3H), 4.06~4.31 (m, 2H), 4.96 (s, 1H), 6.82~6.90 (m, 1H), 7.28~7.26 (m, 1H), 7.45 (m, 1H).

Preparation Example 133: (6-chloro-2,2-dimethyl-4H-benzo[d][1,3]dioxin-4-yl)methanol

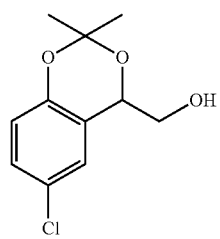

The substantially same method as described in Preparation example 80 was conducted, except that Ethyl 6-chloro-2,2-dimethyl-4H-benzo[d][1,3]dioxine-4-carboxylate (Preparation example 132) was used instead of Ethyl 8-chloro-2,2-dimethyl-4H-benzo[d][1,3]dioxine-4-carboxylate (Preparation example 79), to obtain the title compound. (3.0 g, 70~90%)

1H NMR (400 MHz, CDCl$_3$) δ=1.62 (s, 3H), 1.68 (s, 3H), 3.86~3.77 (m, 1H), 4.19~4.12 (m, 1H), 4.95 (qt, J=3.2, 1H), 6.08 (d, J=5.6, 1H), 7.06 (d, J=2.4, 1H), 7.46 (s, 1H).

Preparation Example 134: (R)-((1S,2R,5S)-2-isopropyl-5-methylcyclohexyl) 6-chloro-2,2-diethyl-4H-benzo[d][1,3]dioxine-4-carboxylate

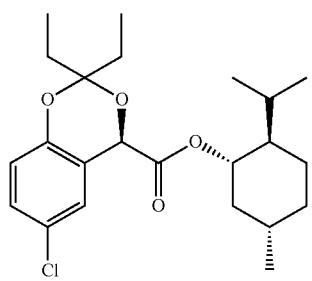 [SMILES: CCC1(CC)Oc2ccc(Cl)cc2[C@H](C(=O)O[C@H]2C[C@@H](C)CC[C@@H]2C(C)C)O1]

The substantially same method as described in Preparation example 81 was conducted, except that (R)-((1S,2R,5S)-2-isopropyl-5-methylcyclohexyl) 2-(5-chloro-2-hydroxyphenyl)-2-hydroxyacetate (Preparation example 125) was used instead of (S)-((1R,2S,5R)-2-isopropyl-5-methylcyclohexyl) 2-(3-chloro-2-hydroxyphenyl)-2-hydroxyacetate (Preparation example 72), to obtain the title compound. (2.3 g, 80~95%)

1H NMR (400 MHz, CDCl$_3$) δ 0.64~2.10 (m, 28H), 4.70~4.85 (m, 1H), 5.37 (s, 1H), 6.83 (t, J=7.8, 1H), 6.82~6.90 (m, 1H), 7.28~7.31 (m, 1H), 7.45 (s, 1H).

Preparation Example 135: (R)-(6-chloro-2,2-di-ethyl-4H-benzo[d][1,3]dioxin-4-yl)methanol

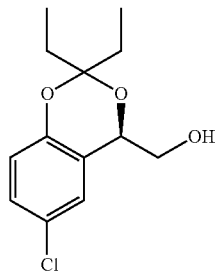 [SMILES: CCC1(CC)Oc2ccc(Cl)cc2[C@H](CO)O1]

The substantially same method as described in Preparation example 74 was conducted, except that (R)-((1S,2R,5S)-2-isopropyl-5-methylcyclohexyl) 6-chloro-2,2-diethyl-4H-benzo[d][1,3]dioxine-4-carboxylate (Preparation example 134) was used instead of (S)-((1R,2S,5R)-2-isopropyl-5-methylcyclohexyl) 8-chloro-2,2-dimethyl-4H-benzo[d][1,3]dioxine-4-carboxylate (Preparation example 73), to obtain the title compound. (1.5 g, 70~90%)

1H NMR (400 MHz, CDCl$_3$) δ 0.93 (t, J=7.6, 3H), 1.06 (t, J=7.4, 3H), 1.71~1.86 (m, 2H), 1.86~1.97 (m, 2H), 2.13 (q, J=4.4, 1H), 3.77~3.86 (m, 1H), 4.00~4.08 (m, 1H), 4.91~4.97 (m, 1H), 6.82~6.90 (m, 1H), 7.28~7.31 (m, 1H), 7.45 (s, 1H).

Preparation Example 136: (S)-((1R,2S,5R)-2-isopropyl-5-methylcyclohexyl) 6-chloro-2,2-diethyl-4H-benzo[d][1,3]dioxine-4-carboxylate

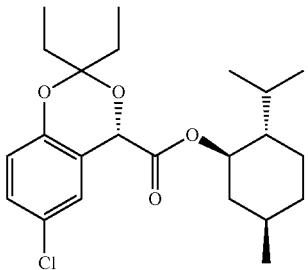 [SMILES: CCC1(CC)Oc2ccc(Cl)cc2[C@@H](C(=O)O[C@@H]2C[C@H](C)CC[C@H]2C(C)C)O1]

The substantially same method as described in Preparation example 81 was conducted, except that (S)-((1R,2S,5R)-2-isopropyl-5-methylcyclohexyl) 2-(5-chloro-2-hydroxyphenyl)-2-hydroxyacetate (Preparation example 128) was used instead of (S)-((1R,2S,5R)-2-isopropyl-5-methylcyclohexyl) 2-(3-chloro-2-hydroxyphenyl)-2-hydroxyacetate (Preparation example 72), to obtain the title compound. (2.0 g, 80~95%)

1H NMR (400 MHz, CDCl$_3$) δ 0.64~2.10 (m, 28H), 4.70~4.85 (m, 1H), 5.37 (s, 1H), 6.83 (t, J=7.8, 1H), 6.82~6.90 (m, 1H), 7.28~7.31 (m, 1H), 7.45 (s, 1H).

Preparation Example 137: (S)-(6-chloro-2,2-diethyl-4H-benzo[d][1,3]dioxin-4-yl)methanol

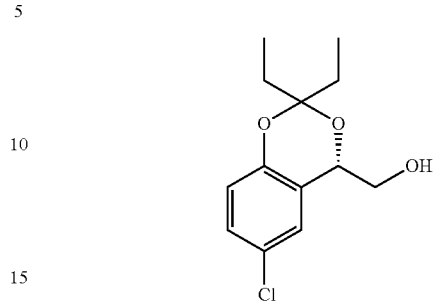

The substantially same method as described in Preparation example 74 was conducted, except that (S)-((1R,2S,5R)-2-isopropyl-5-methylcyclohexyl) 6-chloro-2,2-diethyl-4H-benzo[d][1,3]dioxine-4-carboxylate (Preparation example 136) was used instead of (S)-((1R,2S,5R)-2-isopropyl-5-methylcyclohexyl) 8-chloro-2,2-dimethyl-4H-benzo[d][1,3]dioxine-4-carboxylate (Preparation example 73), to obtain the title compound. (1.6 g, 70~90%)

1H NMR (400 MHz, CDCl$_3$) δ 0.93 (t, J=7.6, 3H), 1.06 (t, J=7.40, 3H), 1.71~1.86 (m, 2H), 1.86~1.97 (m, 2H), 2.13 (q, J=4.4, 1H), 3.77~3.86 (m, 1H), 4.00~4.08 (m, 1H), 4.91~4.97 (m, 1H), 6.82~6.90 (m, 1H), 7.28~7.31 (m, 1H), 7.45 (s, 1H).

Preparation Example 138: Ethyl 6-chloro-2,2-diethyl-4H-benzo[d][1,3]dioxine-4-carboxylate

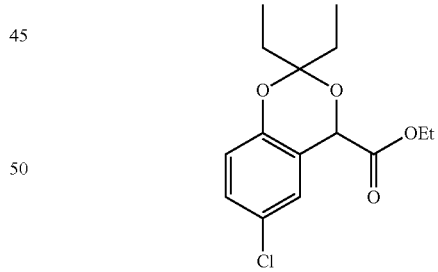

The substantially same method as described in Preparation example 81 was conducted, except that Ethyl 2-(5-chloro-2-hydroxyphenyl)-2-hydroxyacetate (Preparation example 131) was used instead of (S)-(1R,2S,5R)-2-isopropyl-5-methylcyclohexyl 2-(3-chloro-2-hydroxyphenyl)-2-hydroxyacetate (Preparation example 72), to obtain the title compound. (0.9 g, 80~95%)

1H NMR (400 MHz, CDCl$_3$) δ 0.93 (t, J=7.6, 3H), 1.06 (t, J=7.4, 3H), 1.42 (t, J=6.4, 3H), 1.71~1.86 (m, 2H), 1.86~1.97 (m, 2H), 4.06~4.31 (m, 2H), 4.96 (s, 1H), 6.92~6.97 (m, 1H), 7.22~7.28 (m, 1H), 7.44 (s, 1H).

Preparation Example 139: (6-chloro-2,2-diethyl-4H-benzo[d][1,3]dioxin-4-yl)methanol

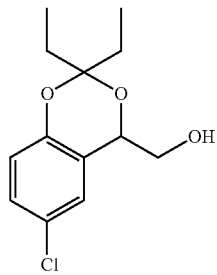 [SMILES: CCC1(CC)Oc2ccc(Cl)cc2C(CO)O1]

The substantially same method as described in Preparation example 80 was conducted, except that Ethyl 6-chloro-2,2-diethyl-4H-benzo[d][1,3]dioxine-4-carboxylate (Preparation example 138) was used instead of Ethyl 8-chloro-2,2-dimethyl-4H-benzo[d][1,3]dioxine-4-carboxylate (Preparation example 79), to obtain the title compound. (1.0 g, 70~90%)

1H NMR (400 MHz, CDCl$_3$) δ 0.93 (t, J=7.6, 3H), 1.06 (t, J=7.4, 3H), 1.71~1.86 (m, 2H), 1.86~1.97 (m, 2H), 2.13 (q, J=4.40), 3.77~3.86 (m, 1H), 4.00~4.08 (m, 1H), 4.91~4.97 (m, 1H), 6.82~6.90 (m, 1H), 7.28~7.31 (m, 1H), 7.45 (s, 1H).

Preparation Example 140: Ethyl 6-chloro-4H-spiro[benzo[d][1,3]dioxine-2,1'-cyclopentan]-4-carboxylate

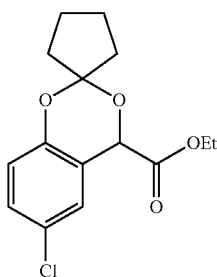 [SMILES: CCOC(=O)C1OC2(CCCC2)Oc2ccc(Cl)cc21]

The substantially same method as described in Preparation example 87 was conducted, except that Ethyl 6-chloro-2,2-diethyl-4H-benzo[d][1,3]dioxine-4-carboxylate (Preparation example 138) was used instead of (S)-(1R,2S,5R)-2-isopropyl-5-methylcyclohexyl 2-(3-chloro-2-hydroxyphenyl)-2-hydroxyacetate (Preparation example 72), to obtain the title compound. (2.7 g, 80~95%)

1H NMR (400 MHz, CDCl$_3$) δ 1.31 (t, J=7.1, 3H), 1.67~1.70 (m, 4H), 1.89~1.95 (m, 4H), 4.14~4.20 (m, 2H), 5.25 (s, 1H), 6.99~7.07 (m, 3H)

Preparation Example 141: (6-chloro-4H-spiro[benzo[d][1,3]dioxine-2,1'-cyclopentan]-4-yl)methanol

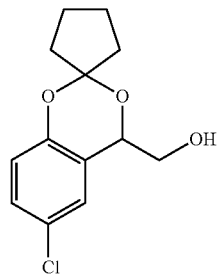 [SMILES: OCC1OC2(CCCC2)Oc2ccc(Cl)cc21]

The substantially same method as described in Preparation example 80 was conducted, except that Ethyl 6-chloro-4H-spiro[benzo[d][1,3]dioxine-2,1'-cyclopentan]-4-carboxylate (Preparation example 140) was used instead of Ethyl 8-chloro-2,2-dimethyl-4H-benzo[d][1,3]dioxine-4-carboxylate (Preparation example 79), to obtain the title compound. (1.0 g, 70~90%)

1H NMR (400 MHz, CDCl$_3$) δ 1.62~1.75 (m, 4H), 1.86~1.98 (m, 4H), 4.02 (d, J=4.4, 2H), 4.79 (t, J=4.4, 1H), 7.00~7.38 (m, 3H)

Preparation Example 142: Ethyl 6-chloro-4H-spiro[benzo[d][1,3]dioxine-2,1'-cyclohexane]-4-carboxylate

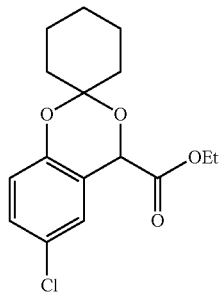 [SMILES: CCOC(=O)C1OC2(CCCCC2)Oc2ccc(Cl)cc21]

The substantially same method as described in Preparation example 93 was conducted, except that Ethyl 6-chloro-2,2-diethyl-4H-benzo[d][1,3]dioxine-4-carboxylate (Preparation example 138) was used instead of (S)-(1R,2S,5R)-2-isopropyl-5-methylcyclohexyl 2-(3-chloro-2-hydroxyphenyl)-2-hydroxyacetate (Preparation example 72), to obtain the title compound. (2.7 g, 80~95%).

1H NMR (400 MHz, CDCl$_3$) δ 1.30 (t, J=7.12, 3H), 1.47~1.59 (m, 6H), 1.75~1.96 (m, 4H), 4.17 (q, J=7.11, 2H), 5.45 (s, 1H), 7.01~7.11 (m, 3H).

Preparation Example 143: (6-chloro-4H-spiro[benzo[d][1,3]dioxine-2,1'-cyclohexan]-4-yl)methanol

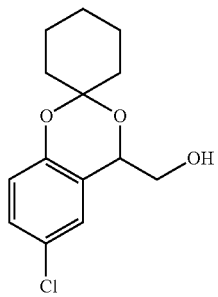 [SMILES: OCC1OC2(CCCCC2)Oc2ccc(Cl)cc21]

The substantially same method as described in Preparation example 80 was conducted, except that Ethyl 6-chloro-4H-spiro[benzo[d][1,3]dioxine-2,1'-cyclohexan]-4-carboxylate (Preparation example 142) was used instead of Ethyl 8-chloro-2,2-dimethyl-4H-benzo[d][1,3]dioxine-4-carboxylate (Preparation example 79), to obtain the title compound. (1.0 g, 70~90%).

1H NMR (400 MHz, CDCl$_3$) δ 1.47~1.59 (m, 6H), 1.74~1.93 (m, 4H), 1.02 (d, J=5.2, 2H), 5.12 (t, J=5.24, 1H), 7.01~7.38 (m, 3).

Preparation Example 144: Ethyl 2-(5-fluoro-2-hydroxyphenyl)-2-hydroxyacetate

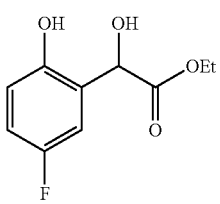 [SMILES: CCOC(=O)C(O)c1cc(F)ccc1O]

The substantially same method as described in Preparation example 78 was conducted, except that 4-fluorophenol was used instead of 2-chlorophenol, to obtain the title compound (5.2 g, 50~70%)

$^1$H NMR (400 MHz, CDCl$_3$) δ 1.28 (t, J=8.0, 3H), 4.32~4.15 (m, 2H), 5.30 (s, 1H), 6.86~6.83 (m, 1H), 6.98~6.91 (m, 2H)

Preparation Example 145: Ethyl 6-fluoro-2,2-dimethyl-4H-benzo[d][1,3]dioxine-4-carboxylate

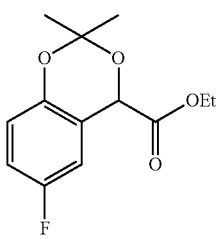 [SMILES: CCOC(=O)C1OC(C)(C)Oc2ccc(F)cc21]

The substantially same method as described in Preparation example 79 was conducted, except that Ethyl 2-(5-fluoro-2-hydroxyphenyl)-2-hydroxyacetate (Preparation example 144) was used instead of Ethyl 2-(3-chloro-2-hydroxyphenyl)-2-hydroxyacetate (Preparation example 78), to obtain the title compound. (5.2 g, 80~95%)

$^1$H NMR (400 MHz, CDCl$_3$) δ 1.36 (t, J=8.0, 3H) 1.53 (s, 3H) 1.64 (s, 3H) 4.33 (q, J=6.0, 2H) 5.42 (s, 1H) 6.88~6.79 (m 1H) 6.97~6.92 (m 1H) 7.10 (d, J=8.0, 1H)

Preparation Example 146: (6-fluoro-2,2-dimethyl-4H-benzo[d][1,3]dioxin-4-yl)methanol

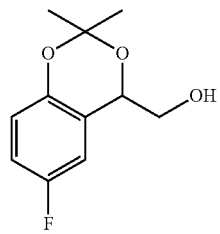

The substantially same method as described in Preparation example 80 was conducted, except that Ethyl 6-fluoro-2,2-dimethyl-4H-benzo[d][1,3]dioxine-4-carboxylate (Preparation example 145) was used instead of Ethyl 8-chloro-2,2-dimethyl-4H-benzo[d][1,3]dioxine-4-carboxylate (Preparation example 79), to obtain the title compound. (4.2 g, 80~95%)

$^1$H NMR (400 MHz, CDCl$_3$) δ 1.50 (s, 3H) 1.62 (s, 3H) 2.18~2.14 (m, 1H) 3.86~3.72 (m, 1H) 4.06~3.94 (m, 1H) 4.95 (s, 1H) 6.81~6.78 (m, 2H) 6.91 (dt, J=8, 4, 1H)

Preparation Example 147: 5-fluoro-2-hydroxybenzaldehyde

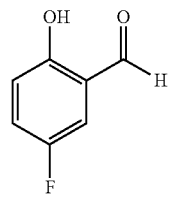

The substantially same method as described in Preparation example 99 was conducted, except that 4-fluorophenol was used instead of 2-chlorophenol, to obtain the title compound. (16.7 g, 60~80%)

$^1$H NMR (400 MHz, CDCl$_3$) δ 7.08~7.05 (dd, J=3.2, 7.2, 1H), 7.32~7.26 (m, 2H), 9.87 (s, 1H), 10.81 (s, 1H)

Preparation Example 148: 2-(benzyloxy)-5-fluorobenzaldehyde

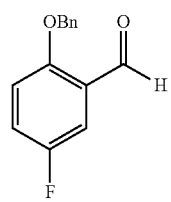 [SMILES: O=Cc1cc(F)ccc1OCc1ccccc1]

The substantially same method as described in Preparation example 100 was conducted, except that 5-fluoro-2-hydroxybenzaldehyde (Preparation example 147) was used instead of 3-chloro-2-hydroxybenzaldehyde (Preparation example 99), to obtain the title compound. (15.4 g, 80~95%)

$^1$H NMR (400 MHz, CDCl$_3$) δ 5.19 (s, 2H), 6.79~6.90 (m, 3H), 7.29~7.49 (m, 5H), 9.54 (s, 1H)

Preparation Example 149:
2-(2-(benzyloxy)-5-fluorophenyl)acetaldehyde

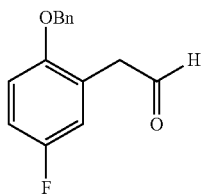 [SMILES: O=CCc1cc(F)ccc1OCc1ccccc1]

The substantially same method as described in Preparation example 61 was conducted, except that 2-(benzyloxy)-5-fluorobenzaldehyde (Preparation example 148) was used instead of 2-(benzyloxy)benzaldehyde (Preparation Example 13), to obtain the title compound. (1.0 g, 50~70%)

$^1$H NMR (400 MHz, CDCl$_3$) δ 3.74 (d, J=2.0, 2H), 5.12 (s, 2H), 6.79~6.83 (m, 2H), 6.87~6.90 (m, 1H), 7.3~7.42 (m, 5H), 9.76 (s, 1H)

Preparation Example 150:
2-allyl-1-(benzyloxy)-4-fluorobenzene

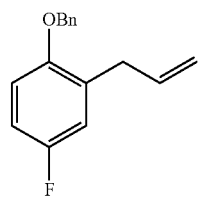 [SMILES: C=CCc1cc(F)ccc1OCc1ccccc1]

The substantially same method as described in Preparation example 14 was conducted, except that 2-(2-(benzyloxy)-5-fluorophenyl)acetaldehyde (Preparation example 149) was used instead of 2-(benzyloxy)benzaldehyde (Preparation Example 13), to obtain the title compound (0.9 g, 80~95%).

1H NMR (400 MHz, CDCl$_3$) δ 3.14 (d, J=6.4, 2H), 5.03 (s, 2H), 5.05 (m, 1H), 5.09 (s, 1H), 5.91~6.01 (m, 1H), 6.79~6.83 (m, 2H), 6.87~6.90 (m, 1H), 7.3~7.42 (m, 5H)

Preparation Example 151:
3-(2-(benzyloxy)-5-fluorophenyl)propane-1,2-diol

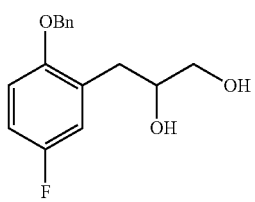 [SMILES: OCC(O)Cc1cc(F)ccc1OCc1ccccc1]

The substantially same method as described in Preparation example 25 was conducted, except that 2-allyl-1-(benzyloxy)-4-fluorobenzene (Preparation example 150) was used instead of 1-(benzyloxy)-2-vinylbenzene (Preparation example 14), to obtain the title compound (0.8 g, 70~90%)

$^1$H NMR (400 MHz, CDCl$_3$) δ 2.07~2.09 (m, 1H), 2.44 (br s, 1H), 2.81 (d, J=6.4, 2H), 3.40~3.44 (m, 1H), 3.54~3.57 (m, 1H), 3.87 (br s, 1H), 5.05 (q, J=11.2, 2H), 6.82~6.87 (m, 2H), 6.9 (m, 1H), 7.30~7.41 (m, 5H)

Preparation Example 152:
3-(2-(benzyloxy)-5-fluorophenyl)-2-hydroxypropyl pivalate

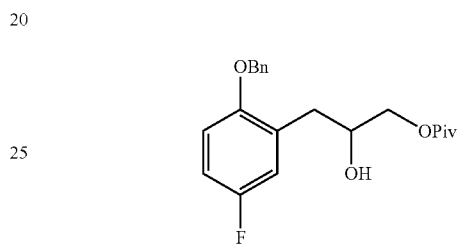

The substantially same method as described in Preparation example 3 was conducted, except that 3-(2-(benzyloxy)-5-fluorophenyl)propane-1,2-diol (Preparation example 151) was used instead of 3-(2-(benzyloxy)phenyl)propane-1,2-diol (Preparation example 2), to obtain the title compound (2.6 g, 75~90%).

$^1$H NMR (400 MHz, CDCl$_3$) δ 1.20 (s, 9H), 2.37 (br s, 1H), 2.82~2.97 (m, 2H), 4.00~4.04 (m, 1H), 4.09~4.14 (m, 2H), 5.05 (s, 2H), 6.82~6.87 (m, 2H), 6.90 (dd, J=2.8, 8.8, 1H), 7.30~7.41 (m, 5H)

Preparation Example 153:
3-(5-fluoro-2-hydroxyphenyl)-2-hydroxypropyl pivalate

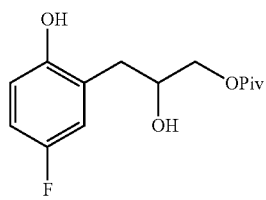

The substantially same method as described in Preparation example 4 was conducted, except 3-(2-(benzyloxy)-5-fluorophenyl)-2-hydroxypropyl pivalate (Preparation example 152) was used instead of 3-(2-(benzyloxy)phenyl)-2-hydroxypropyl pivalate (Preparation example 3), to obtain the title compound (2.2 g, 80~100%).

$^1$H NMR (400 MHz, CDCl$_3$) δ 1.20 (s, 9H), 2.37 (br s, 1H), 2.82~2.97 (m, 2H), 4.00~4.04 (m, 1H), 4.09~4.14 (m, 2H), 6.81~6.87 (m, 3H), 7.62 (s, 1H)

Preparation Example 154: (7-fluoro-2,2-dimethyl-4,5-dihydrobenzo[d][1,3]dioxepin-4-yl)methyl pivalate

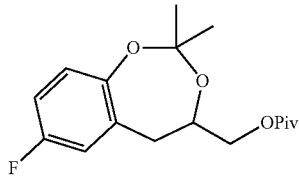

The substantially same method as described in Preparation example 5 was conducted, except 3-(5-fluoro-2-hydroxyphenyl)-2-hydroxypropyl pivalate (Preparation example 153) was used instead of 2-hydroxy-3-(2-hydroxyphenyl)propyl pivalate (Preparation example 4), to obtain the title compound (1.8 g, 75~100%).

$^1$H NMR (400 MHz, CDCl$_3$) δ 1.22 (s, 9H), 1.41 (s, 3H), 1.46 (s, 3H), 2.78~2.85 (m, 1H), 2.96 (dd, J=3.8, 15.8, 1H), 4.14 (d, J=5.2, 2H), 4.43~4.49 (m, 1H), 6.77~6.87 (m, 3H)

Preparation Example 155: (7-fluoro-2,2-dimethyl-4,5-dihydrobenzo[d][1,3]dioxepin-4-yl)methanol

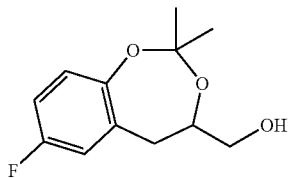 [SMILES: CC1(C)Oc2ccc(F)cc2CC(CO)O1]

The substantially same method as described in Preparation example 6 was conducted, except (7-fluoro-2,2-dimethyl-4,5-dihydrobenzo[d][1,3]dioxepin-4-yl)methyl pivalate (Preparation Example 154) was used instead of (2,2-dimethyl-4,5-dihydrobenzo[d][1,3]dioxepin-4-yl)methyl pivalate (Preparation example 5), to obtain the title compound (1.1 g, 75~100%).

$^1$H NMR (400 MHz, CDCl$_3$) δ 1.46 (s, 3H), 1.47 (s, 3H), 2.00 (br s, 1H), 2.79~2.89 (m, 2H), 3.55~3.66 (m, 2H), 4.23~4.29 (m, 1H), 6.79~6.90 (m, 3H) Preparation example 156 Ethyl 3-(2-(benzyloxy)-5-fluorophenyl)-3-hydroxypropanoate

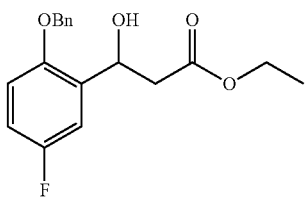 [SMILES: CCOC(=O)CC(O)c1cc(F)ccc1OCc1ccccc1]

The substantially same method as described in Preparation example 48 was conducted, except that 2-(benzyloxy)-5-fluorobenzaldehyde (Preparation example 148) was used instead of 2-(benzyloxy)benzaldehyde (Preparation example 13), to obtain the title compound (3.0 g, 80~100%).

$^1$H NMR (400 MHz, CDCl$_3$) δ 1.24 (t, J=7.0, 3H), 2.65~2.75 (m, 1H), 2.85~2.91 (m, 1H), 3.49 (d, J=5.2, 1H), 4.09~4.22 (m, 2H), 5.12 (s, 2H), 5.41~5.49 (m, 1H), 6.91~6.94 (m, 1H), 6.97~7.02 (m, 2H), 7.21~7.28 (m, 5H)

Preparation Example 157: Ethyl 3-(5-fluoro-2-hydroxyphenyl)-3-hydroxypropanoate

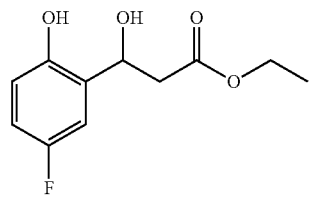 [SMILES: CCOC(=O)CC(O)c1cc(F)ccc1O]

The substantially same method as described in Preparation example 17 was conducted, except that ethyl 3-(2-(benzyloxy)-5-fluorophenyl)-3-hydroxypropanoate (Preparation example 156) was used instead of (R)-1-(2-(benzyloxy)phenyl-2-(tert-butyldimethylsilyloxy)ethanol (Preparation example 16), to obtain the title compound (1.9 g, 80~100%).

$^1$H NMR (400 MHz, CDCl$_3$) δ 1.30 (t, J=7.2, 3H), 2.68~2.77 (m, 1H), 2.92~3.02 (m, 1H), 4.23 (q, J=7.2, 1H), 4.48 (s, 1H), 5.24 (dd, J=2.8, 10.0, 1H), 6.82~6.92 (m, 2H), 6.95~7.02 (m, 1H), 7.96 (s, 1H)

Preparation Example 158: Ethyl 2-(6-fluoro-2,2-dimethyl-4H-benzo[d][1,3]dioxin-4-yl)acetate

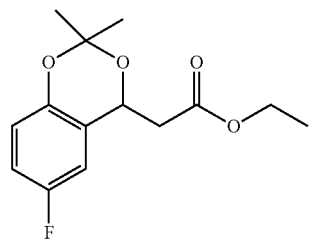 [SMILES: CCOC(=O)CC1OC(C)(C)Oc2ccc(F)cc21]

The substantially same method as described in Preparation example 18 was conducted, except that ethyl 3-(5-fluoro-2-hydroxyphenyl)-3-hydroxypropanoate (Preparation example 157) was used instead of (R)-2-(2-(tert-butyldimethylsilyloxy)-1-hydroxyethyl)phenol (Preparation example 17), to obtain the title compound. (1.7 g, 55~85%).

$^1$H NMR (400 MHz, CDCl$_3$) δ 1.28 (t, J=7.0, 3H), 1.50 (s, 3H), 1.56 (s, 3H), 2.71 (q, J=8.1, 1H), 2.92 (q, J=6.4, 1H), 4.15~4.28 (m, 2H), 5.38 (q, J=4.2, 1H), 6.79~6.84 (m, 2H), 6.87~6.93 (m, 1H)

Preparation Example 159: 2-(6-fluoro-2,2-dimethyl-4H-benzo[d][1,3]dioxin-4-yl)ethanol

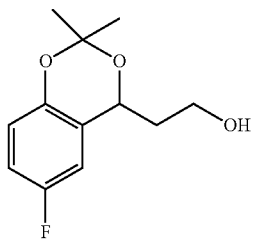 [SMILES: CC1(C)Oc2ccc(F)cc2C(CCO)O1]

The substantially same method as described in Preparation example 51 was conducted, except that ethyl 2-(6-fluoro-2,2-dimethyl-4H-benzo[d][1,3]dioxin-4-yl)acetate (Preparation example 158) was used instead of ethyl 2-(2,2-dimethyl-4H-benzo[d][1,3]dioxin-4-yl)acetate (Preparation example 50), to obtain the title compound. (1.3 g, 75~100%).

$^1$H NMR (400 MHz, CDCl$_3$) δ 1.49 (s, 3H), 1.61 (s, 3H), 1.99~2.09 (m, 1H), 2.27~2.35 (m, 1H), 3.83 (m, 2H), 5.13 (q, J=3.7, 1H), 6.73~6.80 (m, 2H), 6.87~6.92 (m, 1H)

Preparation Example 160: Ethyl 2-hydroxy-2-(2-hydroxy-5-methoxyphenyl)acetate

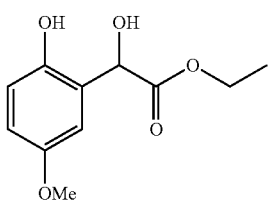 [SMILES: CCOC(=O)C(O)c1cc(OC)ccc1O]

The substantially same method as described in Preparation example 78 was conducted, except that 4-methoxyphenol was used instead of 2-chlorophenol, to obtain the title compound (4.9 g, 45~70%)

$^1$H NMR (400 MHz, CDCl$_3$) δ 1.28 (t, J=4.0, 3H), 3.78 (s, 3H), 4.11~4.49 (m, 2H), 5.24 (s, 1H), 5.52 (s, 1H), 6.80~6.86 (m, 2H)

Preparation Example 161: Ethyl 6-methoxy-2,2-dimethyl-4H-benzo[d][1,3]dioxine-4-carboxylate

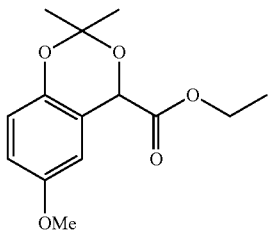 [SMILES: CCOC(=O)C1OC(C)(C)Oc2ccc(OC)cc21]

The substantially same method as described in Preparation example 73 was conducted, except that ethyl 2-hydroxy-2-(2-hydroxy-5-methoxyphenyl)acetate (Preparation example 160) was used instead of (S)-((1R,2S,5R)-2-isopropyl-5-methylcyclohexyl) 2-(3-chloro-2-hydroxyphenyl)-2-hydroxyacetate (Preparation example 72), to obtain the title compound. (5.26 g, 80~100%)

$^1$H NMR (400 MHz, CDCl$_3$) δ 1.36 (t, J=8.0, 3H), 1.53 (s, 3H), 1.64 (s, 3H), 3.77 (s, 3H), 4.34 (q, J=9.0, 2H), 5.43 (s, 1H), 6.70~6.83 (m, 2H), 6.84 (s, 1H)

Preparation Example 162: (6-methoxy-2,2-dimethyl-4H-benzo[d][1,3]dioxin-4-yl)methanol

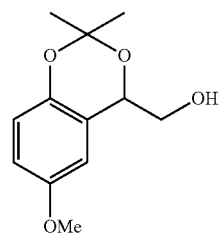 [SMILES: COc1ccc2c(c1)C(CO)OC(C)(C)O2]

The substantially same method as described in Preparation example 51 was conducted, except that Ethyl 6-methoxy-2,2-dimethyl-4H-benzo[d][1,3]dioxine-4-carboxylate (Preparation example 161) was used instead of ethyl 2-(2,2-dimethyl-4H-benzo[d][1,3]dioxin-4-yl)acetate (Preparation example 50), to obtain the title compound. (4.26 g, 70~90%)

$^1$H NMR (400 MHz, CDCl$_3$) δ 1.50 (s, 3H), 1.62 (s, 3H), 2.09~2.12 (m, 1H), 3.78 (s, 3H), 3.84~3.95 (m, 1H), 4.02~4.41 (m, 1H), 4.97 (s, 1H), 6.60 (s, 1H), 6.79 (s, 2H)

Example 1: ((R)-2,2-dimethyl-4H-benzo[d][1,3]dioxin-4-yl)methyl sulfamate

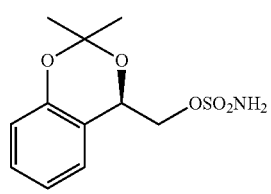

Acetonitrile (5.2 mL, 99.18 mmol) was added in a flask and cooled to 0° C. Chlorosulfonyl isocyanate (2.6 ml, 29.7 mmol), and formic acid (1.2 ml, 31.7 mmol) was added dropwise and stirred at room temperature for 6 hours. (R)-(2,2-dimethyl-4H-benzo[d][1,3]dioxin-4-yl)methanol (Preparation example 19, 2.9 g, 9.9 mmol) in N,N-dimethyl acetamide (9.2 ml, 99.2 mmol) was slowly added at 0° C. and stirred at room temperature for 1 hours. The reaction mixture was quenched with H$_2$O, extracted with EtOAc, and washed with H$_2$O. The organic layer was dried over anhydrous magnesium sulfate (MgSO$_4$), filtered and concentrated. The crude compound was purified by a silica gel column to produce the title compound (3.2 g, 50~80%).

$^1$H NMR (400 MHz, CDCl$_3$) δ 1.50 (s, 3H), 1.62 (s, 3H), 4.44~4.49 (m, 1H), 4.62~4.66 (m, 1H), 4.82 (s, 1H), 5.19~5.21 (m, 1H), 6.84~6.86 (m, 1H), 6.93~6.97 (m, 1H), 7.07~7.09 (d, J=8.0, 1H), 7.20~7.24 (m, 1H).

TABLE 1

Example of phenyl sulfamate derivatives compounds

| No | X | Position | n | l | m | R¹ | R² | R³ | R⁴ | Chiral | Salt |
|---|---|---|---|---|---|---|---|---|---|---|---|
| 1 | H | — | — | 0 | 1 | Me | Me | H | H | R | — |
| 2 | H | — | — | 0 | 1 | Me | Me | H | H | S | — |
| 3 | H | — | — | 0 | 1 | Me | Me | H | H | Rac. | — |
| 4 | H | — | — | 0 | 1 | Et | Et | H | H | R | — |
| 5 | H | — | — | 0 | 1 | Et | Et | H | H | S | — |
| 6 | H | — | — | 0 | 1 | Et | Et | H | H | Rac. | — |
| 7 | H | — | — | 0 | 1 | Cyclopentyl | H | H | H | R | — |
| 8 | H | — | — | 0 | 1 | Cyclopentyl | H | H | H | S | — |
| 9 | H | — | — | 0 | 1 | Cyclopentyl | H | H | H | Rac. | — |
| 10 | H | — | — | 0 | 1 | Cyclohexyl | H | H | H | R | — |
| 11 | H | — | — | 0 | 1 | Cyclohexyl | H | H | H | S | — |
| 12 | H | — | — | 0 | 1 | Cyclohexyl | H | H | H | Rac. | — |
| 13 | H | — | — | 0 | 2 | Me | Me | H | H | Rac. | — |
| 14 | H | — | — | 0 | 2 | Et | Et | H | H | Rac. | — |
| 15 | H | — | — | 0 | 2 | Cyclopentyl | H | H | H | Rac. | — |
| 16 | H | — | — | 0 | 2 | Cyclohexyl | H | H | H | Rac. | — |
| 17 | H | — | — | 1 | 1 | Me | Me | H | H | Rac. | — |
| 18 | H | — | — | 1 | 1 | Et | Et | H | H | Rac. | — |
| 19 | H | — | — | 1 | 1 | Cyclopentyl | H | H | H | Rac. | — |
| 20 | H | — | — | 1 | 1 | Cyclohexyl | H | H | H | Rac. | — |
| 21 | H | — | — | 1 | 2 | Me | Me | H | H | Rac. | — |
| 22 | H | — | — | 1 | 2 | Et | Et | H | H | Rac. | — |
| 23 | H | — | — | 1 | 2 | Cyclopentyl | H | H | H | Rac. | — |
| 24 | H | — | — | 1 | 2 | Cyclohexyl | H | H | H | Rac. | — |
| 25 | Cl | 8 | 1 | 0 | 1 | Me | Me | H | H | R | — |
| 26 | Cl | 8 | 1 | 0 | 1 | Me | Me | H | H | S | — |
| 27 | Cl | 8 | 1 | 0 | 1 | Me | Me | H | H | Rac. | — |
| 28 | Cl | 8 | 1 | 0 | 1 | Et | Et | H | H | R | — |
| 29 | Cl | 8 | 1 | 0 | 1 | Et | Et | H | H | S | — |
| 30 | Cl | 8 | 1 | 0 | 1 | Et | Et | H | H | Rac. | — |
| 31 | Cl | 8 | 1 | 0 | 1 | Cyclopentyl | H | H | H | R | — |
| 32 | Cl | 8 | 1 | 0 | 1 | Cyclopentyl | H | H | H | S | — |
| 33 | Cl | 8 | 1 | 0 | 1 | Cyclopentyl | H | H | H | Rac. | — |
| 34 | Cl | 8 | 1 | 0 | 1 | Cyclohexyl | H | H | H | R | — |
| 35 | Cl | 8 | 1 | 0 | 1 | Cyclohexyl | H | H | H | S | — |
| 36 | Cl | 8 | 1 | 0 | 1 | Cyclohexyl | H | H | H | Rac. | — |
| 37 | Cl | 8 | 1 | 0 | 2 | Me | Me | H | H | Rac. | — |
| 38 | Cl | 8 | 1 | 0 | 2 | Et | Et | H | H | Rac. | — |
| 39 | Cl | 8 | 1 | 0 | 2 | Cyclopentyl | H | H | H | Rac. | — |
| 40 | Cl | 8 | 1 | 0 | 2 | Cyclohexyl | H | H | H | Rac. | — |
| 41 | Cl | 9 | 1 | 1 | 2 | Me | Me | H | H | Rac. | — |
| 42 | Cl | 9 | 1 | 1 | 2 | Et | Et | H | H | Rac. | — |
| 43 | Cl | 9 | 1 | 1 | 2 | Cyclopentyl | H | H | H | Rac. | — |
| 44 | Cl | 9 | 1 | 1 | 2 | Cyclohexyl | H | H | H | Rac. | — |
| 45 | Cl | 7 | 1 | 0 | 1 | Me | Me | H | H | Rac. | — |
| 46 | Cl | 6 | 1 | 0 | 1 | Me | Me | H | H | R | — |
| 47 | Cl | 6 | 1 | 0 | 1 | Me | Me | H | H | S | — |
| 48 | Cl | 6 | 1 | 0 | 1 | Me | Me | H | H | Rac. | — |
| 49 | Cl | 6 | 1 | 0 | 1 | Et | Et | H | H | R | — |
| 50 | Cl | 6 | 1 | 0 | 1 | Et | Et | H | H | S | — |
| 51 | Cl | 6 | 1 | 0 | 1 | Et | Et | H | H | Rac. | — |
| 52 | Cl | 6 | 1 | 0 | 1 | Cyclopentyl | H | H | H | Rac. | — |
| 53 | Cl | 6 | 1 | 0 | 1 | Cyclohexyl | H | H | H | Rac. | — |
| 54 | F | 6 | 1 | 0 | 1 | Me | Me | H | H | Rac. | — |
| 55 | F | 6 | 1 | 0 | 2 | Me | Me | H | H | Rac. | — |
| 56 | F | 7 | 1 | 1 | 1 | Me | Me | H | H | Rac. | — |
| 57 | OMe | 6 | 1 | 0 | 1 | Me | Me | H | H | Rac. | — |
| 58 | H | — | — | 0 | 1 | Me | Me | H | H | R | Na |
| 59 | H | — | — | 0 | 1 | Me | Me | H | H | S | Na |
| 60 | H | — | — | 0 | 1 | Me | Me | H | H | Rac. | Na |
| 61 | Cl | 6 | 1 | 0 | 1 | Me | Me | H | H | R | Na |
| 62 | Cl | 6 | 1 | 0 | 1 | Me | Me | H | H | S | Na |
| 63 | Cl | 6 | 1 | 0 | 1 | Me | Me | H | H | Rac. | Na |
| 64 | H | — | — | 0 | 1 | Cyclopentyl | H | H | H | R | Na |
| 65 | H | — | — | 0 | 1 | Cyclopentyl | H | H | H | S | Na |
| 66 | H | — | — | 0 | 1 | Cyclopentyl | H | H | H | Rac. | Na |
| 67 | Cl | 6 | 1 | 0 | 1 | Cyclopentyl | H | H | H | Rac. | Na |
| 68 | H | — | — | 0 | 2 | Me | Me | H | H | Rac. | Na |
| 69 | H | — | — | 0 | 2 | Cyclopentyl | H | H | H | Rac. | Na |
| 70 | H | — | — | 0 | 1 | Me | Me | H | H | R | K |
| 71 | H | — | — | 0 | 1 | Me | Me | H | H | S | K |
| 72 | H | — | — | 0 | 1 | Me | Me | H | H | Rac. | K |
| 73 | H | — | — | 0 | 1 | Me | Me | H | H | S | Li |

According to the method described in Example 1, the following compounds of Examples 2 to 57 were prepared:

TABLE 2

Structure of Example

| Example No. | Structure | Name | Starting material | ¹H NMR (400 MHz, CDCl₃) |
|---|---|---|---|---|
| 2 | 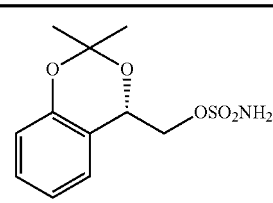 | ((S)-2,2-dimethyl-4H-benzo[d][1,3]diox-in-4-yl)methyl sulfamate | Preparation example 24 | (DMSO) δ = 1.41 (s, 3H), 1.51 (s, 3H), 4.27~4.20 (m, 1H), 4.46 (dd, J = 2.6, J = 11.0, 1H), 5.24~522 (m, 1H), 6.77 (d, J = 8.0, 1H), 6.89 (d, J = 7.6, 1H), 7.19~7.15 (m, 1H), 7.27 (d, J = 7.6, 1H), 7.70 (s, 2H) |
| 3 | 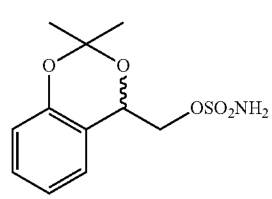 | (2,2-dimethyl-4H-benzo[d][1,3]diox-in-4-yl))methyl sulfamate | Preparation example 29 | δ 1.50 (s, 3H), 1.62 (s, 3H), 4.44~4.49 (m, 1H), 4.62~4.66 (m, 1H), 4.82 (s, 1H), 5.19~5.21 (m, 1H), 6.84~6.86 (m, 1H), 6.93~6.97 (m, 1H), 7.07~7.09 (d, J = 8.0, 1H), 7.20~7.24 (m, 1H). |

TABLE 2-continued

Structure of Example

| Example No. | Structure | Name | Starting material | $^1$H NMR (400 MHz, CDCl$_3$) |
|---|---|---|---|---|
| 4 | 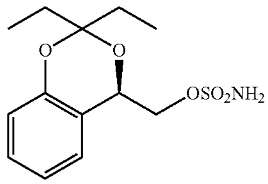 | ((R)-2,2-diethyl-4H-benzo[d][1,3]dioxin-4-yl)methyl sulfamate | Preparation example 31 | (DMSO) δ 0.83 (t, J = 7.4, 3H), 0.96 (t, J = 7.4, 3H), 1.68~1.82 (m, 4H), 4.23 (dd, J = 6.0, 10.8, 1H), 4.45 (dd, J = 2.4, 10.8, 1H), 5.10~5.18 (m, 1H), 6.81~6.84 (m, 1H), 6.92~6.96 (m, 1H), 7.20~7.24 (m, 2H), 7.63 (br s, 2H) |
| 5 | 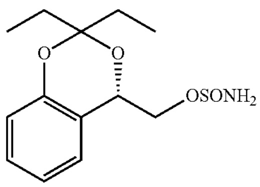 | ((S)-2,2-diethyl-4H-benzo[d][1,3]dioxin-4-yl)methyl sulfamate | Preparation example 33 | (DMSO) δ 0.83 (t, J = 7.4, 3H), 0.96 (t, J = 7.4, 3H), 1.68~1.82 (m, 4H), 4.23 (dd, J = 6.0, 10.8, 1H), 4.45 (dd, J = 2.4, 10.8, 1H), 5.10~5.18 (m, 1H), 6.81~6.84 (m, 1H), 6.92~6.96 (m, 1H), 7.20~7.24 (m, 2H), 7.63 (br s, 2H) |
| 6 | 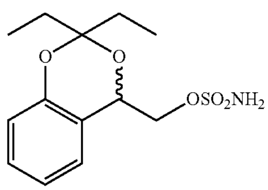 | (2,2-diethyl-4H-benzo[d][1,3]dioxin-4-yl))methyl sulfamate | Preparation example 35 | (DMSO) δ 0.83 (t, J = 7.4, 3H), 0.96 (t, J = 7.4, 3H), 1.68~1.82 (m, 4H), 4.23 (dd, J = 6.0, 10.8, 1H), 4.45 (dd, J = 2.4, 10.8, 1H), 5.10~5.18 (m, 1H), 6.81~6.84 (m, 1H), 6.92~6.96 (m, 1H), 7.20~7.24 (m, 2H), 7.63 (br s, 2H) |
| 7 | 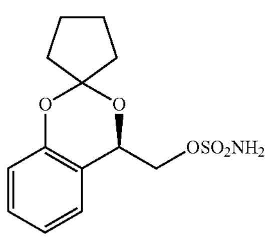 | ((R)-4H-spiro[benzo[d][1,3]dioxine-2,1'-cyclopentan]-4-yl)methyl sulfamate | Preparation example 37 | (DMSO) δ 1.67~1.76 (m, 5H), 1.87~2.05 (m, 3H), 4.26 (dd, J = 4.8, 6.0, 1H), 4.44 (dd, J = 2.8, 8.4, 1H), 5.26 (dd, J = 2.8, 3.2, 1H), 6.84 (d, J = 7.2, 1H), 6.97 (dt, J = 1.0, 7.4, 1H), 7.23~7.34 (m, 2H), 7.58 (br s, 2H) |
| 8 | 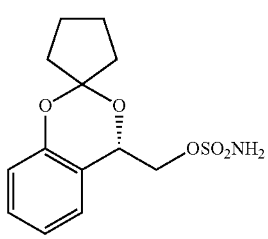 | ((S)-4H-spiro[benzo[d][1,d]dioxine-2,1'-cyclopentan]-4-yl)methyl sulfamate | Preparation example | (DMSO) δ 1.67~1.76 (m, 5H), 1.87-2.05 (m, 3H), 4.26 (dd, J = 4.8, 6.0, 1H), 4.44 (dd, J = 2.8, 8.4, 1H), 5.26 (dd, J = 2.8, 3.2, 1H), 6.84 (d, J = 7.2, 1H), 6.97 (dt, J = 1.0, 7.4, 1H), 7.23~7.34 (m, 2H), 7.58 (br s, 2H) |

TABLE 2-continued

| Example No. | Structure | Name | Starting material | $^1$H NMR (400 MHz, CDCl$_3$) |
|---|---|---|---|---|
| 9 | 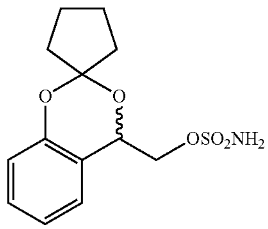 | (4H-spiro[benzo[d][1,3]dioxine-2,1'-cyclopentan]-4-yl)methyl sulfamate | Preparation example 41 | (DMSO) δ 1.67~1.76 (m, 5H), 1.87~2.05 (m, 3H), 4.26 (dd, J = 4.8, 6.0, 1H), 4.44 (dd, J = 2.8, 8.4, 1H), 5.26 (dd, J = 2.8, 3.2, 1H), 6.84 (d, J = 7.2, 1H), 6.97 (dt, J = 1.0, 7.4, 1H), 7.23~7.34 (m, 2H), 7.58 (br s, 2H) |
| 10 | 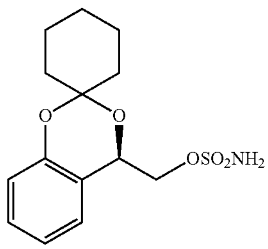 | ((R)-4H-spiro[benzo[d][1,3]dioxine-2,1'-cylcohexan]-4-yl)methyl sulfamate | Preparation example 43 | (DMSO) δ 1.34 (s, 4H), 1.65~1.80 (m, 6H), 4.25 (dd, J = 4.8, 6.0, 1H), 4.45 (dd, J = 2.8, 8.0, 1H), 5.20 (dd, J = 2.4, 3.6, 1H), 6.84 (d, J = 7.6, 1H), 6.95 (t, J = 6.4, 1H), 7.22 (t, J = 7.6, 2H), 7.57 (br s, 2H) |
| 11 | 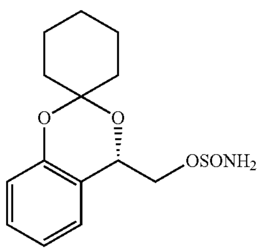 | ((S)-4H-spiro[benzo[d][1,3]dioxine-2,1'-cylcohexan]-4-yl)methyl sulfamate | Preparation example 45 | (DMSO) δ 1.34 (s, 4H), 1.65~1.80 (m, 6H), 4.25 (dd, J = 4.8, 6.0, 1H), 4.45 (dd, J = 2.8, 8.0, 1H), 5.20 (dd, J = 2.4, 3.6, 1H), 6.84 (d, J = 7.6, 1H), 695 (t, J = 6.4, 1H), 7.22 (t, J = 7.6, 2H), 7.57 (br s, 2H) |
| 12 | 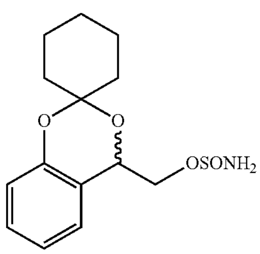 | (4H-spiro[benzo[d][1,3]dioxine-2,1'-cyclohexan]-4-yl)methyl sulfamate | Preparation example 47 | (DMSO) δ 1.34 (s, 4H), 1.65~1.80 (m, 6H), 4.25 (dd, J = 4.8, 6.0, 1H), 4.45 (dd, J = 2.8, 8.0, 1H), 5.20 (dd, J = 2.4, 3.6, 1H), 6.84 (d, J = 7.6, 1H), 6.95 (t, J = 6.4, 1H), 7.22 (t, J = 7.6, 2H), 7.57 (br s, 2H) |
| 13 | 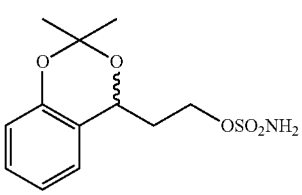 | 2-(2,2-dimethyl-4H-benzo[d][1.3]diox-in-4-yl)ethyl sulfamate | Preparation example 51 | δ 1.48 (s, 3H), 1.58 (s, 3H), 2.11~2.22 (m, 1H), 2.43~2.54 (m, 1H), 4.26-4.35 (m, 1H), 4.41~4.49 (m, 1H), 4.60 (br s, 2H), 5.08 (q, J = 3.5, 1H), 6.81 (d, J = 8.4, 1H), 6.93 (t, J = 7.4, 1H), 7.04 (d, J = 7.6, 1H), 7.18 (t, J = 7.8, 1H) |

TABLE 2-continued

Structure of Example

| Example No. | Structure | Name | Starting material | $^1$H NMR (400 MHz, CDCl$_3$) |
|---|---|---|---|---|
| 14 | 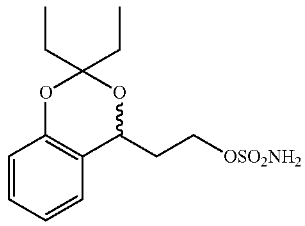 | 2-(2,2-diethyl-4H-benzo[d][1.3]diox-in-4-yl)ethyl sulfamate | Preparation example 56 | δ 0.90 (t, J = 7.4, 3H), 1.01 (t, J = 7.4, 3H), 1.75~1.89 (m, 4H), 2.10~2.21 (m, 1H), 2.45~2.55 (m, 1H), 4.28~4.36 (m, 1H), 4.43~4.50 (m, 1H), 4.62 (br s, 2H), 5.02~5.07 (m, 1H), 6.82 (d, J = 8.0, 1H), 6.90 (t, J = 7.6, 1H), 7.02 (d, J = 7.6, 1H), 7.13~7.20 (m, 1H) |
| 15 | 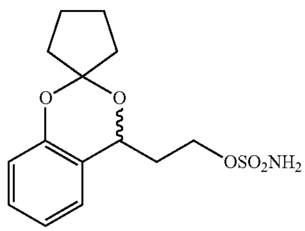 | 2-(4H-spiro[benzo[d][1.3]dioxine-2,1'-cyclopentan]-4-yl)ethyl sulfamate | Preparation example 58 | δ 1.64~1.90 (m, 5H), 1.93-2.22 (m, 3H), 2.23-2.32 (m, 1H), 2.45~2.56 (m, 1H), 4.27~4.37 (m, 1H), 4.38~4.50 (m, 1H), 4.62 (br s, 2H), 5.11 (d, J = 7.6, 1H), 6.83 (d, J = 8.4, 1H), 6.93 (t, J = 8.0, 1H), 7.03 (d, J = 8.0, 1H), 7.17 (t, J = 7.8, 1H) |
| 16 | 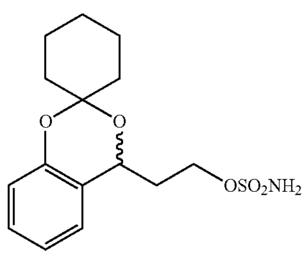 | 2-(4H-spiro[benzo[d][1.3]dioxine-2,1'-cyclohexan]-4-yl)ethyl sulfamate | Preparation example 60 | δ 1.40~1.56 (m, 4H), 1.63~1.92 (m, 6H), 2.09~2.19 (m, 1H), 2.46~2.55 (m, 1H), 4.31~4.37 (m, 1H), 4.45~4.53 (m, 1H), 4.60 (br s, 2H) 5.04~5.09 (m, 1H), 6.83 (d, J = 8.0, 1H), 6.89~6.94 (m, 1H), 7.02 (d, J = 7.6, 1H), 7.14~7.20 (m, 1H) |
| 17 | 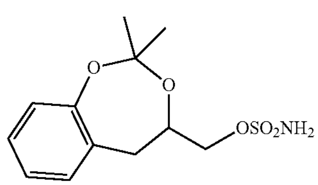 | (2,2-dimethyl-4,5-dihydrobenzo[d][1,3]dioxepin-4-yl)methyl sulfamate | Preparation example 6 | δ 1.47 (s, 3H), 1.53 (s, 3H), 2.62~2.84 (m, 1H), 3.12~3.19 (m, 1H), 3.56~3.79 (m, 1H), 4.12~4.36 (m, 1H), 4.42~4.37 (m, 1H), 5.55 (br s, 2H), 7.23~7.30 (m, 2H), 7.32~7.35 (m, 1H), 7.48~7.59 (m, 1H) |
| 18 | 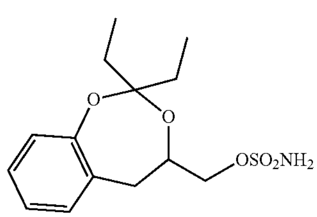 | (2,2-diethyl-4,5-dihydrobenzo[d][1,3]dioxepin-4-yl)methyl sulfamate | Preparation example 8 | δ 0.69-1.00 (m, 6H), 1.55~1.75 (m, 4H), 2.59~2.81 (m, 1H), 3.22~3.29 (m, 1H), 3.66~3.76 (m, 1H), 4.12~4.36 (m, 1H), 4.37~4.43 (m, 1H), 5.55 (br s, 2H), 7.23~7.30 (m, 2H), 7.31~7.36 (m, 1H), 7.56~7.49 (m, 1H). |

TABLE 2-continued

Structure of Example

| Example No. | Structure | Name | Starting material | $^1$H NMR (400 MHz, CDCl$_3$) |
|---|---|---|---|---|
| 19 | 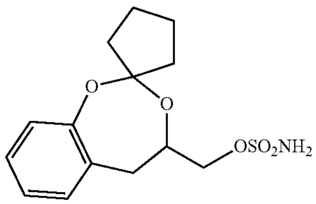 | (4,5-dihydrospiro[benzo[d][1,3]dioxepine-2,1'-cyclopentan]-4-yl)methyl sulfamate | Preparation example 10 | δ 1.65~1.96 (m, 8H), 2.86 (d, J = 8.0, 1H), 2.94~3.18 (m, 1H), 3.73 (t, J = 8.0, 1H), 4.06~4.16 (m, 1H), 4.20~4.37 (m, 1H), 5.55 (br s, 2H), 7.27~7.36 (m, 3H), 7.47~7.55 (m, 1H) |
| 20 | 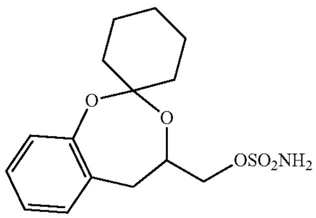 | (4,5-dihydrospiro[benzo[d][1,3]dioxepine-2,1'-cyclohexan]-4-yl)methyl sulfamate | Preparation example 12 | 1.47~1.90 (m, 10H), 2.98~3.21 (m, 1H), 3.64~3.80 (m, 1H), 4.11~4.17 (m, 2H), 4.30~4.49 (m, 1H), 5.41 (br s, 2H), 7.26~7.40 (m, 3H), 7.52~7.67 (m, 1H) |
| 21 | 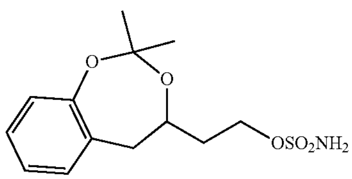 | 2-(2,2-dimethyl-4,5-dihydrobenzo[d][1,3]dioxepin-4-yl)ehtyl sulfamate | Preparation example 65 | δ 1.47 (s, 3H), 1.53 (s, 3H), 1.79~1.92 (m, 2H), 2.32~2.34 (m, 1H), 2.89 (dd, J = 3.0, 15.4, 1H), 3.01 (dd, J = 9.6, 15.2, 1H), 3.81~3.85 (m, 2H), 4.34 (br s, 2H), 6.92 (d, J = 8.0, 1H), 7.03~7.10 (m, 2H), 7.14~7.19 (m, 1H) |
| 22 | 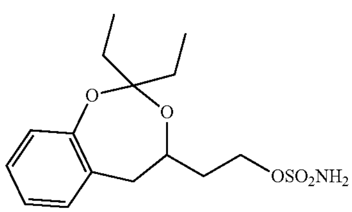 | 2-(2,2-diethyl-4,5-dihydrobenzo[d][1,3]dioxepin-4-yl)ethyl sulfamate | Preparation example 67 | δ 0.90~0.95 (m, 6H), 1.62~1.70 (m, 4H), 1.81~1.90 (m, 2H), 2.33~2.34 (m, 1H), 2.94 (dd, J = 3.0, 15.4, 1H), 3.06 (dd, J = 9.6, 15.2, 1H), 3.78~3.83 (m, 2H), 4.37 (br s, 2H), 6.91 (d, J = 8.0, 1H), 7.02~7.09 (m, 2H), 7.14~7.18 (m, 1H) |
| 23 | 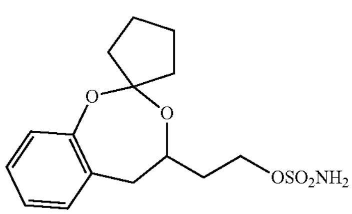 | 2-(4,5-dihydrospiro[benzo[d][1,3]dioxepine-2,1'-cyclopentan]-4-yl)ethyl sulfamate | Preparation example 69 | δ 1.68~1.74 (m, 3H), 1.80~1.87 (m, 5H), 1.78~1.93 (m, 2H), 2.32~2.35 (m, 1H), 2.89 (dd, J = 3.0, 15.4, 1H), 3.01 (dd, J = 9.6, 15.2, 1H), 3.81~3.85 (m, 2H), 4.4 (br s, 2H), 6.91 (d, J = 8.0, 1H), 7.02~7.09 (m, 2H), 7.14~7.18 (m, 1H). |

TABLE 2-continued

Structure of Example

| Example No. | Structure | Name | Starting material | ¹H NMR (400 MHz, CDCl₃) |
|---|---|---|---|---|
| 24 | 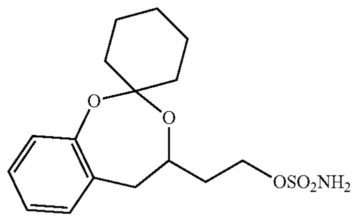 | 2-(4,5-dihydrospiro[benzo[d][1,3]dioxepine-2,1'-cyclohexan]-4-yl)ethyl sulfamate | Preparation example 71 | δ 1.55~1.66 (m, 10H), 1.82~1.90 (m, 2H), 2.32~2.34 (m, 1H), 2.92 (dd, J = 3.0, 15.4, 1H), 3.08 (dd, J = 9.6, 15.2, 1H), 3.78~3.82 (m, 2H), 4.42 (br s, 2H), 6.91 (d, J = 8.0, 1H), 7.02~7.09 (m, 2H), 7.14~7.18 (m, 1H) |
| 25 | 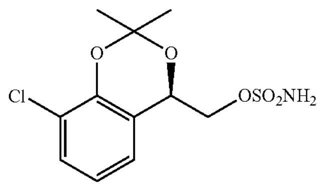 | ((R)-8-chloro-2,2-dimethyl-4H-benzo[d][1,3]diox-in-4-yl)methyl sulfamate | Preparation example 77 | δ 1.46 (s, 3H), 1.53 (s, 3H), 2.21~2.30 (m, 1H), 3.71~3.80 (m, 1H), 4.08~4.12 (m, 1H), 4.59 (br s, 2H), 6.82 (t, J = 7.8, 1H), 6.90 (d, J = 7.6, 1H), 7.15 (d, J = 7.6, 1H) |
| 26 | 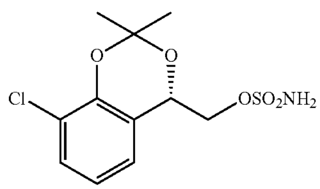 | ((S)-8-chloro-2,2-dimethyl-4H-benzo[d][1,3]diox-in-4-yl)methyl sulfamate | Preparation example 74 | δ 1.46 (s, 3H), 1.53 (s, 3H), 2.21~2.30 (m, 1H), 3.71~3.80 (m, 1H), 4.08~4.12 (m, 1H), 4.59 (br s, 2H), 6.82 (t, J = 7.8, 1H), 6.90 (d, J = 7.6, 1H), 7.15 (d, J = 7.6, 1H) |
| 27 | 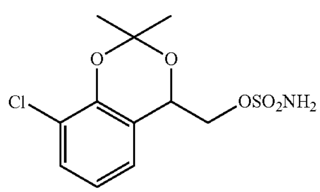 | (8-chloro-2,2-dimethyl-4H-benzo[d][1,3]diox-in-4-yl)methyl sulfamate | Preparation example 80 | δ 1.46 (s, 3H), 1.53 (s, 3H), 2.21~2.30 (m, 1H), 3.71~3.80 (m, 1H), 4.08~4.12 (m, 1H), 4.59 (br s, 2H), 6.82 (t, J = 7.8, 1H), 6.90 (d, J = 7.6, 1H), 7.15 (d, J = 7.6, 1H |
| 28 | 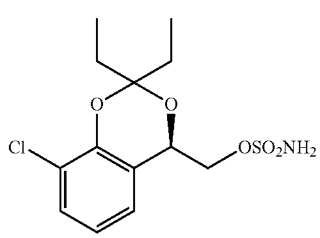 | ((R)-8-chloro-2,2-diethyl-4H-benzo[d][1,3]diox-in-4-yl)methyl sulfamate | Preparation example 84 | δ 0.91 (s, 6H), 1.56~1.60 (m, 4H), 2.28~2.36 (m, 1H), 3.83~3.90 (m, 1H), 4.12~4.19 (m, 1H), 4.67 (br s, 2H), 6.90 (t, J = 7.8, 1H), 7.02 (d, J = 7.6, 1H), 7.16 (d, J = 7.6, 1H) |
| 29 | 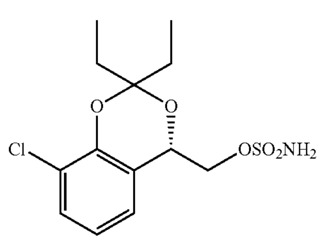 | ((S)-8-chloro-2,2-diethyl-4H-benzo[d][1,3]diox-in-4-yl)methyl sulfamate | Preparation example 82 | δ 0.91 (s, 6H), 1.56~1.60 (m, 4H), 2.28~2.36 (m, 1H), 3.83~3.90 (m, 1H), 4.12~4.19 (m, 1H), 4.67 (br s, 2H), 6.90 (t, J = 7.8, 1H), 7.02 (d, J = 7.6, 1H), 7.16 (d, J = 7.6, 1H) |

TABLE 2-continued

Structure of Example

| Example No. | Structure | Name | Starting material | $^1$H NMR (400 MHz, CDCl$_3$) |
|---|---|---|---|---|
| 30 | 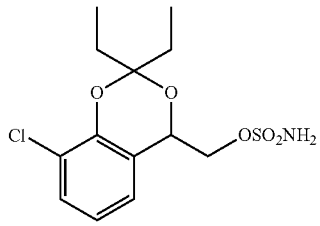 | (8-chloro-2,2-diethyl-4H-benzo[d][1,3]diox-in-4-yl)methyl sulfamate | Preparation example 86 | δ 0.91 (s, 6H), 1.56~1.60 (m, 4H), 2.28~2.36 (m, 1H), 3.83~3.90 (m, 1H), 4.12~4.19 (m, 1H), 4.67 (br s, 2H), 6.90 (t, J = 7.8, 1H), 7.02 (d, J = 7.6, 1H), 7.16 (d, J = 7.6, 1H) |
| 31 | 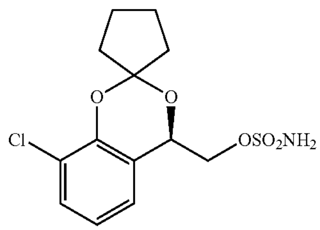 | ((R)-8-chloro-4H-spiro[benzo[d][1,3]dioxine-2,1'-cyclopentan]-4-yl)methyl sulfamate | Preparation example 90 | δ 1.72~1.98 (m, 4H), 2.02~2.17 (m, 4H), 2.21~2.30 (m, 1H), 3.78~3.88 (m, 1H), 4.01~4.09 (m, 1H), 4.79 (br s, 2H), 6.87 (t, J = 7.8, 1H), 6.96 (d, J = 7.6, 1H), 7.26 (d, J = 7.6, 1H) |
| 32 | 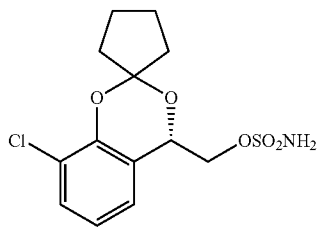 | ((S)-8-chloro-4H-spiro[benzo[d][1,3]dioxine-2,1'-cyclopentan]-4-yl)methyl sulfamate | Preparation example 88 | δ 1.72~1.98 (m, 4H), 2.02~2.17 (m, 4H), 2.21~2.30 (m, 1H), 3.78~3.88 (m, 1H), 4.01~4.09 (m, 1H), 4.79 (br s, 2H), 6.87 (t, J = 7.8, 1H), 6.96 (d, J = 7.6, 1H), 7.26 (d, J = 7.6, 1H) |
| 33 | 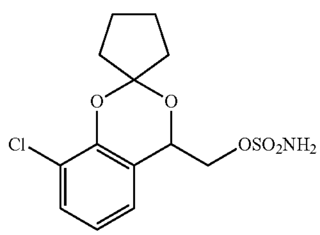 | (8-chloro-4H-spiro[benzo[d][1,3]dioxine2,1'-cylcopentan]-4-yl)methyl sulfamate | Preparation example 92 | δ 1.72~1.98 (m, 4H), 2.02~2.17 (m, 4H), 2.21~2.30 (m, 1H), 3.78~3.88 (m, 1H), 4.01~4.09 (m, 1H), 4.79 (br s, 2H), 6.87 (t, J = 7.8, 1H), 6.96 (d, J = 7.6, 1H), 7.26 (d, J = 7.6, 1H) |
| 34 | 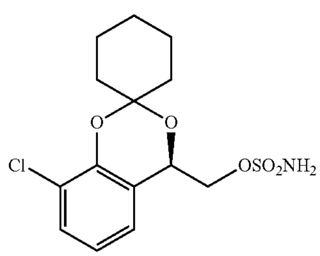 | ((R)-8-chloro-4H-spiro[benzo[d][1,3]dioxine-2,1'-cyclohexan]-4-yl)methyl sulfamate | Preparation example 96 | δ 1.52~1.58 (m, 3H), 1.74~.92 (m, 6H), 1.98~2.06 (m, 1H), 2.12~2.15 (m, 1H), 3.81~3.86 (m, 1H), 4.03~4.09 (m, 1H), 4.72 (br s, 2H), 6.87 (t, J = 7.6, 1H), 6.95~6.98 (m, 1H), 7.27~7.29 (m, 1H) |
| 35 | 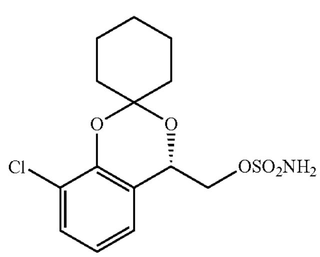 | ((S)-8-chloro-4H-spiro[benzo[d][1,3]dioxine-2,1'-cylcohexan]-4-yl)methyl sulfamate | Preparation example 94 | δ 1.52~1.58 (m, 3H), 1.74~1.92 (m, 6H), 1.98~2.06 (m, 1H), 2.12~2.15 (m, 1H), 3.81~3.86 (m, 1H), 4.03~4.09 (m, 1H), 4.72 (br s, 2H), 6.87 (t, J = 7.6, 1H), 6.95~6.98 (m, 1H), 7.27~7.29 (m, 1H) |

TABLE 2-continued

Structure of Example

| Example No. | Structure | Name | Starting material | $^1$H NMR (400 MHz, CDCl$_3$) |
|---|---|---|---|---|
| 36 | 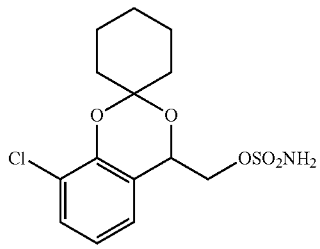 | (8-chloro-4H-spiro[benzo[d][1,3]dioxine-2,1'-cylcohexan]-4-yl)methyl sulfamate | Preparation example 98 | δ 1.52~1.58 (m, 3H), 1.74~1.92 (m, 6H), 1.98~2.06 (m, 1H), 2.12~2.15 (m, 1H), 3.81~3.86 (m, 1H), 4.03~4.09 (m, 1H), 4.72 (br s, 2H), 6.87 (t, J = 7.6, 1H), 6.95~6.98 (m, 1H), 7.27-7.29 (m, 1H) |
| 37 | 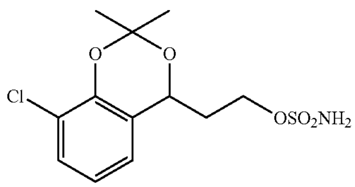 | 2-(8-chloro-2,2-dimethyl-4H-benzo[d][1,3]diox-in-4-yl)ethyl sulfamate | Preparation example 104 | δ 1.44 (s, 3H), 1.52 (s, 3H), 2.11~2.22 (m, 1H), 2.43~2.54 (m, 1H), 4.26~4.35 (m, 1H), 4.41~4.49 (m, 1H), 4.60 (br s, 2H), 5.08 (q, J = 3.5, 1H), 6.87 (t, J = 7.8, 1H), 6.96 (d, J = 7.6, 1H), 7.26 (d, J = 7.6, 1H) |
| 38 | 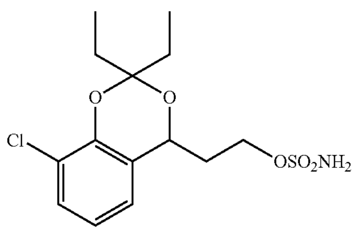 | 2-(8-chloro-2,2-diethyl-4H-benzo[d][1,3]diox-in-4-yl)ethyl sulfamate | Preparation example 106 | δ 0.92 (t, J = 7.4, 3H), 1.06 (t, J = 7.4, 3H), 1.75~1.89 (m, 4H), 2.10~2.21 (m, 1H), 2.45~2.55 (m, 1H), 4.28~4.36 (m, 1H), 4.43~4.50 (m, 1H), 4.62 (br s, 2H), 5.02~5.07 (m, 1H), 6.89 (t, J = 7.8, 1H), 6.98 (d, J = 7.6, 1H), 7.29 (d, J = 7.6, 1H) |
| 39 | 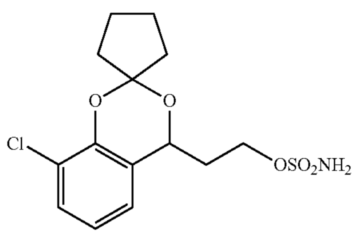 | 2-(8-chloro-4H-spiro[benzo[d][1,3]dioxine-2,1'-cyclopentan]-4-yl)ethyl sulfamate | Preparation example 108 | δ 1.61~1.87 (m, 5H), 1.91~2.25 (m, 3H), 2.23~2.32 (m, 1H), 2.45~2.56 (m, 1H), 4.27~4.37 (m, 1H), 4.38~4.50 (m, 1H), 4.62 (br s, 2H), 5.11 (d, J = 7.6, 1H), 6.83 (t, J = 7.8, 1H), 6.94 (d, J = 7.6, 1H), 7.25 (d, J = 7.6, 1H) |
| 40 | 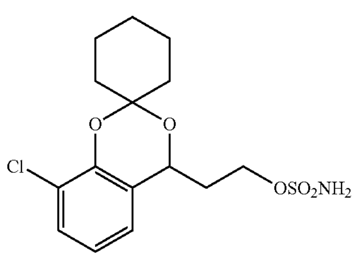 | 2-(8-chloro-4H-spiro[benzo[d][1,3]dioxine-2,1'-cyclohexan]-4-yl)ethyl sulfamate | Preparation example 110 | δ 1.41~1.57 (m, 4H), 1.64~1.95 (m, 6H), 2.09~2.19 (m, 1H), 2.46~2.55 (m, 1H), 4.31~4.37 (m, 1H), 4.45~4.53 (m, 1H), 4.60 (br s, 2H), 5.04~5.09 (m, 1H), 6.87 (t, J = 7.8, 1H), 6.96 (d, J = 7.6, 1H), 7.26 (d, J = 7.6, 1H) |
| 41 | 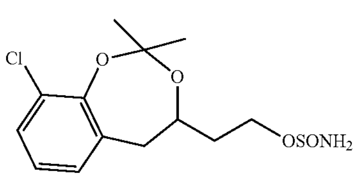 | 2-(9-chloro-2,2-dimethyl-4,5-dihydrobenzo[d][1,3]dioxepin-4-yl)ethyl sulfamate | Preparation example 115 | δ 1.43 (s, 3H), 1.55 (s, 3H), 1.80~1.93 (m, 2H), 2.32~2.35 (m, 1H), 3.80~3.83 (m, 2H), 4.63 (br s, 2H), 7.03~7.10 (m, 2H), 7.14~7.19 (m, 1H) |

TABLE 2-continued

Structure of Example

| Example No. | Structure | Name | Starting material | $^1$H NMR (400 MHz, CDCl$_3$) |
|---|---|---|---|---|
| 42 | 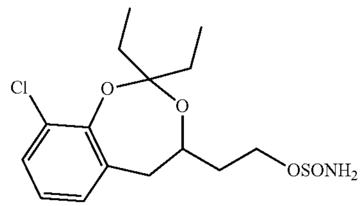 | 2-(9-chloro-2,2-diethyl-4,5-dihydrobenzo[d][1,3]dioxepin-4-yl)ethyl sulfamate | Preparation example 117 | δ 0.88~0.94 (m, 6H), 1.59~1.72 (m, 4H), 1.81~1.89 (m, 2H), 2.33~2.35 (m, 1H), 3.78~3.83 (m, 2H), 4.67 (br s, 2H), 7.02~7.09 (m, 2H), 7.14~7.18 (m, 1H) |
| 43 | 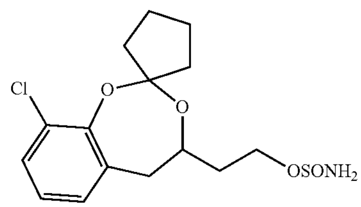 | 2-(9-chloro-4,5-dihydrospiro[benzo[d][1,3]dioxepine-2,1'-cyclopentan]-4-yl)ethyl sulfamate | Preparation example 119 | δ 1.64~1.71 (m, 3H), 1.78~1.83 (m, 5H), 1.85~1.93 (m, 2H), 2.31~2.35 (m, 1H), 3.80~3.86 (m, 2H), 4.68 (br s, 2H), 7.02~7.09 (m, 2H), 7.14~7.18 (m, 1H) |
| 44 | 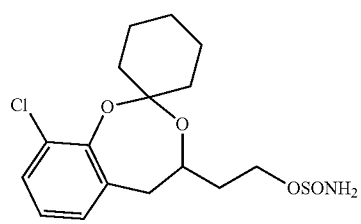 | 2-(9-chloro-4,5-dihydrospiro[benzo[d][1,3]dioxepine-2,1'-cyclohexan]-4-yl)ethyl sulfamate | Preparation example 121 | δ 1.54~1.66 (m, 10H), 1.81~1.90 (m, 2H), 2.31~2.35 (m, 1H), 3.78~3.82 (m, 2H), 4.53 (br s, 2H), 7.02~7.09 (m, 2H), 7.14~7.18 (m, 1H) |
| 45 | 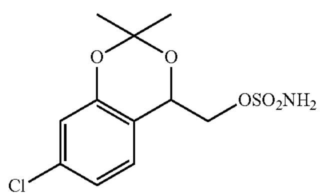 | (7-chloro-2,2-dimethyl-4H-benzo[d][1,3]diox-in-4-yl)methyl sulfamate | Preparation example 124 | δ 1.52 (s, 3H), 1.63 (s, 3H), 3.80~3.86 (m, 1H), 4.27~4.20 (m, 1H), 5.24 (br s, 2H), 6.77 (d, J = 8.0, 1H), 6.89 (d, J = 7.6, 1H), 7.19~7.15 (m, 1H), 7.27 (d, J = 7.6, 1H) |
| 46 | 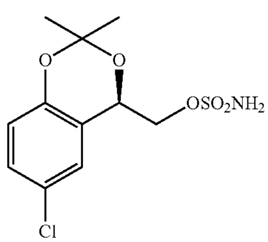 | ((R)-6-chloro-2,2-dimethyl-4H-benzo[d][1,3]diox-in-4-yl)methyl sulfamate | Preparation example 127 | δ 1.49 (s, 3H), 1.62 (s, 3H), 4.40~4.45 (m, 1H), 4.60 (dd, J = 2.8, 11.2, 1H), 5.08 (br s, 2H), 5.16 (dd, J = 2.8, 6.4, 1H), 6.81 (d, J = 8.8, 1H), 7.10 (d, J = 2.0, 1H), 7.19 (dd, J = 2.0, 8.9, 1H). |
| 47 | 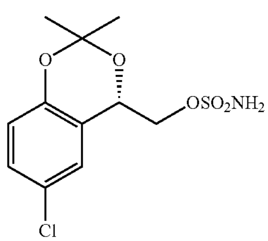 | ((S)-6-chloro-2,2-dimethyl-4H-benzo[d][1,3]diox-in-4-yl)methyl sulfamate | Preparation example 130 | δ 1.49 (s, 3H), 1.62 (s, 3H), 4.40~4.45 (m, 1H), 4.60 (dd, J = 2.8, 11.2, 1H), 5.08 (br s, 2H), 5.16 (dd, J = 2.8, 6.4, 1H), 6.81 (d, J = 8.8, 1H), 7.10 (d, J = 2.0, 1H), 7.19 (dd, J = 2.0, 8.9, 1H). |

TABLE 2-continued

| Example No. | Structure | Name | Starting material | $^1$H NMR (400 MHz, CDCl$_3$) |
|---|---|---|---|---|
| 48 | 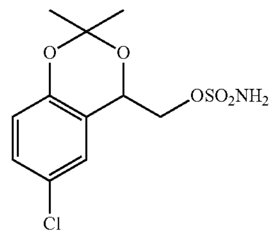 | (6-chloro-2,2-dimethyl-4H-benzo[d][1,3]diox-in-4-yl)methyl sulfamate | Preparation example 133 | δ 1.49 (s, 3H), 1.62 (s, 3H), 4.40~4.45 (m, 1H), 4.60 (dd, J = 2.8, 11.2, 1H), 5.08 (br s, 2H), 5.16 (dd, J = 2.8, 6.4, 1H), 6.81 (d, J = 8.8, 1H), 7.10 (d, J = 2.0, 1H), 7.19 (dd, J = 2.0, 8.9, 1H). |
| 49 | 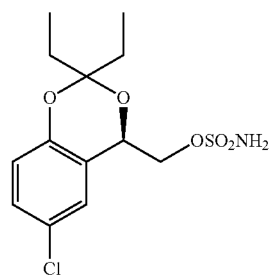 | ((R)-6-chloro-2,2-diethyl-4H-benzo[d][1,3]diox-in-4-yl)methyl sulfamate | Preparation example 135 | δ 0.92 (t, J = 7.2, 3H), 1.04 (t, J = 7.2, 3H), 1.76~1.88 (m, 4H), 4.43~4.48 (m, 1H), 4.59 (dd, J = 11.2, 3.2, 1H), 4.89 (br s, 2H), 5.13~5.15 (m, 1H), 6.82 (d, J = 8.8, 1H), 7.09 (d, J = 2.4, 1H), 7.20 (dd, J = 8.6, 2.4, 1H) |
| 50 | 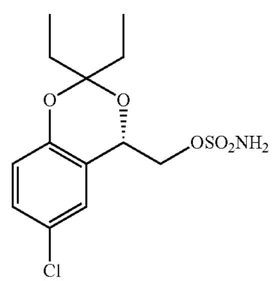 | ((S)-6-chloro-2,2-diethyl-4H-benzo[d][1,3]diox-in-4-yl)methyl sulfamate | Preparation example 137 | δ 0.92 (t, J = 7.2, 3H), 1.04 (t, J = 7.2, 3H), 1.76~1.88 (m, 4H), 4.43~4.48 (m, 1H), 4.59 (dd, J = 11.2, 3.2, 1H), 4.89 (br s, 2H), 5.13~5.15 (m, 1H), 6.82 (d, J = 8.8, 1H), 7.09 (d, J = 2.4, 1H), 7.20 (dd, J = 8.6, 2.4, 1H) |
| 51 | 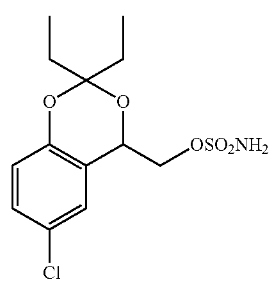 | (6-chloro-2,2-diethyl-4H-benzo[d][1,3]diox-in-4-yl)methyl sulfamate | Preparation example 139 | δ 0.92 (t, J = 7.2, 3H), 1.04 (t, J = 7.2, 3H), 1.76~1.88 (m, 4H), 4.43~4.48 (m, 1H), 4.59 (dd, J = 11.2, 3.2, 1H), 4.89 (br s, 2H), 5.13~5.15 (m, 1H), 6.82 (d, J = 8.8, 1H), 7.09 (d, J = 2.4, 1H), 7.20 (dd, J = 8.6, 2.4, 1H) |
| 52 | 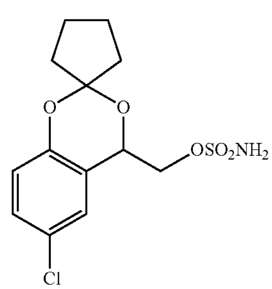 | (6-chloro-4H-spiro[benzo[d][1,3]dioxine-2,1'-cyclopentan]-4-yl)methyl sulfamate | Preparation example 141 | δ 1.45~1.50 (m, 4H), 1.74~1.89 (m, 4H), 4.25~4.30 (m, 1H), 4.58 (dd, J = 12.0, 3.2, 1H), 4.74 (br s, 2H), 5.05~5.08 (m, 1H), 6.81 (d, J = 8.8, 1H), 7.13~7.18 (m, 2H) |

TABLE 2-continued

Structure of Example

| Example No. | Structure | Name | Starting material | $^1$H NMR (400 MHz, CDCl$_3$) |
|---|---|---|---|---|
| 53 | 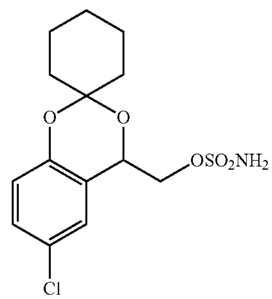 | (6-chloro-4H-spiro[benzo[d][1,3]dioxine-2,1'-cyclohexan]-4-yl)methyl sulfamate | Preparation example 143 | δ 1.45~1.5 (m, 4H), 1.74~1.89 (m, 6H), 4.25~4.30 (m, 1H), 4.58 (dd, J = 12.0, 3.2, 1H), 4.74 (br s, 2H), 5.05~5.08 (m, 1H), 6.81 (d, J = 8.8, 1H), 7.13~7.18 (m, 2H) |
| 54 | 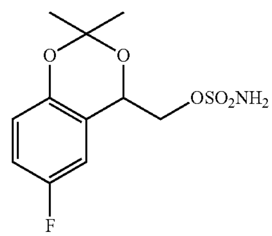 | (6-fluoro-2,2-dimethyl-4H-benzo[d][1,3]dioxin-4-yl)methyl sulfamate | Preparation example 146 | δ 1.51 (s, 3H), 1.63 (s, 3H), 4.47 (dd, J = 10.0, 6.0, 1H), 4.61 (dd, J = 12.0, 4.0, 1H), 4.85 (br s, 2H), 5.18~5.21 (m, 1H), 6.86~6.82 (m, 2H), 7.06~6.94 (m, 1H) |
| 55 | 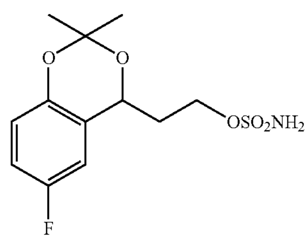 | 2-(6-fluoro-2,2-dimethyl-4H-benzo[d][1,3]dioxin-4-yl)ethyl sulfamate | Preparation example 159 | (DMSO) δ 1.42 (s, 3H), 1.51 (s, 3H), 1.97~2.05 (m, 1H), 2.42~2.49 m, 1H), 4.00~4.08 (m, 1H), 4.16~4.22 (m, 1H), 5.02 (dd, J = 2.0, 8.4, 1H), 6.80~6.83 (m, 1H), 7.01~7.06 (m, 1H), 7.13~7.16 (m, 1H), 7.49 (br s, 2H) |
| 56 | 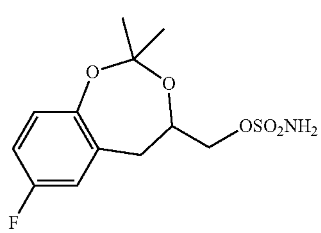 | (7-fluoro-2,2-dimethyl-4,5-dihydrobenzo[d][1,3]dioxepin-4-yl)methyl sulfamate | Preparation example 155 | (DMSO) δ 1.26 (s, 3H), 1.34 (s, 3H), 2.92 (d, J = 6.4, 2H), 3.59 (t, J = 7.4, 1H), 3.98 (dd, J = 6.0, 8.0, 1H), 4.32~4.38 (m, 1H), 7.16~7.21 (m, 1H), 7.26 (dd, J = 3.0, 9.4, 1H), 7.35 (dd, J = 5.0, 9.0, 1H), 8.13 (br s, 2H) |
| 57 | 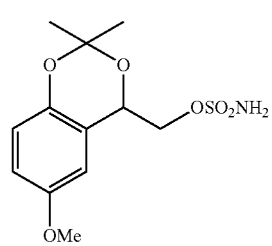 | (6-methoxy-2,2-dimethyl-4H-benzo[d][1,3]dioxin-4-yl)methyl sulfamate | Preparation example 162 | (DMSO) δ 1.44 (s, 3H), 1.62 (s, 3H), 3.78 (s, 3H), 4.51~4.32 (m, 1H), 4.64 (d, J = 12.0, 1H), 4.87 (br s, 2H), 5.17 (dd, J = 12.0, 4.0, 1H), 6.63~6.71 (m, 1H), 6.82~2.89 (m, 2H) |

Example 58: Sodium (R)-(((2,2-dimethyl-4H-benzo[d][1,3]dioxin-4-yl)methoxy)sulfonyl)amide Trihydrate

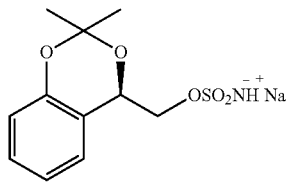

To stirred solution of ((R)-2,2-dimethyl-4H-benzo[d][1,3]dioxin-4-yl)methylsulfamate (Example 1, 91.3 g, 0.33 mol) in a mixture of MTBE and IPA (0.91 L, 3:1, v/v) was added 6 N NaOH aqueous solution (52 mL, 0.314 mol) at room temperature then stirred for 1 hr at 0° C. The resulting mixture was removed solvent. The concentrated residue was added IPA (46 mL) at room temperature then stirred for 30 min. The mixture was added MTBE (867 mL) then stirred for 1 hr at room temperature. Solid product was filtered and air-dried to give a title compound. (111 g, 85~99%).

Water content: 15.42%, 3.0 H$_2$O, MP: $1^{st}$ 51~52° C., $2^{nd}$ 133~135.4° C.

$^1$H NMR (400 MHz, DMSO-d$_6$) δ 1.42 (s, 3H), 1.53 (s, 3H), 4.15 (dd, J=6.0, 11.2, 1H), 4.33 (dd, J=2.4, 11.2, 1H), 5.22 (dd, J=2.4, 6.0, 1H), 6.79 (d, J=8.0, 1H), 6.98 (t, J=7.2, 1H), 7.18~7.23 (m, 2H)

According to the method described in Example 58, the following compounds of Examples 59 to 69 were prepared:

TABLE 3

Structure of Example

| Example No. | Structure | Name | Starting material | $^1$H NMR (400 MHz, DMSO) |
|---|---|---|---|---|
| 59 | 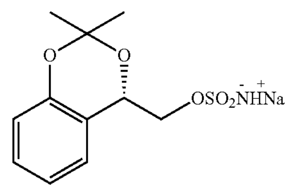 | Sodium (S)-(((2,2-dimethyl-4H-benzo[d][1,3]dioxin-4-yl)methoxy)sulfonyl)amide Trihydrate | Example 2 | δ 1.42 (s, 3H), 1.53 (s, 3H), 4.15 (dd, J = 6.0, 11.2, 1H), 4.33 (dd, J = 2.4, 11.2, 1H), 5.22 (dd, J = 2.4, 6.0, 1H), 6.79 (d, J = 8.0, 1H), 6.98 (t, J = 7.2, 1H), 7.18-7.23 (m, 2H) MP: 51.2~52.2, 135~137° C. |
| 60 | 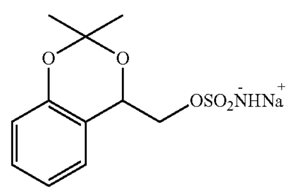 | Sodium (((2,2-dimethyl-4H-benzo[d][1,3]dioxin-4-yl)methoxy)sulfonyl)amide Trihydrate | Example 3 | δ 1.42 (s, 3H), 1.53 (s, 3H), 4.15 (dd, J = 6.0, 11.2, 1H), 4.33 (dd, J = 2.4, 11.2, 1H), 5.22 (dd, J = 2.4, 6.0, 1H), 6.79 (d, J = 8.0, 1H), 6.98 (t, J = 7.2, 1H), 7.18-7.23 (m, 2H) MP: 81~86, 132~135.6° C. |
| 61 | 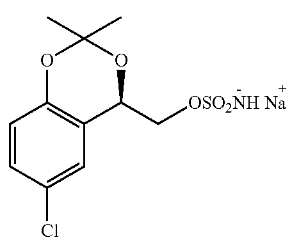 | Sodium (R)-(((6-chloro-2,2-dimethyl-4H-benzo[d][1,3]dioxin-4-yl)methoxy)sulfonyl)amide | Example 46 | (CDCl$_3$) δ 1.51 (S, 3H), 1.62 (s, 3H), 4.24~4.28 (m, 1H), 4.4 (dd, J = 12. 2.4, 1H), 5.27~5.29 (m, 1H), 6.84 (d, J = 8.8, 1H), 7.26 (dd, J = 8.6, 2.4, 1H), 7.31 (d, J = 2.1H). |
| 62 | 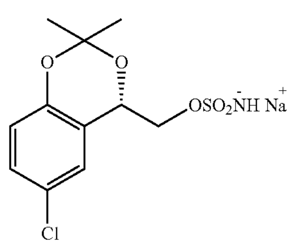 | Sodium (S)-(((6-chloro-2,2-dimethyl-4H-benzo[d][1,3]dioxin-4-yl)methoxy)sulfonyl)amide | Example 47 | (CDCl$_3$) δ 1.51 (S, 3H), 1.62 (s, 3H), 4.24~4.28 (m, 1H), 4.4 (dd, J = 12. 2.4, 1H), 5.27~5.29 (m, 1H), 6.84 (d, J = 8.8, 1H), 7.26 (dd, J = 8.6, 2.4, 1H), 7.31 (d, J = 2.1H) MP: 133.8~135.3° C. |

TABLE 3-continued

| Example No. | Structure | Name | Starting material | $^1$H NMR (400 MHz, DMSO) |
|---|---|---|---|---|
| 63 | | Sodium (((6-chloro-2,2-dimethyl-4H-benzo[d][1,3]diox-in-4-yl)methoxy)sulfonyl)amide | Example 48 | (D$_2$O) δ 1.51 (S, 3H), 1.62 (s, 3H), 4.24~4.28 (m, 1H), 4.4 (dd, J = 12. 2.4, 1H), 5.27~5.29 (m, 1H), 6.84 (d, J = 8.8, 1H), 7.26 (dd, J = 8.6, 2.4 1H), 7.31 (d, J = 2.1H). MP: 129.3~132.3° C. |
| 64 | | Sodium (R)-(((4H-spiro[benzo[d][1,3]dioxine-2,1'-cyclopentan]-4-yl)methoxy)sulfonyl)amide | Example 7 | δ 1.67~1.76 (m, 5H), 1.87~2.05 (m, 3H), 4.26 (dd, J = 4.8, 6.0 1H), 4.44 (dd, J = 2.8, 8.4 1H), 5.26 (dd, J = 2.8, 3.2, 1H), 6.84 (d, J = 7.2, 1H), 6.97 (dt, , J = 1.0, 7.4, 1H), 7.23 (m, 2H). MP: 132.9~134.9° C. |
| 65 | | Sodium (S)-(((4H-spiro[benzo[d][1,3]dioxine-2,1'-cyclopentan]-4-yl)methoxy)sulfonyl)amide | Example 8 | δ 1.67~1.76 (m, 5H), 1.87~2.05 (m, 3H), 4.26 (dd, J = 4.8, 6.0 1H), 4.44 (dd, J = 2.8, 8.4 1H), 5.26 (dd, J = 2.8, 3.2, 1H), 6.84 (d, J = 7.2, 1H), 6.97 (dt, J = 1.0, 7.4, 1H), 7.23 (m, 2H). MP: 121.2~131.9° C. |
| 66 | | Sodium (((4H-spiro[benzo[d][1,3]dioxine-2,1'-cylcopentan]-4-yl)methoxy)sulfonyl)amide | Example 9 | δ 1.67~1.76 (m, 5H), 1.87~2.05 (m, 3H), 4.26 (dd, J = 4.8, 6.0 1H), 4.44 (dd, J = 2.8, 8.4 1H), 5.26 (dd, J = 2.8, 3.2, 1H), 6.84 (d, J = 7.2, 1H), 6.97 (dt, J = 1.0, 7.4, 1H), 7.23 (m, 2H). MP: 145.5~148.9° C. |
| 67 | | Sodium ((6-chloro-(4H-spiro[benzo[d][1,3]dioxine-2,1'-cyclopentan]-4-yl)methoxy)sulfonyl)amide | Example 52 | (CDCl$_3$) δ 1.59~1.78 (m, 5H), 1.79~1.86 (m, 2H), 1.92~1.97 (m, 2H), 4.12~4.16 (m, 1H), 4.30 (dd, J = 11.4, 2.4, 1H), 5.20~5.22 (m, 1H), 6.78 (d, J = 8.8, 1H), 7.16~7.22 (m, 2H). MP: 68.6~72.3° C. |
| 68 | | Sodium ((2-(2,2-dimethyl-4H-benzo[d][1,3]diox-in-4-yl)ethoxy)sulfonyl)amide | Example 13 | (D$_2$O) δ 1.54 (s, 3H), 1.63 (s, 3H), 2.05~2.15 (m, 1H), 2.45~2.56 (m, 1H), 4.05~4.14 (m, 1H), 4.15~4.24 (m, 1H), 5.23~5.29 (m, 1H), 6.89 (d, J = 8.40, 1H), 7.09 (t, J = 7.40, 1H), 7.30 (t, J = 7.00, 1H) |

TABLE 3-continued

Structure of Example

| Example No. | Structure | Name | Starting material | ¹H NMR (400 MHz, DMSO) |
|---|---|---|---|---|
| 69 | 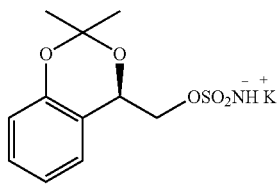 | Sodium ((2-(4H-spiro[benzo[d][1,3]dioxine2,1'-cyclopentan]-4-yl)ethoxy)sulfonyl)amide | Example 15 | (D₂O) δ 1.69~2.12 (m, 9H), 2.46~2.57 (m, 1H), 4.07~4.16 (m, 1H), 4.16~4.25 (m, 1H), 5.29 (q, j = 4.00 1H), 6.92 (q, J = 8.40, 1H), 7.10 (t, J = 7.60, 1H), 7.29 (q, J = 7.47, 1H) |

Example 70: Potassium (R)-(((2,2-dimethyl-4H-benzo[d][1,3]dioxin-4-yl)methoxy)sulfonyl)amide

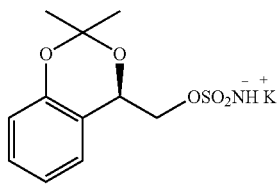

To a 250 ml flask, Potassium hydroxide (0.66 g, 11.7 mmol), ethanol (32 ml) were added. ((R)-2,2-dimethyl-4H-benzo[d][1,3]dioxin-4-yl)methyl sulfamate (Example 1, 3.2 g, 11.7 mmol) was added at RT. The reactants were stirred for 1 hr then evaporated under reduced pressure. Methyl-tert-butyl ether (64 ml), H₂O (0.26 ml) were added and stirred for 18 hr at RT. Solid was formed and filtered and washed with methyl-tert-butyl ether to obtain the title compound (2.8 g, 85%). mp 156.5~158.1° C.

¹H NMR (400 MHz, D₂O) δ 1.56 (s, 3H), 1.66 (s, 3H), 4.27~4.31 (m, 1H), 4.47 (dd, J=11.4, 2.4, 1H), 5.35~5.37 (m, 1H), 6.93 (d, J=7.6, 1H), 7.08~7.13 (m, 1H), 7.31~7.34 (m, 2H).

Example 71: Potassium (S)-(((2,2-dimethyl-4H-benzo[d][1,3]dioxin-4-yl)methoxy)sulfonyl)amide

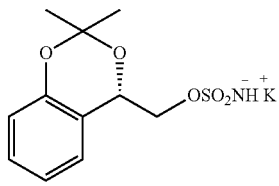

The substantially same method as described in Example 70 was conducted, except that ((S)-2,2-dimethyl-4H-benzo[d][1,3]dioxin-4-yl)methoxysulfonyl)amide (Example 2) was used instead of ((R)-2,2-dimethyl-4H-benzo[d][1,3]dioxin-4-yl)methyl sulfamate (Example 1), to obtain the title compound (5.1 g, 80~95%); mp: 153~156° C.

¹H NMR (400 MHz, DMSO-d₆) δ 1.42 (s, 3H), 1.52 (s, 3H), 3.86 (dd, J=6.4, 10.8, 1H), 4.08 (dd, J=3.6, 10.8, 1H), 5.06~5.16 (m, 1H), 6.77 (d, J=8.0, 1H), 6.92 (t, J=7.6, 1H), 7.16 (t, J=7.6, 1H), 7.26 (d, J=7.6, 1H)

Example 72: Potassium (((2,2-dimethyl-4H-benzo[d][1,3]dioxin-4-yl)methoxy)sulfonyl)amide

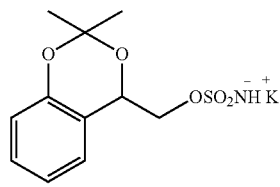

The substantially same method as described in Example 70 was conducted, except that 2,2-dimethyl-4H-benzo[d][1,3]dioxin-4-yl)methoxysulfonyl)amide (Example 3) was used instead of ((R)-2,2-dimethyl-4H-benzo[d][1,3]dioxin-4-yl)methyl sulfamate (Example 1), to obtain the title compound (1.1 g, 80~95%)

¹H NMR (400 MHz, DMSO-d₆) δ 1.42 (s, 3H), 1.52 (s, 3H), 3.78 (dd, J=5.6, 12.0, 1H), 4.13 (dd, J=3.6, 10.8, 1H), 5.07~5.10 (m, 1H), 6.77 (d, J=8.0, 1H), 6.91 (t, J=7.6, 1H), 7.17 (t, J=8.0, 1H), 7.26 (d, J=7.6, 1H)

Example 73: Lithium (S)-(((2,2-dimethyl-4H-benzo[d][1,3]dioxin-4-yl)methoxy)sulfonyl)amide

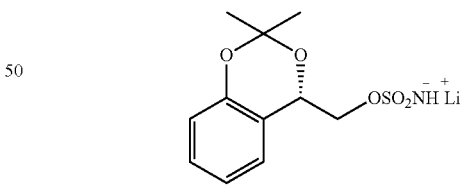

To a flask, n-Butyllithium (2.9 mL of 2.0M in hexane, 5.8 mmol) was added slowly to a solution of ((S)-2,2-dimethyl-4H-benzo[d][1,3]dioxin-4-yl)methyl sulfamate (Example 2, 1.6 g, 5.8 mmol) in THF at room temperature. The solvent was evaporated under reduced pressure. The solid was collected by filtration and dried, to obtain the title compound (1.8 g, 75~90%)

¹H NMR (400 MHz, DMSO-d₆) δ 1.42 (s, 3H), 1.52 (s, 3H), 3.86 (dl, J=6.4, 10.8, 1H), 4.09 (dd, J=3.6, 10.8, 1H), 5.06~5.08 (m, 1H), 6.77 (d, J=8.0, 1H), 6.91 (t, J=7.6, 1H), 7.17 (t, J=7.6, 1H), 7.26 (d, J=8.0, 1H)

Experimental Example 1: Evaluation of Antiallodynic Activity on Complete Freund's Adjuvant (CFA)-Induced Inflammatory Pain Model Male, Sprague-Dawley rats (200-220 g, Nara Bio, Korea) were habituated for 1 week before surgery and allowed free access to food and water throughout the experimentation. Room temperature and humidity were maintained at 24±2° C. and 50±10%, respectively.

CFA-induced inflammatory pain was induced by the procedure of Nagakura et al. (2003) and Gregory P. et al. (2010) with minor modifications. CFA (sigma, USA) was injected into the left plantar with a 100 ul volume under gaseous anesthesia with isoflurane and $NO_2$ with a 4:4 flow ratio. Sham controls were injected with 100 ul of saline and preparation of the vehicle controls were identical to the group treated with compound, except for administration of vehicles without compound in the vehicle control group.

Tactile sensitivity (mechanical allodynia) was evaluated using von Frey monofilaments before and after treatment, and the animals were included in the study only if the withdrawal threshold value was less than 4 g. One week after surgery, CFA-infused animals (n=4~6), sham-operated animals (n=12), and vehicle-operated animals (n=17) were tested for tactile sensitivity with von Frey monofilaments, with 3 trials for each animal. All animals were placed in a stainless steel mesh chamber and habituated for 30 min in the test cage. The tactile sensitivity for the ipsilateral hind paw was measured using the up-and-down method (Dixon, 1980) with seven von Frey monofilaments (0.4, 1, 2, 4, 6, 8, and 15 g) in 3 trials. The tactile sensitivity test was followed by Dixon's method (Dixon, 1980). The 50% paw withdrawal threshold for each paw was calculated using the following formula: [Xth] log=[vFr] log+ky where [vFr] is the force of the last von Frey used, k=0.2249 which is the average interval (in log units) between the von Frey monofilaments, and y is a value that depends upon the pattern of the withdrawal responses (Dixon, 1980). If an animal did not respond to the highest von Frey hair (15 g), the paw was assigned a value of 18.4 g.

The antiallodynic effect of the compound of Example was evaluated at the doses of 10, 30 and 60 mg/kg (n=4~6), and were intraperitoneally administered in a volume of 5 ul/g by bodyweight in a vehicle of 30% (v/v) PEG. The test was performed at the peak time of efficacy (0.5 hr) after compound administration.

The relative values compared to the sham (% control) were calculated and are shown in Table 4, which show an antiallodynic effect of the compound of examples in the CFA-induced pain model in rats.

TABLE 4

Antiallodynic effect of the compound of Examples in the CFA-induced pain model

| Example No | CFA model: ED50 mg/kg |
|---|---|
| 2 | 18.8 (0.5 h) |
| 6 | #50 (64.6%, 0.5 h) |
| 8 | #50 (74.8%, 0.5 h) |
| 10 | #25 (37.2%, 0.5 h) |
| 16 | #50 (38.9%, 0.5 h) |
| 18 | #50 (91.7%, 0.5 h) |
| 20 | #50 (69.0%, 0.5 h) |
| 26 | #50 (34.2%, 0.5 h) |
| 29 | #25 (43.9%, 0.5 h) |
| 32 | #50 (51.9%, 0.5 h) |
| 35 | #50 (15.5%, 0.5 h) |
| 45 | #50 (33.1%, 0.5 h) |
| 46 | #50 (36.4%, 0.5 h) |
| 47 | #50 (100%, 0.5 h) |
| 48 | #50 (21.7%, 0.5 h) |
| 51 | #50 (23.3%, 0.5 h) |
| 53 | #25 (57.3%, 0.5 h) |
| 54 | #25 (82.9%, 0.5 h) |
| 57 | #25 (39.1%, 0.5 h) |
| 58 | 23.3 (0.5 h) |
| 59 | 20.2 (0.5 h) |
| 60 | 25.0 (1 h) |
| 63 | #25 (16.9%) |
| 65 | 89.1 (0.5 h) |
| 70 | #25 (10.5%, 0.5 h) |
| 71 | #25 (24.7%) |
| 72 | #50 (67.1%, 0.5 h) | concentration administered and effect (%) compared to that of control-treated group with vehicle only

Experimental Example 2: Evaluation of Antiallodynic Activity in the Chung Model Male Sprague-Dawley rats (200-220 g, Orient Bio, Korea) were habituated for 1 week before the experiment and allowed free access to food and water throughout the experimentation. Room temperature and humidity were maintained at 24±2° C. and 50±10%, respectively. The neuropathic surgery (SNL, Spinal Nerve Ligation) model was done as described in Kim and Chung (1992). Briefly, an animal was put under gaseous anesthesia with isoflurane and $NO_2$ with a 4:4 flow ratio. The left lumbar spinal nerves L5 and L6 were isolated and tightly ligated with 4-0 silk thread. The wound was treated with a gentamicin antibiotic solution (4 mg/kg, 4 ul/g by bodyweight), and the wound muscle was closed with Catgut® chrome 4/0 thread and the skin was closed with Dafilon 4/0 thread. Sham controls were prepared in the same manner with the spinal nerves were exposed, but no ligated L5 and L6 nerves. Preparation of the vehicle controls were identical to the group treated with compound, except for administration of vehicles without compound in the vehicle control group.

Tactile sensitivity (mechanical allodynia) was evaluated using von Frey monofilaments before and after treatment and animals the animals were included in the study only if the withdrawal threshold value was less than 4 g. One week after surgery, SNL-operated animals (n=4~6), sham-operated animals (n=4~10) and vehicle-operated animals (n=4~13) were tested for tactile sensitivity with von Frey monofilaments with 3 trials in each animal. All animals were placed in a stainless steel mesh chamber and habituated for 30 min in the test cage. The tactile sensitivity for ipsilateral hind paw was measured using the up-and-down method (Dixon, 1980) with seven von Frey monofilaments (0.4, 1, 2, 4, 6, 8, and 15 g) in 3 trials. The tactile sensitivity test was followed by Dixon's method (Dixon, 1980). The 50% paw withdrawal threshold for each paw was calculated using the following formula: [Xth] log=[vFr] log+ky where [vFr] is the force of the last von Frey used, k=0.2249 which is the average interval (in log units) between the von Frey monofilaments, and y is a value that depends upon the pattern of withdrawal responses (Dixon, 1980). If an animal did not respond to the highest von Frey hair (15 g), the paw was assigned a value of 18.4 g.

All animals were fasted for 18 h before the administration of the compounds. The antiallodynic effect of the compounds were evaluated at the various doses (n=5~6), orally administered in a volume of 5 ul/g by bodyweight in a vehicle of 30% (v/v) PEG 400 (Example 7) or 20% (v/v) Tween 80 (Examples 5 and 6) or saline. The test was performed at the peak time of efficacy (1 hr) after compound administration.

The relative values compared to the sham group (% control) were calculated and are shown in Table 5, which show an antiallodynic effect of the test compounds in the SNL model in rats.

TABLE 5

Antiallodynic effect of the compound of examples in the SNL model

| Example No | SNL model: ED50 mg/kg |
|---|---|
| 1 | 9.9 (1 h) |
| 2 | 4.5 (1 h) |
| 3 | #3.5 (35.0%, 0.5 h) |
| 11 | #3.5 (18.6%) |
| 12 | #3.5 (18.7%, 1 h) |
| 14 | #3.5 (37.9%) |
| 17 | #3.5 (16.8%, 0.5 h) |
| 19 | #3.5 (33.3%) |
| 58 | 8.9 (1 h) |
| 59 | 4.5 (1 h) |
| 60 | 3.5 (1 h) |
| 61 | #3.5 (20.9%) |
| 62 | #3.5 (32.6%) |
| 63 | #3.5 (32.9%) |
| 64 | #3.5 (22.5%) |
| 65 | 3.4 (0.5 h) |
| 66 | #3.5 (59.5%, 0.5 h) |
| 67 | #3.5 (49.1%) |
| 68 | #3.5 (25.0%, 0.5 h) |
| 70 | #3.5 (46.7%, 1 h) |
| 71 | #3.5 (15.9%, 0.5 h) |
| 73 | #3.5 (13.5%, 0.5 h) | the concentration administered and effect (%) compared to that of control-treated group with vehicle only Experimental Example 3: Writhing Test To examine the pain relief effect of the sulfamate derivative compounds, a writhing test was referring to Fischer, L. G. et al. (2008).

ICR mice (male, 24-28 g; Orient Bio, Korea) were habituated before test in test room for 1 hour. Animals were fasted for 2 hr before administration of compounds. Each of compound 1, 2, 5, 6, 7, 8, 9 and 10 was orally administered at the dose of 20 mg/kg, 10 ul/g by bodyweight (n=3~5/group). All compounds were dissolved in a vehicle of 30% (v/v) PEG 400 or 20% (v/v) Tween 80. The control group was treated with the vehicle without compounds.

One hour after the administration of the compounds, 0.6% acetic acid at a dose of 10 ul/g by bodyweight was injected into the mice. Animals were habituated in the cage for 5 min. 5 min after habituation, the number of writhes (abdominal constriction) was counted for 15 minutes referring to Korzeniewska-Rybicka, I. et al. (1998) and compared with that of the control.

The relative values compared to the control (% control) were calculated and are shown in Table 6

TABLE 6

Effect of the compound of examples in the writhing test.

| Example No | Writh test: ED50 mg/kg |
|---|---|
| 1 | 56.8 (0.25 h) |
| 2 | 152.5 (1 h) |
| 3 | #80 (63.9%, 0.5 h) |
| 59 | 81.4 (0.5 h) |
| 60 | 21.0 (0.5 h) |
| 65 | 55.1 (0.5 h) |
| 70 | #80 (29.1%, 1 hr) | the concentration administered and effect (%) compared to that of control treated with vehicle only Experimental Example 4: Evaluation of Antiallodynic Activity on Post Operative Pain-Induced Pain Model Male Sprague-Dawley rats (Orient Bio, Korea), 300-320 g, total of 201 rats were used (details in Table 7). Rats were habituated at least 3 days before surgery and free access to food and water (room temperature and humidity were maintained at 241±2° C. and 50±10%, respectively). The process of performing the post-operation model's surgery was adapted from Brennan et al (1996). At first, rats with allodynia (threshold valueless than 8 g) were excluded in Pre-von Frey Test. During the post-operation surgery, rats were anesthetized under gaseous anesthesia with 2% isoflurane. Rats were laid face down on a plate fixed at 37° C. to prevent against hypothermia. The ipsilateral plantar aspect (left side) of the hind paw was prepared in a sterile manner with a 10% povidone-iodine solution. A longitudinal incision (1 cm) (FIG. 2-A) was made with a blade (number 11) through the skin and fascia of the ipsilateral plantar aspect of the foot, starting from 0.5 cm below the proximal edge of the heel and extending toward the toes. Rats' plantar muscles were elevated and incised longitudinally (FIG. 2-B). After hemostasis with gentle pressure, the skin was opposed with 2 mattress sutures (4-0 Dafilon) (FIG. 2-C). The wound site was covered with a 10% povidone-iodine solution gauze and injected with antibiotics (gentamicin, 8 mg/kg, ip). The sutures were removed under halothane anesthesia approximately 30 hours later, at the end of post-operative day 1.

After 2-3 days of recovery, rats with a good response (threshold less than 4 g) in Pre-von Frey Test were selected. According to this response, we made three groups with each group having equal average responses: Group 1, post-operation and drug treated; Group 2, post-operation and vehicle treated; Group 3, no post-operation and vehicle treated. In this study, Group 3 was the sham control (positive) group. The group 2 was used to check for possible failures to generate post-operative pain.

For efficacy measure, the threshold value of group C was assigned 100% efficacy, and the percentage of the threshold values of group A compared to group C (for each different dose level) were calculated as the efficacies. Base on these efficacy values, ED50 was calculated using log fitting. If there was no clear ED50, then we marked the percent efficacy at the highest tested dose or larger than highest tested dose.

For pain threshold test, all animals were placed in a stainless steel meshed chamber and habituated for 30 min in the test box. The tactile sensitivity of the ipsilateral hind paw was measured using the up-and-down method (Dixon, 1980) with seven von Frey monofilaments (0.4, 1, 2, 4, 6, 8, and 15 g) using 3 trials. The 50% paw withdrawal threshold for each paw was calculated using the following formula: [Xth] log=[vFr] log+ky, where [vFr] is the force of the last von Frey filament used, k=0.2249 which is the average interval (in log units) between the von Frey monofilaments, y which is a value that depends upon the pattern of withdrawal responses, and Xth which is the threshold value (Dixon, 1980). If an animal did not respond to the highest von Frey hair (15 g), then the threshold value was assigned as 18.4.

Drugs were dissolved 30% PEG400 for example 60, 0.9% saline for Pregabalin, 20% Tween80 for Tylenol, 0.9% saline for Topiramate. These vehicles were selected depending on the compound's solubility. Intraperitoneal injection (5 µl/g) was done for all drugs.

The relative values compared to the sham (% control) were calculated and shown in Table 8, which show an antiallodynic effect of the compound of examples on Post operation-induced pain model in rats.

TABLE 7

Number of animals used in this study

| | Group | example 60 | Pregabalin | Tylenol | Topiramate |
|---|---|---|---|---|---|
| A | Post-operative & Drug treated | 35 | 18 | 18 | 6 |
| B | Post-operative & Vehicle treated | 36 | 18 | 18 | 6 |
| C | Sham | 24 | 6 | 12 | 4 |

Overall experimental timeline is depicted in FIG. 1 and more detailed procedures are explained in the following sections.

TABLE 8

Antiallodynic effect of the compound of examples on Post operation-induced pain model

| Example No | Post Operation: ED50 mg/kg |
|---|---|
| 2 | 14.9 (0.5 h) |
| 58 | 19.4 (0.5 h) |
| 59 | 10.9 (0.5 h) |
| 60 | 18.9 (0.5 h) |
| 63 | #18.9 (26.6%) |
| 65 | 31.8 (0.5 h) |
| 70 | #18.9 (22.0%, 0.5 h) | the concentration administered and effect (%) compared to that of control treated with vehicle only

Experimental Example 5: Evaluation of Antiallodynic Activity in the Streptozotocin (STZ)-Induced Diabetic Pain Model Male, Sprague-Dawley rats (200-220 g, Nara Bio, Korea) were habituated for 1 week before surgery and allowed free access to food and water throughout the experimentation. Room temperature and humidity were maintained at 24±2° C. and 50±10%, respectively.

The STZ-induced diabetic pain model was established with a modified method of Rakieten et al. (1963) and Bertrand Aubel et al. (2004). All animals were fasted for 4 to 6 hr prior to STZ injection. STZ (sigma, USA) was dissolved in 20 mM sodium citrate buffer, pH 5.5 (Sigma, USA) and intraperitoneally injected at 75 mg/kg, 4 ul/g by bodyweight into the rats. Sham controls were injected with same volume of 20 mM sodium citrate buffer, pH 5.5, and vehicle controls were identical to STZ model except for administration of vehicles without treatment. Rats were supplied with 10% sucrose water for 2 days to protect against sudden hypoglycemia, 3 days later, the induction of diabetes was checked by the measurement of tail vein blood glucose levels with a blood glucose meter. (LifeScan One-Touch Ultra, USA). If blood glucose was not >300 mg/dl by 72 hr, the rat was excluded from the diabetic group.

Tactile sensitivity (mechanical allodynia) was evaluated using von Frey monofilaments before and after treatment of the compound of Examples and the animals were included in the study only if the withdrawal threshold value was less than 4 g. One week after surgery, diabetic animals (n=6), sham controls (n=12), and vehicle control (n=18) were tested for tactile sensitivity with von Frey monofilaments with 3 trials in each animal. All animals were placed in a stainless steel mesh chamber and habituated for 30 min in the test cage. The tactile sensitivity for the ipsilateral hind paw was measured using the up-and-down method (Dixon, 1980) with seven von Frey monofilaments (0.4, 1, 2, 4, 6, 8, and 15 g) in 3 trials. The tactile sensitivity test was followed by Dixon's method (Dixon, 1980). The 50% paw withdrawal threshold for each paw was calculated using the following formula: [Xth] log=[vFr] log+ky where [vFr] is the force of the last von Frey used, k=0.2249 which is the average interval (in log units) between the von Frey monofilaments, and y is a value that depends upon the pattern of withdrawal responses (Dixon, 1980). If an animal did not respond to the highest von Frey hair (15 g), the paw was assigned a value of 18.4 g.

The antiallodynic effect of the compound of examples was evaluated at the doses of 10, 30 and 60 mg/kg (n=6), intraperitoneally administrated in a volume of 5 ul/g by bodyweight in a vehicle of 30% (v/v) PEG. The test was performed at the peak time of efficacy (0.5 hr) after compound administration.

The relative values compared to the sham (% control) were calculated and shown in Table 9, which show an antiallodynic effect of the compound of examples on STZ-induced pain model in rats.

TABLE 9

Antiallodynic effect of the compound of examples on STZ-induced pain model

| Example No | STZ model: ED50 mg/kg |
|---|---|
| 2 | 27.4 (0.5 h) |
| 60 | 16.1 (0.5 h) |
| 65 | #100 (25.7%, 0.5 h) | the concentration administered and effect (%) compared to that of control-treated group with vehicle only

Experimental Example 6: Hot-Plate Test

To examine the pain relief effect of the sulfamate derivative compounds, a hot-plate test was conducted referring to Current Protocols in Neuroscience; Behavioral Neuroscience Unit 8.9.

ICR mice (male, 30-35 g; Orient Bio, Korea) were habituated before the test in the test room for 1 hour. Animals were fasted 2 hr before administration of the compounds. Each of Compounds 1, 2, 3, 4, 5, 63, 65, and 67 was orally administered at the dose of 150 mg/kg, 10 ul/g by bodyweight (n=7~10/group). All compounds were dissolved in a vehicle of 30% (v/v) PEG 400 or 20% (v/v) Tween 80. The control group was treated with vehicle without treatment compounds.

0.5 hr after the administration of compounds, the mice were put on a hot plate pre-heated to 55±1° C. (Hu, X. et al, 2008), and then, the withdrawal latency was measured (cut-off time: 30 sec) until the point when each mouse was taking a paw off from the plate, shaking, licking a paw or hind leg, or jumping from the plate. The relative values compared to the control (% control) were calculated and are shown in Table 10.

TABLE 10

Effect of the compound of examples in the hot-plate test.

| Example No | Hot plate test: ED50 mg/kg |
|---|---|
| 2 | 169.5 (0.5 h) |
| 60 | #170 (196.2%) | if the concentration administered and effect (%) compared to that of control-treated group with vehicle only Experimental Example 7: Evaluation of Antiallodynic Activity in the Vincristine-Induced Pain Model Male, Sprague-Dawley rats (300-320 g, Nara Bio, Korea) were habituated for 1 week before surgery and allowed free access to food and water throughout the experimentation. Room temperature and humidity were maintained at 24±2° C. and 50±10%, respectively.

The vincristine-induced pain model was established by the procedure of Natsuko et al. (2001) with minor modifications. Vincristine was intravenously infused continuously for 14 days using a mini-osmotic pump as follows: Vincristine sulfate solution (Hospira, Australia) was diluted with 0.9% saline to a final dose of 30 ug/kg. The pumps (Alzet Model 2002, USA) were filled with the vincristine solution and primed by incubation at 37° C. for 4 h before the infusion. Briefly, animals were put under gaseous anesthesia with isoflurane and NO with a 4:4 flow ratio. A catheter made from PE-60 tubing was inserted into an external jugular vein in the rat. Sham controls were prepared in the same manner, with the external jugular vein exposed, but not cut down. Preparation of the vehicle controls were identical to the group treated with compound, except for administration of vehicles without compound in the vehicle control group.

Tactile sensitivity (mechanical allodynia) was evaluated using von Frey monofilaments before and after treatment, and the animals were included in the study only if the withdrawal threshold value was less than 4 g. One week after surgery, vincristine-infused animals (n=6), sham-operated animals (n=12) and vehicle-operated (n=18) animals were tested for tactile sensitivity with von Frey monofilaments with 3 trials in each animal. All animals were placed in a stainless steel mesh chamber and habituated for 30 min in the test cage. The tactile sensitivity for the ipsilateral hind paw was measured using the up-and-down method (Dixon, 1980) with seven von Frey monofilaments (0.4, 1, 2, 4, 6, 8, and 15 g) in 3 trials. The tactile sensitivity test was followed by Dixon's method. The 50% paw withdrawal threshold for each paw was calculated using the following formula: [Xth] log=[vFr] log+ky where [vFr] is the force of the last von Frey used, k=0.2249 which is the average interval (in log units) between the von Frey monofilaments, and y is a value that depends upon the pattern of withdrawal responses (Dixon, 1980). If an animal did not respond to the highest von Frey hair (15 g), the paw was assigned a value of 18.4 g.

The antiallodynic effect of the compound of the examples was evaluated at the doses of 1, 5 and 10 mg/kg (n=6), intraperitoneally administered in a volume of 5 ul/g by bodyweight in a vehicle of 30% (v/v) PEG. The test was performed at the peak time of efficacy (0.5 hr) after compound administration.

The relative values compared to the sham (% control) were calculated and are shown in Table 11, which show an antiallodynic effect of the compound of examples in the vincristine-induced pain model in rats.

TABLE 11

Antiallodynic effect of the compound of examples in the Vincristine-induced pain model

| Example No | Vincristine model: ED50 mg/kg |
|---|---|
| 58 | 6.2 (0.5 h) |
| 59 | 2.6 (0.5 h) |
| 60 | 2.4 (0.5 h) |
| 65 | 8.2 (0.5 h) |
| 70 | #2.4 (36.2%, 0.5 h) |
| 71 | #2.4 (96.2%) | the concentration administered and effect (%) compared to that of control treated with vehicle only

[Statistical Analysis]

The obtained results are shown as mean±sem. The difference between the groups was statistically analyzed by ANOVA, and then, further examined by Dunnett's test or Bonferroni test. If p is less than 0.05, it was determined that the difference between the groups had statistical significance.

The invention claimed is:
1. A compound represented by the following formula 1 or a pharmaceutically acceptable salt thereof:

[Chemical Formula 1]

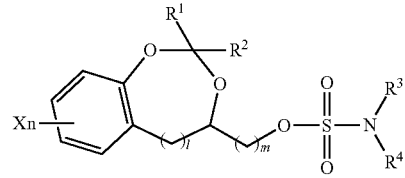

wherein X is selected from the group consisting of hydrogen, hydroxyl, $C_1$-$C_5$ alkoxy, $C_1$-$C_5$ alkyl, $C_2$-$C_5$ alkenyl, $C_6$-$C_{10}$ aryl, $C_1$-$C_5$ alkoxycarbonyl, carboxyl, $C_2$-$C_5$ acyl, $C_1$-$C_5$ alkylthio, cyano, nitro, amine, $C_1$-$C_5$ alkylamine and halogen;

$R^1$ and $R^2$ are each independently selected from the group consisting of hydrogen, $C_1$-$C_5$ alkyl group, $C_2$-$C_5$ alkenyl and $C_6$-$C_{10}$ aryl group, or $R_1$ and $R_2$ together with the carbon atom to which they attach form a $C_3$-$C_{12}$ cycloalkyl group;

$R^3$ and $R^4$ are each independently hydrogen or $C_1$-$C_3$ alkyl; and l, m and n are each independently an integer of 0 to 4.

2. The compound or the pharmaceutically acceptable salt thereof according to claim 1, wherein X is H, OMe, F, or I; and n is an integer from 1-4.

3. The compound or the pharmaceutically acceptable salt thereof according to claim 1, wherein l or m are each independently an integer 0 or 1.

4. The compound or the pharmaceutically acceptable salt thereof according to claim 1, wherein $R^1$ and $R^2$ are each independently methyl, ethyl, isopropyl or $R^1$ and $R^2$ together with the carbon atom to which they attach form a cyclopentyl or a cyclohexyl group.

5. The compound or the pharmaceutically acceptable salt thereof according to claim 1, wherein $R^3$ and $R^4$ are each independently hydrogen or methyl.

6. The compound or the pharmaceutically acceptable salt thereof according to claim 1, wherein X is chlorine, fluorine, iodine, bromine, methoxy or H;
n is an integer from 1-4;
$R^1$ and $R^2$ are each dependently selected from the group consisting of methyl, ethyl and isopropyl, or $R_1$ and $R_2$ together with the carbon atom to which they attach form a cyclopentyl or a cyclohexyl ring;
$R^3$ and $R^4$ are each dependently selected from the group consisting of H, methyl, ethyl, and isopropyl;
l and m are each dependently an integer from 0, 1 or 2.

7. The compound or the pharmaceutically acceptable salt thereof according to claim 1, wherein the compound is selected from the group consisting of:
((R)-2,2-dimethyl-4H-benzo[d][1,3]dioxin-4-yl)methyl sulfamate;
((S)-2,2-dimethyl-4H-benzo[d][1,3]dioxin-4-yl)methyl sulfamate;
(2,2-dimethyl-4H-benzo[d][1,3]dioxin-4-yl))methyl sulfamate;
((R)-2,2-diethyl-4H-benzo[d][1,3]dioxin-4-yl)methyl sulfamate;
((S)-2,2-diethyl-4H-benzo[d][1,3]dioxin-4-yl)methyl sulfamate;
(2,2-diethyl-4H-benzo[d][1,3]dioxin-4-yl))methyl sulfamate;
((R)-4H-spiro[benzo[d][1,3]dioxine-2,1'-cyclopentan]-4-yl)methyl sulfamate;
((S)-4H-spiro[benzo[d][1,3]dioxine-2,1'-cyclopentan]-4-yl)methyl sulfamate;
(4H-spiro[benzo[d][1,3]dioxine-2,1'-cyclopentan]-4-yl)methyl sulfamate;
((R)-4H-spiro[benzo[d][1,3]dioxine-2,1'-cyclohexan]-4-yl)methyl sulfamate;
((S)-4H-spiro[benzo[d][1,3]dioxine-2,1'-cyclohexan]-4-yl)methyl sulfamate;
(4H-spiro[benzo[d][1,3]dioxine-2,1'-cyclohexan]-4-yl)methyl sulfamate;
2-(2,2-dimethyl-4H-benzo[d][1.3]dioxin-4-yl)ethyl sulfamate;
2-(2,2-diethyl-4H-benzo[d][1.3]dioxin-4-yl)ethyl sulfamate;
2-(4H-spiro[benzo[d][1.3]dioxine-2,1'-cyclopentan]-4-yl)ethyl sulfamate;
2-(4H-spiro[benzo[d][1.3]dioxine-2,1'-cyclohexan]-4-yl)ethyl sulfamate;
(2,2-dimethyl-4,5-dihydrobenzo[d][1,3]dioxepin-4-yl)methyl sulfamate;
(2,2-diethyl-4,5-dihydrobenzo[d][1,3]dioxepin-4-yl)methyl sulfamate;
(4,5-dihydrospiro[benzo[d][1,3]dioxepine-2,1'-cyclopentan]-4-yl)methyl sulfamate;
(4,5-dihydrospiro[benzo[d][1,3]dioxepine-2,1'-cyclohexan]-4-yl)methyl sulfamate;
2-(2,2-dimethyl-4,5-dihydrobenzo[d][1,3]dioxepin-4-yl)ethyl sulfamate;
2-(2,2-diethyl-4,5-dihydrobenzo[d][1,3]dioxepin-4-yl)ethyl sulfamate;
2-(4,5-dihydrospiro[benzo[d][1,3]dioxepine-2,1'-cyclopentan]-4-yl)ethyl sulfamate;
2-(4,5-dihydrospiro[benzo[d][1,3]dioxepine-2,1'-cyclohexan]-4-yl)ethyl sulfamate;
((R)-8-chloro-2,2-dimethyl-4H-benzo[d][1,3]dioxin-4-yl)methyl sulfamate;
((S)-8-chloro-2,2-dimethyl-4H-benzo[d][1,3]dioxin-4-yl)methyl sulfamate;
(8-chloro-2,2-dimethyl-4H-benzo[d][1,3]dioxin-4-yl)methyl sulfamate;
((R)-8-chloro-2,2-diethyl-4H-benzo[d][1,3]dioxin-4-yl)methyl sulfamate;
((S)-8-chloro-2,2-diethyl-4H-benzo[d][1,3]dioxin-4-yl)methyl sulfamate;
(8-chloro-2,2-diethyl-4H-benzo[d][1,3]dioxin-4-yl)methyl sulfamate;
((R)-8-chloro-4H-spiro[benzo[d][1,3]dioxine-2,1'-cyclopentan]-4-yl)methyl sulfamate;
((S)-8-chloro-4H-spiro[benzo[d][1,3]dioxine-2,1'-cyclopentan]-4-yl)methyl sulfamate;
(8-chloro-4H-spiro[benzo[d][1,3]dioxine2,1'-cyclopentan]-4-yl)methyl sulfamate;
((R)-8-chloro-4H-spiro[benzo[d][1,3]dioxine-2,1'-cyclohexan]-4-yl)methyl sulfamate;
((S)-8-chloro-4H-spiro[benzo[d][1,3]dioxine-2,1'-cyclohexan]-4-yl)methyl sulfamate;
(8-chloro-4H-spiro[benzo[d][1,3]dioxine-2,1'-cyclohexan]-4-yl)methyl sulfamate;
2-(8-chloro-2,2-dimethyl-4H-benzo[d][1,3]dioxin-4-yl)ethyl sulfamate;
2-(8-chloro-2,2-diethyl-4H-benzo[d][1,3]dioxin-4-yl)ethyl sulfamate;
2-(8-chloro-4H-spiro[benzo[d][1,3]dioxine-2,1'-cyclopentan]-4-yl)ethyl sulfamate;
2-(8-chloro-4H-spiro[benzo[d][1,3]dioxine-2,1'-cyclohexan]-4-yl)ethyl sulfamate;
2-(9-chloro-2,2-dimethyl-4,5-dihydrobenzo[d][1,3]dioxepin-4-yl)ethyl sulfamate;
2-(9-chloro-2,2-diethyl-4,5-dihydrobenzo[d][1,3]dioxepin-4-yl)ethyl sulfamate;
2-(9-chloro-4,5-dihydrospiro[benzo[d][1,3]dioxepine-2,1'-cyclopentan]-4-yl)ethyl sulfamate;
2-(9-chloro-4,5-dihydrospiro[benzo[d][1,3]dioxepine-2,1'-cyclohexan]-4-yl)ethyl sulfamate;
(7-chloro-2,2-dimethyl-4H-benzo[d][1,3]dioxin-4-yl)methyl sulfamate;
((R)-6-chloro-2,2-dimethyl-4H-benzo[d][1,3]dioxin-4-yl)methyl sulfamate;
((S)-6-chloro-2,2-dimethyl-4H-benzo[d][1,3]dioxin-4-yl)methyl sulfamate;
(6-chloro-2,2-dimethyl-4H-benzo[d][1,3]dioxin-4-yl)methyl sulfamate;
((R)-6-chloro-2,2-diethyl-4H-benzo[d][1,3]dioxin-4-yl)methyl sulfamate;
((S)-6-chloro-2,2-diethyl-4H-benzo[d][1,3]dioxin-4-yl)methyl sulfamate;
(6-chloro-2,2-diethyl-4H-benzo[d][1,3]dioxin-4-yl)methyl sulfamate;
(6-chloro-4H-spiro[benzo[d][1,3]dioxine-2,1'-cyclopentan]-4-yl)methyl sulfamate;
(6-chloro-4H-spiro[benzo[d][1,3]dioxine-2,1'-cyclohexan]-4-yl)methyl sulfamate;
(6-fluoro-2,2-dimethyl-4H-benzo[d][1,3]dioxin-4-yl) methyl sulfamate;

2-(6-fluoro-2,2-dimethyl-4H-benzo[d][1,3]dioxin-4-yl) ethyl sulfamate;
(7-fluoro-2,2-dimethyl-4,5-dihydrobenzo[d][1,3]dioxepin-4-yl)methyl sulfamate;
(6-methoxy-2,2-dimethyl-4H-benzo[d][1,3]dioxin-4-yl) methyl sulfamate;
Sodium (R)-(((2,2-dimethyl-4H-benzo[d][1,3]dioxin-4-yl)methoxy)sulfonyl)amide Trihydrate;
Sodium (S)-(((2,2-dimethyl-4H-benzo[d][1,3]dioxin-4-yl)methoxy)sulfonyl)amide Trihydrate;
Sodium (((2,2-dimethyl-4H-benzo[d][1,3]dioxin-4-yl)methoxy)sulfonyl)amide Trihydrate;
Sodium (R)-(((6-chloro-2,2-dimethyl-4H-benzo[d][1,3]dioxin-4-yl)methoxy)sulfonyl)amide;
Sodium (S)-(((6-chloro-2,2-dimethyl-4H-benzo[d][1,3]dioxin-4-yl)methoxy)sulfonyl)amide;
Sodium (((6-chloro-2,2-dimethyl-4H-benzo[d][1,3]dioxin-4-yl)methoxy)sulfonyl)amide;
Sodium (R)-(((4H-spiro[benzo[d][1,3]dioxine-2,1'-cyclopentan]-4-yl)methoxy)sulfonyl)amide;
Sodium (S)-(((4H-spiro[benzo[d][1,3]dioxine-2,1'-cyclopentan]-4-yl)methoxy)sulfonyl)amide;
Sodium (((4H-spiro[benzo[d][1,3]dioxine-2,1'-cyclopentan]-4-yl)methoxy)sulfonyl)amide;
Sodium ((6-chloro-(4H-spiro[benzo[d][1,3]dioxine-2,1'-cyclopentan]-4-yl)methoxy)sulfonyl)amide;
Sodium ((2-(2,2-dimethyl-4H-benzo[d][1,3]dioxin-4-yl)ethoxy)sulfonyl)amide;
Sodium ((2-(4H-spiro[benzo[d][1,3]dioxine2,1'-cyclopentan]-4-yl)ethoxy)sulfonyl)amide;
Potassium (R)-(((2,2-dimethyl-4H-benzo[d][1,3]dioxin-4-yl)methoxy)sulfonyl)amide;
Potassium (S)-(((2,2-dimethyl-4H-benzo[d][1,3]dioxin-4-yl)methoxy)sulfonyl)amide;
Potassium (((2,2-dimethyl-4H-benzo[d][1,3]dioxin-4-yl)methoxy)sulfonyl)amide; and
Lithium (S)-(((2,2-dimethyl-4H-benzo[d][1,3]dioxin-4-yl)methoxy)sulfonyl)amide.

8. The compound or the pharmaceutically acceptable salt thereof according to claim 1, wherein the compound is in the form of a racemate, an enantiomer, a diastereomer, a mixture of enantiomers, or a mixture of diastereomers.

9. A method of alleviating or treating pain in a subject in need thereof comprising administering a pharmaceutically effective amount of a pharmaceutical composition comprising a sulfamate compound represented by the following Chemical Formula 1 or a pharmaceutically acceptable salt thereof as an active ingredient:

[Chemical Formula 1]

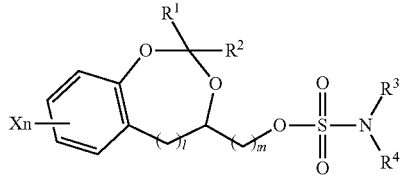

wherein X is selected from the group consisting of hydrogen, hydroxyl, $C_1$-$C_5$ alkoxy, $C_1$-$C_5$ alkyl, $C_1$-$C_5$ alkylthio, cyano, nitro, amine, $C_1$-$C_5$ alkylamine and halogen;
$R^1$ and $R^2$ are each independently selected from the group consisting of hydrogen, $C_1$-$C_5$ alkyl group, $C_2$-$C_5$ alkenyl and $C_6$-$C_{10}$ aryl group, or $R_1$ and $R_2$ together with the carbon atom to which they attach form a $C_3$-$C_{12}$ cycloalkyl group;
$R^3$ and $R^4$ are each independently hydrogen or $C_1$-$C_3$ alkyl; and
l, m and n are each independently an integer of 0 to 4.

10. The method according to claim 9, wherein X is H, OMe, Cl, F, or I; and n is an integer 1-4.

11. The method according to claim 9, wherein l or m are each independently an integer 0 or 1.

12. The method according to claim 9, wherein $R^1$ and $R^2$ are each independently methyl, ethyl, or isopropyl or $R^1$ and $R^2$ together with the carbon atom to which they attach form a cyclopentyl or a cyclohexyl group.

13. The method according to claim 9, wherein $R^3$ and $R^4$ are each independently hydrogen or methyl.

14. The method according to claim 9, wherein
X is chlorine, fluorine, iodine, bromine, methoxy or H;
n is an integer from 1-4;
$R^1$ and $R^2$ are each dependently selected from the group consisting of methyl, ethyl and isopropyl, or $R_1$ and $R_2$ together with the carbon atom to which they attach form a cyclopentyl or a cyclohexyl ring;
$R^3$ and $R^4$ are each dependently selected from the group consisting of H, methyl, ethyl, and isopropyl;
l and m are each dependently an integer from 0, 1 or 2.

15. The method according to claim 9, wherein the compound is selected from the group consisting of:
((R)-2,2-dimethyl-4H-benzo[d][1,3]dioxin-4-yl)methyl sulfamate;
((S)-2,2-dimethyl-4H-benzo[d][1,3]dioxin-4-yl)methyl sulfamate;
(2,2-dimethyl-4H-benzo[d][1,3]dioxin-4-yl))methyl sulfamate;
((R)-2,2-diethyl-4H-benzo[d][1,3]dioxin-4-yl)methyl sulfamate;
((S)-2,2-diethyl-4H-benzo[d][1,3]dioxin-4-yl)methyl sulfamate;
(2,2-diethyl-4H-benzo[d][1,3]dioxin-4-yl))methyl sulfamate;
((R)-4H-spiro[benzo[d][1,3]dioxine-2,1'-cyclopentan]-4-yl)methyl sulfamate;
((S)-4H-spiro[benzo[d][1,3]dioxine-2,1'-cyclopentan]-4-yl)methyl sulfamate;
(4H-spiro[benzo[d][1,3]dioxine-2,1'-cyclopentan]-4-yl) methyl sulfamate;
((R)-4H-spiro[benzo[d][1,3]dioxine-2,1'-cyclohexan]-4-yl)methyl sulfamate;
((S)-4H-spiro[benzo[d][1,3]dioxine-2,1'-cyclohexan]-4-yl)methyl sulfamate;
(4H-spiro[benzo[d][1,3]dioxine-2,1'-cyclohexan]-4-yl) methyl sulfamate;
2-(2,2-dimethyl-4H-benzo[d][1.3]dioxin-4-yl)ethyl sulfamate;
2-(2,2-diethyl-4H-benzo[d][1.3]dioxin-4-yl)ethyl sulfamate;
2-(4H-spiro[benzo[d][1.3]dioxine-2,1'-cyclopentan]-4-yl)ethyl sulfamate;
2-(4H-spiro[benzo[d][1.3]dioxine-2,1'-cyclohexan]-4-yl) ethyl sulfamate;
(2,2-dimethyl-4,5-dihydrobenzo[d][1,3]dioxepin-4-yl) methyl sulfamate;
(2,2-diethyl-4,5-dihydrobenzo[d][1,3]dioxepin-4-yl) methyl sulfamate;
(4,5-dihydrospiro[benzo[d][1,3]dioxepine-2,1'-cyclopentan]-4-yl)methyl sulfamate;

(4,5-dihydrospiro[benzo[d][1,3]dioxepine-2,1'-cyclohexan]-4-yl)methyl sulfamate;
2-(2,2-dimethyl-4,5-dihydrobenzo[d][1,3]dioxepin-4-yl)ethyl sulfamate;
2-(2,2-diethyl-4,5-dihydrobenzo[d][1,3]dioxepin-4-yl)ethyl sulfamate;
2-(4,5-dihydrospiro[benzo[d][1,3]dioxepine-2,1'-cyclopentan]-4-yl)ethyl sulfamate;
2-(4,5-dihydrospiro[benzo[d][1,3]dioxepine-2,1'-cyclohexan]-4-yl)ethyl sulfamate;
((R)-8-chloro-2,2-dimethyl-4H-benzo[d][1,3]dioxin-4-yl)methyl sulfamate;
((S)-8-chloro-2,2-dimethyl-4H-benzo[d][1,3]dioxin-4-yl)methyl sulfamate;
(8-chloro-2,2-dimethyl-4H-benzo[d][1,3]dioxin-4-yl)methyl sulfamate;
((R)-8-chloro-2,2-diethyl-4H-benzo[d][1,3]dioxin-4-yl)methyl sulfamate;
((S)-8-chloro-2,2-diethyl-4H-benzo[d][1,3]dioxin-4-yl)methyl sulfamate;
(8-chloro-2,2-diethyl-4H-benzo[d][1,3]dioxin-4-yl)methyl sulfamate;
((R)-8-chloro-4H-spiro[benzo[d][1,3]dioxine-2,1'-cyclopentan]-4-yl)methyl sulfamate;
((S)-8-chloro-4H-spiro[benzo[d][1,3]dioxine-2,1'-cyclopentan]-4-yl)methyl sulfamate;
(8-chloro-4H-spiro[benzo[d][1,3]dioxine2,1'-cyclopentan]-4-yl)methyl sulfamate;
((R)-8-chloro-4H-spiro[benzo[d][1,3]dioxine-2,1'-cyclohexan]-4-yl)methyl sulfamate;
((S)-8-chloro-4H-spiro[benzo[d][1,3]dioxine-2,1'-cyclohexan]-4-yl)methyl sulfamate;
(8-chloro-4H-spiro[benzo[d][1,3]dioxine-2,1'-cyclohexan]-4-yl)methyl sulfamate;
2-(8-chloro-2,2-dimethyl-4H-benzo[d][1,3]dioxin-4-yl)ethyl sulfamate;
2-(8-chloro-2,2-diethyl-4H-benzo[d][1,3]dioxin-4-yl)ethyl sulfamate;
2-(8-chloro-4H-spiro[benzo[d][1,3]dioxine-2,1'-cyclopentan]-4-yl)ethyl sulfamate;
2-(8-chloro-4H-spiro[benzo[d][1,3]dioxine-2,1'-cyclohexan]-4-yl)ethyl sulfamate;
2-(9-chloro-2,2-dimethyl-4,5-dihydrobenzo[d][1,3]dioxepin-4-yl)ethyl sulfamate;
2-(9-chloro-2,2-diethyl-4,5-dihydrobenzo[d][1,3]dioxepin-4-yl)ethyl sulfamate;
2-(9-chloro-4,5-dihydrospiro[benzo[d][1,3]dioxepine-2,1'-cyclopentan]-4-yl)ethyl sulfamate;
2-(9-chloro-4,5-dihydrospiro[benzo[d][1,3]dioxepine-2,1'-cyclohexan]-4-yl)ethyl sulfamate;
(7-chloro-2,2-dimethyl-4H-benzo[d][1,3]dioxin-4-yl)methyl sulfamate;
((R)-6-chloro-2,2-dimethyl-4H-benzo[d][1,3]dioxin-4-yl)methyl sulfamate;
((S)-6-chloro-2,2-dimethyl-4H-benzo[d][1,3]dioxin-4-yl)methyl sulfamate;
(6-chloro-2,2-dimethyl-4H-benzo[d][1,3]dioxin-4-yl)methyl sulfamate;
((R)-6-chloro-2,2-diethyl-4H-benzo[d][1,3]dioxin-4-yl)methyl sulfamate;
((S)-6-chloro-2,2-diethyl-4H-benzo[d][1,3]dioxin-4-yl)methyl sulfamate;
(6-chloro-2,2-diethyl-4H-benzo[d][1,3]dioxin-4-yl)methyl sulfamate;
(6-chloro-4H-spiro[benzo[d][1,3]dioxine-2,1'-cyclopentan]-4-yl)methyl sulfamate;
(6-chloro-4H-spiro[benzo[d][1,3]dioxine-2,1'-cyclohexan]-4-yl)methyl sulfamate;
(6-fluoro-2,2-dimethyl-4H-benzo[d][1,3]dioxin-4-yl)methyl sulfamate;
2-(6-fluoro-2,2-dimethyl-4H-benzo[d][1,3]dioxin-4-yl)ethyl sulfamate;
(7-fluoro-2,2-dimethyl-4,5-dihydrobenzo[d][1,3]dioxepin-4-yl)methyl sulfamate;
(6-methoxy-2,2-dimethyl-4H-benzo[d][1,3]dioxin-4-yl)methyl sulfamate;
Sodium (R)-(((2,2-dimethyl-4H-benzo[d][1,3]dioxin-4-yl)methoxy)sulfonyl)amide Trihydrate;
Sodium (S)-(((2,2-dimethyl-4H-benzo[d][1,3]dioxin-4-yl)methoxy)sulfonyl)amide Trihydrate;
Sodium (((2,2-dimethyl-4H-benzo[d][1,3]dioxin-4-yl)methoxy)sulfonyl)amide Trihydrate;
Sodium (R)-(((6-chloro-2,2-dimethyl-4H-benzo[d][1,3]dioxin-4-yl)methoxy)sulfonyl)amide;
Sodium (S)-(((6-chloro-2,2-dimethyl-4H-benzo[d][1,3]dioxin-4-yl)methoxy)sulfonyl)amide;
Sodium (((6-chloro-2,2-dimethyl-4H-benzo[d][1,3]dioxin-4-yl)methoxy)sulfonyl)amide;
Sodium (R)-(((4H-spiro[benzo[d][1,3]dioxine-2,1'-cyclopentan]-4-yl)methoxy)sulfonyl)amide;
Sodium (S)-(((4H-spiro[benzo[d][1,3]dioxine-2,1'-cyclopentan]-4-yl)methoxy)sulfonyl)amide;
Sodium (((4H-spiro[benzo[d][1,3]dioxine-2,1'-cyclopentan]-4-yl)methoxy)sulfonyl)amide;
Sodium ((6-chloro-(4H-spiro[benzo[d][1,3]dioxine-2,1'-cyclopentan]-4-yl)methoxy)sulfonyl)amide;
Sodium ((2-(2,2-dimethyl-4H-benzo[d][1,3]dioxin-4-yl)ethoxy)sulfonyl)amide
Sodium ((2-(4H-spiro[benzo[d][1,3]dioxine2,1'-cyclopentan]-4-yl)ethoxy)sulfonyl)amide;
Potassium (R)-(((2,2-dimethyl-4H-benzo[d][1,3]dioxin-4-yl)methoxy)sulfonyl)amide;
Potassium (S)-(((2,2-dimethyl-4H-benzo[d][1,3]dioxin-4-yl)methoxy)sulfonyl)amide;
Potassium (((2,2-dimethyl-4H-benzo[d][1,3]dioxin-4-yl)methoxy)sulfonyl)amide; and
Lithium (S)-(((2,2-dimethyl-4H-benzo[d][1,3]dioxin-4-yl)methoxy)sulfonyl)amide.

16. The method according to claim 9, wherein the compound is in the form of a racemate, an enantiomer, a diastereomer, a mixture of enantiomers, or a mixture of diastereomers.

17. The method according to claim 9, wherein the pain is one or more selected from the group consisting of nociceptive pain, psychogenic pain, inflammatory pain, and pathological pain.

18. The method according to claim 9, wherein the pain is one or more selected from the group consisting of neuropathic pain, cancer pain, postoperative pain, trigeminal neuralgia pain, idiopathic pain, diabetic neuropathic pain, and migraine.

19. A pharmaceutical composition comprising a pharmaceutically effective amount of a compound according to claim 1.

20. The pharmaceutical composition according to claim 19, wherein the compound is in the form of a racemate, an enantiomer, a diastereomer, a mixture of enantiomers, or a mixture of diastereomers.

21. A process of the preparation of a compound of Chemical Formula 1, comprising the step of performing a sulfamoylation of a compound of Chemical Formula 10 by reacting the compound of Chemical Formula 10 with a sulfamoylation reagent, to produce a sulfamate compound of Chemical Formula 1:

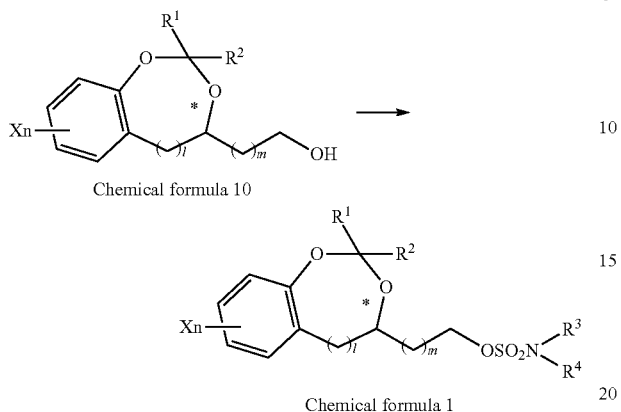

Chemical formula 10

Chemical formula 1 wherein X is selected from the group consisting of hydroxyl, $C_1$-$C_5$ alkoxy, $C_1$-$C_5$ alkyl, $C_2$-$C_5$ alkenyl, $C_6$-$C_{10}$ aryl, $C_1$-$C_5$ alkoxycarbonyl, carboxyl, $C_2$-$C_5$ acyl, $C_1$-$C_5$ alkylthio, cyano, nitro, amine, $C_1$-$C_5$ alkylamine and halogen;

$R^1$ and $R^2$ are each independently selected from the group consisting of hydrogen, $C_1$-$C_5$ alkyl group, $C_2$-$C_5$ alkenyl and $C_6$-$C_{10}$ aryl group, or $R_1$ and $R_2$ together with the carbon atom to which they attach form a $C_3$-$C_{12}$ cycloalkyl group;

$R^3$ and $R^4$ are each independently hydrogen or $C_1$-$C_3$ alkyl; and l, m and n are each independently an integer of 0 to 4.

22. The process according to claim 21, which further comprises the step of performing a reduction reaction an ester compound of Chemical Formula 17 by using a reducing agent in a basic condition, to produce the compound of Chemical Formula 10:

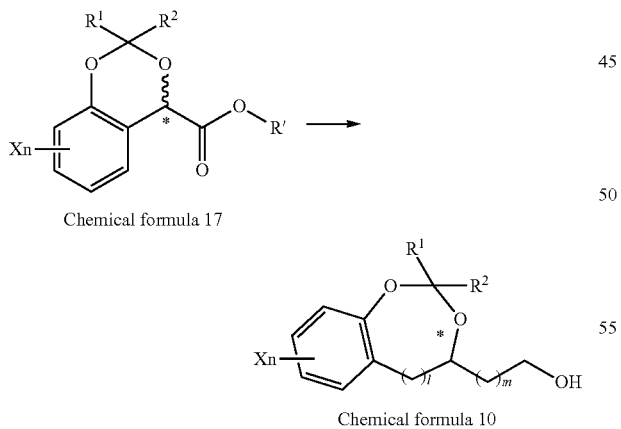

Chemical formula 17

Chemical formula 10 wherein X is selected from the group consisting of hydroxyl, $C_1$-$C_5$ alkoxy, $C_1$-$C_5$ alkyl, $C_2$-$C_5$ alkenyl, $C_6$-$C_{10}$ aryl, $C_1$-$C_5$ alkoxycarbonyl, carboxyl, $C_2$-$C_5$ acyl, $C_1$-$C_5$ alkylthio, cyano, nitro, amine, $C_1$-$C_5$ alkylamine and halogen;

$R^1$ and $R^2$ are each independently selected from the group consisting of hydrogen, $C_1$-$C_5$ alkyl group, $C_2$-$C_5$ alkenyl and $C_6$-$C_{10}$ aryl group, or $R_1$ and $R_2$ together with the carbon atom to which they attach form a $C_3$-$C_{12}$ cycloalkyl group;

R' is $C_1$-$C_5$ alkyl, $C_3$-$C_{12}$ cycloalkyl, $C_1$-$C_5$ alkyl $C_6$-$C_{10}$ aryl, or $C_6$-$C_{10}$ aryl, wherein any of said alkyl, cycloalkyl, and aryl are optionally substituted with one or more groups independently selected from the group consisting of hydroxyl, $C_1$-$C_5$ alkoxy, $C_1$-$C_5$ alkyl, $C_2$-$C_5$ alkenyl, $C_6$-$C_{10}$ aryl, $C_1$-$C_5$ alkoxycarbonyl, carboxyl, $C_2$-$C_5$ acyl, $C_1$-$C_5$ alkylthio, cyano, nitro, amine, $C_1$-$C_5$ alkylamine and halogen; and n is an integer of 0 to 4.

23. The process according to claim 22, which further comprises the step of performing a cyclization a diol compound of Chemical Formula 16 by using a ketone compound or an alkoxy compound in an acidic condition, to produce the compound of Chemical Formula 17:

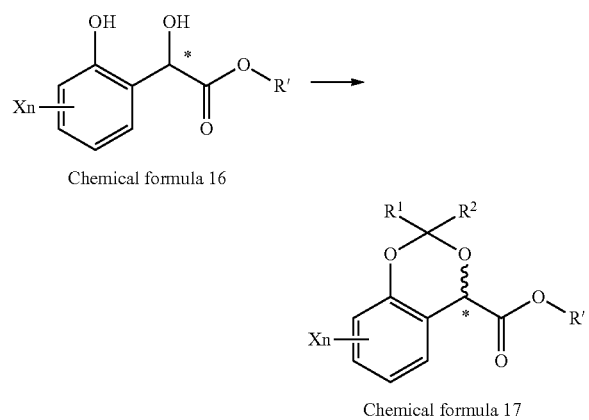

Chemical formula 16

Chemical formula 17 wherein X is selected from the group consisting of hydrogen, hydroxyl, $C_1$-$C_5$ alkoxy, $C_1$-$C_5$ alkyl, $C_2$-$C_5$ alkenyl, $C_6$-$C_{10}$ aryl, $C_1$-$C_5$ alkoxycarbonyl, carboxyl, $C_2$-$C_5$ acyl, $C_1$-$C_5$ alkylthio, cyano, nitro, amine, $C_1$-$C_5$ alkylamine and halogen;

$R^1$ and $R^2$ are each independently selected from the group consisting of hydrogen, $C_1$-$C_5$ alkyl group, $C_2$-$C_5$ alkenyl and $C_6$-$C_{10}$ aryl group, or $R_1$ and $R_2$ together with the carbon atom to which they attach form a $C_3$-$C_{12}$ cycloalkyl group;

R' is $C_1$-$C_5$ alkyl, $C_3$-$C_{12}$ cycloalkyl, $C_1$-$C_5$ alkyl $C_6$-$C_{10}$ aryl, or $C_6$-$C_{10}$ aryl, wherein any of said alkyl, cycloalkyl, and aryl are optionally substituted with one or more groups independently selected from the group consisting of hydroxyl, $C_1$-$C_5$ alkoxy, $C_1$-$C_5$ alkyl, $C_2$-$C_5$ alkenyl, $C_6$-$C_{10}$ aryl, $C_1$-$C_5$ alkoxycarbonyl, carboxyl, $C_2$-$C_5$ acyl, $C_1$-$C_5$ alkylthio, cyano, nitro, amine, $C_1$-$C_5$ alkylamine and halogen; and n is an integer of 0 to 4.

24. The process according to claim 23, which further comprises the step of performing an addition reaction an alcohol ester compound of Chemical Formula 15 by using a using a phenol compound of formula 14 in an acidic condition, to produce the compound of Chemical Formula 16:

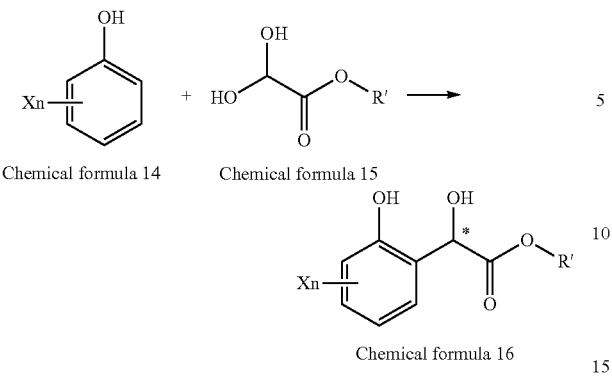

Chemical formula 14    Chemical formula 15

Chemical formula 16 wherein X is selected from the group consisting of hydrogen, hydroxyl, $C_1$-$C_5$ alkoxy, $C_1$-$C_5$ alkyl, $C_2$-$C_5$ alkenyl, $C_6$-$C_{10}$ aryl, $C_1$-$C_5$ alkoxycarbonyl, carboxyl, $C_2$-$C_5$ acyl, $C_1$-$C_5$ alkylthio, cyano, nitro, amine, $C_1$-$C_5$ alkylamine and halogen;

R' is $C_1$-$C_5$ alkyl, $C_3$-$C_{12}$ cycloalkyl, $C_1$-$C_5$ alkyl $C_6$-$C_{10}$ aryl, or $C_6$-$C_{10}$ aryl, wherein any of said alkyl, cycloalkyl, and aryl are optionally substituted with one or more groups independently selected from the group consisting of hydroxyl, $C_1$-$C_5$ alkoxy, $C_1$-$C_5$ alkyl, $C_2$-$C_5$ alkenyl, $C_6$-$C_{10}$ aryl, $C_1$-$C_5$ alkoxycarbonyl, carboxyl, $C_2$-$C_5$ acyl, $C_1$-$C_5$ alkylthio, cyano, nitro, amine, $C_1$-$C_5$ alkylamine and halogen; and n is an integer of 0 to 4.

* * * * *